US006893858B2

(12) United States Patent
Dworetzky et al.

(10) Patent No.: US 6,893,858 B2
(45) Date of Patent: May 17, 2005

(54) HUMAN KCNQ5 POTASSIUM CHANNEL, METHODS AND COMPOSITIONS THEREOF

(75) Inventors: Steven I. Dworetzky, Middlefield, CT (US); Chandra S. Ramanathan, Wallingford, CT (US); Joanne T. Trojnacki, Guilford, CT (US); Valentin K. Gribkoff, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 199 days.

(21) Appl. No.: 09/866,020

(22) Filed: May 24, 2001

(65) Prior Publication Data

US 2002/0040000 A1 Apr. 4, 2002

Related U.S. Application Data

(60) Provisional application No. 60/207,389, filed on May 26, 2000.

(51) Int. Cl.$^7$ .................. C07H 21/04; C12N 15/12; C12N 15/63; C07K 14/00; C07N 15/00
(52) U.S. Cl. .................. 435/252.3; 435/69.1; 435/6; 435/320.1; 435/325; 435/254.11; 530/350; 536/23.5
(58) Field of Search .................. 435/252.3, 254.11, 435/69.1, 6, 320.1, 325; 530/350; 536/23.5

(56) References Cited

U.S. PATENT DOCUMENTS

2002/0102677 A1 * 8/2002 Jegla .................. 435/183

FOREIGN PATENT DOCUMENTS

| WO | Wo 99/07832 | * 2/1999 | |
| WO | WO 00/61606 | 10/2000 | C07K/1/00 |
| WO | WO 00/77035 | 12/2000 | C07K/14/00 |
| WO | WO 01/70811 | 9/2001 | |

OTHER PUBLICATIONS

Voet et al. Biochemistry. 1990. John Wiley & Sons, pp. 126–128 and 228–234.*
Eck & Wilson in Goodman & Gilman's The Pharmacological Basis of Therapeutics. Ninth Edition. McGraw Hill, New York, 199 pages 77–101.*
A.D. Wickenden et al., 2001, Br. J. Pharmacol., 132(2):381–384.
C. Kananura et al., 2000, Neuroreport., 11(9):2063–7.
B.C. Schroeder et al., 2000, J. Biol. Chem., 4:275(31):24089–24095.
C. Lerche et al., 2000, J. Biol. Chem., 275(29):22395–22400.
NCBI Accession No. AF249278, *Homo sapiens* voltage-gated potassium channel (KCNQ5) mRNA, complete cds; Submitted: Mar. 24, 2000; Released: Aug. 2, 2000; Ref.: Lerche et al., 2000, J. Biol. Chem., 275(29):22395–22400.
NCBI Accession No. AF202977, *Homo sapiens* voltage-gated channel, KQT–like Subfamily, member 5 (KCNQ5) mRNA, Submitted: Nov. 9, 1999; Released Aug. 1, 2000; Ref.: Schroeder et al., 2000, J. Biol. Chem., 275(31):24089–24095.
NCBI Accession No. AF263836, Mus musculus voltage-gated potassium channel KCNQ5 (Kcnq5) mRNA, partial cds., Submitted: May 4, 2000; Released: Jun. 1, 2000; Ref.: M. Kniazeva et al., unpublished.
Database EBI "On line", Hinxton, UK. Accession No. AF202977, May 14, 2000.
Database EBI 'Online' Hinxton, UK; AW049888, Mar. 4, 2000, XP002173772, nucleotides 1–584.
Pongs, O. FEBS Letters, vol. 452, pp. 31–35 (1999).

* cited by examiner

*Primary Examiner*—Elizabeth Kemmerer
*Assistant Examiner*—Joseph F. Murphy
(74) *Attorney, Agent, or Firm*—John A. Lamerdin; Briana Buchholz

(57) ABSTRACT

An isolated polynucleotide encoding a novel potassium channel polypeptide, KCNQ5, that is expressed primarily in brain and skeletal muscle is described. The new polypeptide has been cloned and isolated from a human brain cDNA library and is a member the KCNQ family of potassium channels. The provided human KCNQ5 nucleic acid sequence and encoded polypeptide can be employed for diagnostic, screening and therapeutic uses. Moreover, the hKCNQ5 polypeptide can be used to assay for KCNQ5 potassium channel modulators, which can be utilized in the treatment of neurological, neurophysiological, neuropsychological and neuroaffective diseases, conditions and disorders, including, but not limited to, acute and chronic pain, migraine, acute stroke, dementia, vascular dementia, trauma, epilepsy, amyelotrophic lateral sclerosis (ALS), multiple sclerosis (MS), Parkinson's Disease, learning and cognitive disorders, and neurophysiological disorders including anxiety disorders, depression, bipolar disorders, sleep disorders, addiction, and eating disorders.

4 Claims, 26 Drawing Sheets

FIG. 1A

KCNQ5 cDNA coding sequence

| | | | | |
|---|---|---|---|---|
| atgaaggatg | tggagtcggg | ccggggcagg | gtgctgctga | 40 |
| actcggcagc | cgccagggc | gacggcctgc | tactgctggg | 80 |
| cacccgcgcg | gccacgcttg | gtggcggcgg | cggtggcctg | 120 |
| agggagagcc | gccggggcaa | gcaggggcc | cggatgagcc | 160 |
| tgctggggaa | gccgctctct | tacacgagta | gccagagctg | 200 |
| ccggcgcaac | gtcaagtacc | ggcgggtgca | gaactacctg | 240 |
| tacaacgtgc | tggagagacc | ccgcggctgg | gcgttcatct | 280 |
| accacgcttt | cgtttttctc | cttgtctttg | gttgcttgat | 320 |
| tttgtcagtg | ttttctacca | tccctgagca | cacaaaattg | 360 |
| gcctcaagtt | gcctcttgat | cctggagttc | gtgatgattg | 400 |
| tcgtctttgg | tttggagttc | atcattcgaa | tctggtctgc | 440 |
| gggttgctgt | tgtcgatata | gaggatggca | aggaagactg | 480 |
| aggtttgctc | gaaagcccctt | ctgtgttata | gataccattg | 520 |
| ttcttatcgc | ttcaatagca | gttgtttctg | caaaaactca | 560 |
| gggtaatatt | tttgccacgt | ctgcactcag | aagtctccgt | 600 |
| ttcctacaga | tcctccgcat | ggtgcgcatg | gaccgaaggg | 640 |
| gaggcacttg | gaaattactg | ggttcagtgg | tttatgctca | 680 |
| cagcaaggaa | ttaatcacag | cttggtacat | aggatttttg | 720 |
| gttcttattt | tttcgtcttt | ccttgtctat | ctggtggaaa | 760 |

FIG. 1B

```
aggatgccaa taaagagttt tctacatatg cagatgctct   800
ctggtggggc acaattacat tgacaactat tggctatgga   840
gacaaaactc ccctaacttg gctgggaaga ttgctttctg   880
caggctttgc actccttggc atttctttct ttgcacttcc   920
tgccggcatt cttggctcag gttttgcatt aaaagtacaa   960
gaacaacacc gccagaaaca ctttgagaaa agaaggaacc  1000
cagctgccaa cctcattcag tgtgtttggc gtagttacgc  1040
agctgatgag aaatctgttt ccattgcaac ctggaagcca  1080
cacttgaagg ccttgcacac ctgcagccct accaagaaag  1120
aacaagggga agcatcaagc agtcagaagc taagttttaa  1160
ggagcgagtg cgcatggcta gccccagggg ccagagtatt  1200
aagagccgac aagcctcagt aggtgacagg aggtccccaa  1240
gcaccgacat cacagccgag ggcagtccca ccaaagtgca  1280
gaagagctgg agcttcaacg accgacccg cttccggccc  1320
tcgctgcgcc tcaaaagttc tcagccaaaa ccagtgatag  1360
atgctgacac agcccttggc actgatgatg tatatgatga  1400
aaaaggatgc cagtgtgatg tatcagtgga agacctcacc  1440
ccaccactta aaactgtcat tcgagctatc agaattatga  1480
aatttcatgt tgcaaaacgg aagtttaagg aaacgttacg  1520
tccatatgat gtaaaagatg tcattgaaca atattctgct  1560
```

FIG. 1C

```
ggtcatctgg acatgttgtg tagaattaaa agccttcaaa    1600
cacgtgttga tcaaattctt ggaaaagggc aaatcacatc    1640
agataagaag agccgagaga aaataacagc agaacatgag    1680
accacagacg atctcagtat gctcggtcgg gtggtcaagg    1720
ttgaaaaaca ggtacagtcc atagagtcca agctggactg    1760
cctactagac atctatcaac aggtccttcg gaaaggctct    1800
gcctcagccc tcgctttggc ttcattccag atcccacctt    1840
ttgaatgtga acagacatct gactatcaaa gccctgtgga    1880
tagcaaagat ctttcgggtt ccgcacaaaa cagtggctgc    1920
ttatccagat caactagtgc caacatctcg agaggcctgc    1960
agttcattct gacgccaaat gagttcagtg cccagacttt    2000
ctacgcgctt agccctacta tgcacagtca agcaacacag    2040
gtgccaatta gtcaaagcga tggctcagca gtggcagcca    2080
ccaacaccat tgcaaaccaa ataaatacgg cacccaagcc    2120
agcagcccca acaactttac agatcccacc tcctctccca    2160
gccatcaagc atctgcccag gccagaaact ctgcacccta    2200
accctgcagg cttacaggaa agcatttctg acgtcaccac    2240
ctgccttgtt gcctccaagg aaaatgttca ggttgcacag    2280
tcaaatctca ccaaggaccg ttctatgagg aaaagctttg    2320
acatgggagg agaaactctg ttgtctgtct gtccatggt    2360 gccgaaggac ttgggcaaat ctttgtctgt gcaaaacctg    2400
atcaggtcga ccgaggaact gaatatacaa ctttcaggga    2440
```

FIG. 1D

```
gtgagtcaag tggctccaga ggcagccaag atttttaccc      2480
caaatggagg gaatccaaat tgtttataac tgatgaagag      2520
gtgggtcccg aagagacaga gacagacact tttgatgccg      2560
caccgcagcc tgccagggaa gctgcctttg catcagactc      2600
tctaaggact ggaaggtcac gatcatctca gagcatttgt      2640
aaggcaggag aaagtacaga tgccctcagc ttgcctcatg      2680
tcaaactgaa ataa                                   2694
```

FIG. 2A

KCNQ5 Protein Sequence

| | | | | |
|---|---|---|---|---|
| MKDVESGRGR | VLLNSAAARG | DGLLLLGTRA | ATLGGGGGGL | 40 |
| RESRRGKQGA | RMSLLGKPLS | YTSSQSCRRN | VKYRRVQNYL | 80 |
| YNVLERPRGW | AFIYHAFVFL | LVFGCLILSV | FSTIPEHTKL | 120 |
| ASSCLLILEF | VMIVVFGLEF | IIRIWSAGCC | CRYRGWQGRL | 160 |
| RFARKPFCVI | DTIVLIASIA | VVSAKTQGNI | FATSALRSLR | 200 |
| FLQILRMVRM | DRRGGTWKLL | GSVVYAHSKE | LITAWYIGFL | 240 |
| VLIFSSFLVY | LVEKDANKEF | STYADALWWG | TITLTTIGYG | 280 |
| DKTPLTWLGR | LLSAGFALLG | ISFFALPAGI | LGSGFALKVQ | 320 |
| EQHRQKHFEK | RRNPAANLIQ | CVWRSYAADE | KSVSIATWKP | 360 |
| HLKALHTCSP | TKKEQGEASS | SQKLSFKERV | RMASPRGQSI | 400 |
| KSRQASVGDR | RSPSTDITAE | GSPTKVQKSW | SFNDRTRFRP | 440 |
| SLRLKSSQPK | PVIDADTALG | TDDVYDEKGC | QCDVSVEDLT | 480 |
| PPLKTVIRAI | RIMKFHVAKR | KFKETLRPYD | VKDVIEQYSA | 520 |
| GHLDMLCRIK | SLQTRVDQIL | GKGQITSDKK | SREKITAEHE | 560 |
| TTDDLSMLGR | VVKVEKQVQS | IESKLDCLLD | IYQQVLRKGS | 600 |
| ASALALASFQ | IPPFECEQTS | DYQSPVDSKD | LSGSAQNSGC | 640 |
| LSRSTSANIS | RGLQFILTPN | EFSAQTFYAL | SPTMHSQATQ | 680 |
| VPISQSDGSA | VAATNTIANQ | INTAPKPAAP | TTLQIPPPLP | 720 |
| AIKHLPRPET | LHPNPAGLQE | SISDVTTCLV | ASKENVQVAQ | 760 |
| SNLTKDRSMR | KSFDMGGETL | LSVCPMVPKD | LGKSLSVQNL | 800 |
| IRSTEELNIQ | LSGSESSGSR | GSQDFYPKWR | ESKLFITDEE | 840 |

FIG. 2B

VGPEETETDT FDAAPQPARE AAFASDSLRT GRSRSSQSIC          880

KAGESTDALS LPHVKLK                                   897

FIG. 3

Alternative Splice Exon 1

| TGG | GGA | CAG | TGG | ACA | TTG | CGT |
|-----|-----|-----|-----|-----|-----|-----|
| Trp | Gly | Gln | Trp | Thr | Leu | Arg |

FIG. 4A

3' UTR

| | | | | |
|---|---|---|---|---|
| gttcttcatt | ttctttccag | gcatagcagt | tctttagcca | 40 |
| tacatatcat | tgcatgaact | atttcgaaag | cccttctaaa | 80 |
| aagttgaaat | tgcaagaatc | gggaagaaca | tgaaaggcag | 120 |
| tttataagcc | cgttaccttt | taattgcatg | aaaatgcatg | 160 |
| tttagggatg | gctaaaattc | caaggtgcat | cgacattaac | 200 |
| ccactcattt | agtaatgtac | cttgagttaa | aaagcctgag | 240 |
| aaaccaaaca | cagctaatgc | tatggggtgt | atgaatatgt | 280 |
| caagtttagg | tcatttagaa | gatttgacac | tgtatttga | 320 |
| aattatgagt | aaacaccttc | aaatttcagg | catttctgct | 360 |
| ttgtgactaa | atacaaacta | cattttcaag | attaggccat | 400 |
| aatgtatatt | taaacacaat | ggctatcaac | agctgctaat | 440 |
| aaggtatcaa | ctaaagcaga | attggggaat | aatagaaatg | 480 |
| gctgcttatt | tcaagatata | tttgccaacc | cattcctatt | 520 |
| cagtcatttt | attattaatg | taatttgaat | gtcaatttgt | 560 |
| gtgcttttgg | tgatttagcg | ctgtggcaag | caattttgca | 600 |
| catcattttc | atgttgttct | ttatgacaag | aatgttcttc | 640 |
| aattagaaaa | tgtgcaaata | atgaaattca | gggccagtga | 680 |
| ggcaaataga | ctatctgaca | tatttgactt | tatgaaaaca | 720 |
| tattgcctga | tggcagaatc | aactttataa | gtggtcaact | 760 |
| tctacacaag | cgtatgaaat | actggtcagt | agaacagcca | 800 |

FIG. 4B

```
ttgtgattgg actggtttct ctgcaatggc gccaacccca      840
ggcttgccaa tactgcctat gtaaagggca agtgtgagaa      880
gctattctca tttcgctgac atacaggtag gactatgggg      920
gatgggacat ttgagtggga ctgagatagg aaaggcttga      960
aaagaaccca gaaacaccac caggaagttg gcaaagtaaa     1000
agaaaatgac ttcccccctca aagggcaatg agagggagag    1040
aaacaaacca aaatagaaga actagacttt ttagaaaatg     1080
agtattgcta                                     1090
```

FIG. 5A

Multiple Sequence Alignment of the KCNQ Channel Family Members

```
hskcnq4  --------------------------MAEAPPRRLGLGPPPGDAPRAE.LVALTAVQSEQSEGG.
hskcnq5  -----------------------MKDVESGR.GRVLLNSAAARGDGLLLLGTRAATLGGGG.
hskcnq2  -----------------------MVQKSRNG.GVYPG..PSGEKKLKVGFVGLDPG.GP.
hskcnq3  MGLKARRAAGAAGGGGDGGGGGGGAANPAGSDAAAAGDEERKVGLAPGDVEQVTLGLGA.
hskcnq1  -------------MAAASSPPRAERKRWGWGRLPGARRGSAGLAKKCPFSLRLGEGGP hskcnq4  GGGSPRRLGLLGSPLP.PGAPLPGPGSG.SGSACGQGSSAA.HKR...M..RR.......
hskcnq5  GGLRESRRGKQGARMSLLGKPL...SYT.SSQSC.RG.....NVK...M..RR.......
hskcnq2  DSTRDGALLIAGSEAPKRGSILSKPRAG.GAGA..GGPPKR.NAF...M..RR.......
hskcnq3  GADKDGTLLLEGGGRDE.GQRRTPQGIGLLAKTPLSGPVKRNKAK...M..RR.......
hskcnq1  AGGALYAPIAPGAPGPAPPASPAAPAAPPVASDLCPGDPVSLDPRVSIGSTRGPVLARTH hskcnq4  LDNWGYNVLERSRGW.AFGYHVFGFLGVFSGLGLSMLGIQEHQELANECGLIGEFVMGV
hskcnq5  GCNYGYNVLERSRGW.AFGYHAFGFLGVFGCIGLSVFGIPEHTKLASSCGLIGEFVMGV
hskcnq2  GGNFGYNVLERPRGW.AFGYHAYGFLGVFSCLGLSVFGIKEYEKSSEGAGYIGEIVTGV
hskcnq3  GTLGGDALGRRGW.ALGVHALGFLGVLGCLGLAVLGFKEYETVSGDWGLLGGTFAGF
hskcnq1  GGRGYNFLGERYTGWKCFGYHFAKGFLGVLVCLGFSVLGIEQYAALATGTGFWGGIVLGV hskcnq4  VFGLFGIGRMGSAGCCGYRGWQGRFGFARKPFCGIDFIGFGAGTAVIAAGTQGGIFATS
hskcnq5  VFGLFGIGRGTSAGCCGYRGWQGRLGFARKPFCGIDTIGLGASTAVGSAKTQGGRFATS
hskcnq2  VFGVFRGGRGAGGGCCGYRFWRGRLGARKPFCGIDIMVLGASGAVAAGSQGGGFATS
hskcnq3  IFGAFFAFGRTNAGGCCGYRGWRGRLGFARKPLCGDIFVLGASGPVGAVGNQGGGLATS
hskcnq1  FFGTEGGVGRGSAGGRSGYVGLMGTGLGARKFISGGDLIVVGASGVGCVGSKGGFATS hskcnq4  AGRSGRFLQILRMGRMDRRGGTWGLLGSVGYAGSKSLGTAWYIGFLVLGFASGLVYLAEK
hskcnq5  AGRSGRFLQILRMGRMDRRFGTWGLLGSVGYAGSKELGTAWYIGFLVLGFSSGLVYIVEK
hskcnq2  AGRSGRFLQILRMGRMDRRGGTWGLLGSVGYAGSKSLGTAWYIGFLCLGLASGLVYLAEK
hskcnq3  .GRSGRFLQILRMGRMDRRGGTWGLLGSAGCAGSKELGTGAWYIGPITGLLSSGLVYLVEK
hskcnq1  AGRGGRFLQILRMGKGDRQGGTWGLLGSVGFIGRQBLGPTLGYIGFLGLGFSSGFVYLAEK hskcnq4  DA.........NSDGSGYADSLWGTGGGTTGGGYGDKGPHGLGVEAACGAGLGGSFF
hskcnq5  DA.........NKEGSGYALAGGGTGGGTGIGYGDKTPLTWLGLLSAGFAGLGGSPF
hskcnq2  GE.........NDHGDGYADALWGLGGTGIGYGDKYPQTGGGLAATGGGGGSFF
hskcnq3  DVPEVDAQGEEMKEEGYADALRWGLGGGATIGYGDKGFKTGGDGGLAAIGSGLGGSFF
hskcnq1  DAVNESGRV.....EGGSYADAGKWGVGGTGGIGYGDKVPQTWVGRTGASCGSGFGSFF hskcnq4  ALPAGILGSCFALKVQEQHRQKHFEKRRMPAAGGLIQAAPRLYSTDMSRAYLTAGGYYDS
hskcnq5  ALPAGILGSCFALKVQEQHRQKHFEKRRNPAAGGLIQCVWRSGAAD.EKSVSIATN.....
hskcnq2  ALPAGILGSCFALKVCEQHRQKHFEKRRNPAAGGLIQSAGRFGATNLSRTDLHSGQYYER
hskcnq3  ALPAGILGSCLALKVQEQHRQKHFEKRRKPAAEGLICAANRGGATNPNRIDLVATGRFYES
hskcnq1  ALPAGILGSGFALEVQKCGRQKHFNEQIPAAGSLGQTAGGCGAAENPDS...SGGKIY..

hskcnq4  ..ILPSFGELALLFEHVQPRARNGGLRPLEVRRAPVPDGAPSRYPPVATCHRPGSTSFCPG
hskcnq5  ...KPHLGAL.....HT..................CSPTK.......KEQGEAS....
hskcnq2  TVTVPMYGLIPPLNQLELLRNLKSKSGLAFRKDPPPEPSP...................
hskcnq3  VVSFPFF.................................KEQLEAA....
hskcnq1  ......IGKAP..RSHTLLS.............PSPKPKKSVVVKKKKFKLDKDNGVT
```

FIG. 5B

```
hskcnq4  ESSQIGIKDRIRMGSSQRRTGPS.KQQLAPPTMPTDSSEQVGEATSPTKVQKSWSFNDR
hskcnq5  SSQKISFKERIRMASPRGQSIKS.RQ..ASVGDRRSPSTDITAEG.SPTKVQKSWSFNDR
hskcnq2  .SQKISLKDRI.FSSPRGVAAKG.KGSPQAQTVRRSPSADQSLE.DSPSKVPKSWSFGDR
hskcnq3  SSQKIGLLDRIRLSNPRGSNTKG.KLF........PLNVDAIS.ESPSKEPKPVGLNNK
hskcnq1  PGEKILTVPHITCDPPBERRLDHFSVDGYDSSVRKSPT...LLSVSME............

hskcnq4  TRFRASLRL.....KPRTSAEDA.PSEEIAEEKSYQCELTVDDIMPAVETVISERIKKE
hskcnq5  TRFRPSLRLKSSQPKPVIDAPTALGTDDIYDEKGCQCDVSVEDITPPLATVIAMRIKE
hskcnq2  SRARQAFIIKGAASR.QNSEIASLPGEDIVDDKSCPCEFVTEDITPGLIVSIACVMRE
hskcnq3  ERFRTAPIMKAYAFWQ..SSIDAGTGDPIAEDRGYGNDFPIBDMIPTLIAAIMAMRICE
hskcnq1  .HF...MITNSFAEDLDLEGITLLT..PITH.........ISQIREHHIATIKVERRMQI hskcnq4  LIAKIKFKETLSPYDVKDVIEQYSAGHIDMIGRIKSLQTRIDQIVGRG...PGDR.KARE
hskcnq5  HIAKIKFKETLSPYDVKDVIEQYSAGHIDMIGRIKSLQTRILQILGKGQI.TSDK.KSRE
hskcnq2  LISKIKFKESLPYDVMDVIEQYSAGHIDMISRIKSLQSRIDQIVGRGPA.ITD..KDR.
hskcnq3  RIYKIKFKETLIPYDVKDVIEQYSAGHIDMISRIKYLQTRIDMIFTPGPP.STPKHIKSQ
hskcnq1  FIAKIKFQQARKIPYDVRDVIEQYSQGHLNIVRIKELQRRIDQSIGKPSLFISVSELSKD hskcnq4  KGDKG...............PSDAEVVIEISMIGRVVKIE..KQVQSIEHKLILLLGPY
hskcnq5  ...KI................TAEHETTIDLSMIGRVVKIE..KQVQSIESKLICLLDIY
hskcnq2  ..TKG...............PAEAELPIDPSMIGRLGKIE..KQVLSMEKKLIFLVNIY
hskcnq3  KGSAFTFPSQQSPRMEPYVARPSTSEI.IDQSMIGKFVKIE..RQVQDMGKKLIFLVDMH
hskcnq1  RGSNTIGARLNRVEDKVTQLDQRLALITI...MIHQLLSIHGGSTPGSGGPPRIGGAHIT hskcnq4  SRCLRSGT..SA.SLGAVQVPLFIPDITSDYHSIVIH..EDISVSAQTLS.ISRSVSTNM
hskcnq5  QQVLRKGSA.SALALASFQIPPFICEQTSDYQSIVIS..KDLSGSAQNSGCLSRSTSANI
hskcnq2  MQ..RMGIP.PTETEAYFGAK..IPEPAPPYHSIEIS..RB...HVDRHGCIVKIVRSSS
hskcnq3  MQHMER..........LQVQVTIYYPTKGTSSIAIAEKKEDNRYSDLKTIICNYSETGP
hskcnq1  QPCGSGGSVDPELFLPSNTLPTYI.QLTVPRRGIDIGS~~~~~~~~~~~~~~~~~~~~~~ hskcnq4  D~~~~~~~~~~~~~~~~~~~~~~~~~~~~~~~~~~~~~~~~~~~~~~~~~~~~~~~~~
hskcnq5  SRGLQFI..LTPNEFSAQTFYALSPTMHSQATQVPISQSDGSAVAATNTIANQINTAPKP
hskcnq2  STGQKNF..SAPPAAPP....VQCPPSTSWQPQSHPRQCHGTSPVGDHGSLVRIPPPPAH
hskcnq3  PEPPYSFHQVTIDKVSPYGFFAHDPVNLPRGGPSS.GKVQATPPSSATTYVERPTVLPIL
hskcnq1  ~~~~~~~~~~~~~~~~~~~~~~~~~~~~~~~~~~~~~~~~~~~~~~~~~~~~~~~~~~ hskcnq4  ~~~~~~~~~~~~~~~~~~~~~~~~~~~~~~~~~~~~~~~~~~~~~~~~~~~~~~~~~~
hskcnq5  AAPTTLQIPPPLPAIKHLPRPETLHPNPAGLQESISDVTTCLVASKENVQVAQSNLTKDR
hskcnq2  ERSLSAYGGGNRASMEFLRQEDTPGCRPPEGTLRDSDTSISIPSVDHEELERSFSGFSIS
hskcnq3  TLLDSRVSCHSQADLQG.PYSDRISPRQRRSITRDSDTPLSLMSVNHEELERSPSGFSIS
hskcnq1  ~~~~~~~~~~~~~~~~~~~~~~~~~~~~~~~~~~~~~~~~~~~~~~~~~~~~~~~~~~ hskcnq4  ~~~~~~~~~~~~~~~~~~~~~~~~~~~~~~~~~~~~~~~~~~~~~~~~~~~~~~~~~~
hskcnq5  SMRKSFDMGGETLLSVCPMVPK....DLGKSLSVQNLIRSTEELNIQLSGSESSGSRGSQ
hskcnq2  QSKENLDALNSCYAAVAPCAKVRPYIAEGESDTDSDLCTPCGPPPRSATGEGPFGDVGWA
hskcnq3  QDRDDYVFGPN...CGSSWMREKRYLAEGETDTDTDPFTPSGSMPLSSTGDGISDSVWTP
hskcnq1  ~~~~~~~~~~~~~~~~~~~~~~~~~~~~~~~~~~~~~~~~~~~~~~~~~~~~~~~~~~
```

FIG. 5C

```
hskcnq4  ------------------------------------------------------------
hskcnq5  DFYPKWRESKLFITDEEVGPEETETDTFDAAPQPAREAAFASDSLRTGRSRSSQSICKAG
hskcnq2  GPRK--------------------------------------------------------
hskcnq3  SNKPI-------------------------------------------------------
hskcnq1  ------------------------------------------------------------ hskcnq4  -------------
hskcnq5  ESTDALSLPHVKLK
hskcnq2  -------------
hskcnq3  -------------
hskcnq1  -------------
```

FIG. 6A

Human RNA Master Blot

TABLE 1

|   | 1 | 2 | 3 | 4 | 5 | 6 | 7 | 8 |
|---|---|---|---|---|---|---|---|---|
| A | whole brain | amygdala | Caudate nucleus | cerebellum | cerebral cortex | frontal lobe | hippocampus | medulla oblongata |
| B | occipital pole | putamen | substantia nigra | temporal lobe | thalamus | Subthalamic nucleus | spinal cord | |
| C | heart | aorta | Skeletal muscle | colon | bladder | uterus | prostate | stomach |
| D | testis | ovary | pancreas | pituitary gland | adrenal gland | thyroid gland | salivary gland | mammary gland |
| E | kidney | liver | small intestine | spleen | thymus | peripheral leukocyte | lymph node | bone marrow |
| F | Appendix | lung | trachea | placenta | | | | |
| G | fetal brain | fetal heart | fetal kidney | fetal liver | fetal spleen | fetal thymus | fetal lung | |
| H | yeast total RNA | yeast tRNA | E. coli rRNA | E. coli DNA | Poly r(A) | human $C_0 t$ DNA | human DNA | human DNA |

FIG. 6B

|   | 1 | 2 | 3 | 4 | 5 | 6 | 7 | 8 |
|---|---|---|---|---|---|---|---|---|
| A | • |   | • |   | • | • | • |   |
| B | • | • |   | • |   |   |   |   |
| C |   |   | • |   |   |   |   |   |
| D |   |   |   |   |   |   |   |   |
| E |   |   |   |   |   |   |   |   |
| F |   |   |   |   |   |   |   |   |
| G |   |   |   |   |   |   |   |   |
| H |   |   |   | • |   |   |   |   | hKCNQ5

Control

TEA 30 mM

1μA | 1sec

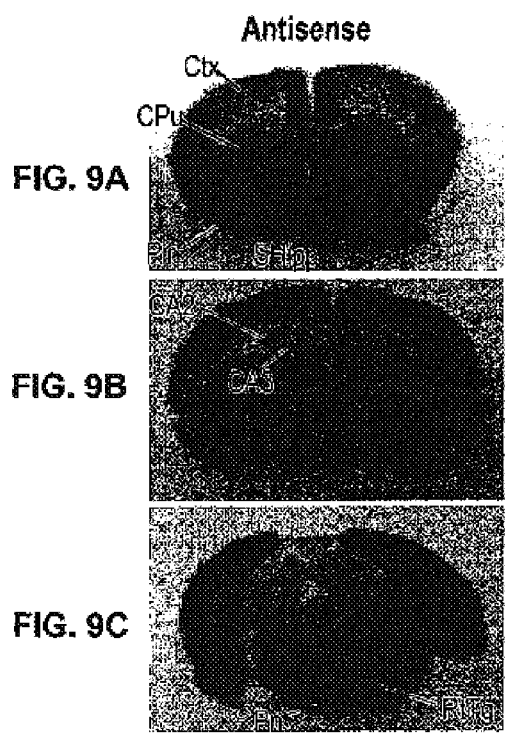 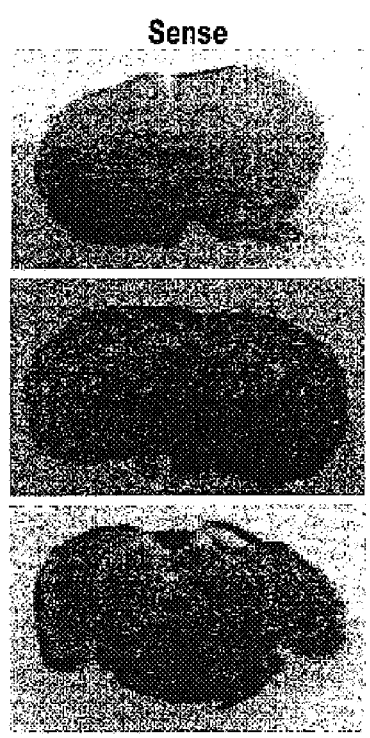
FIG. 9A
FIG. 9B
FIG. 9C
FIG. 9D
FIG. 9E
FIG. 9F

FIG. 10A
FIG. 10B
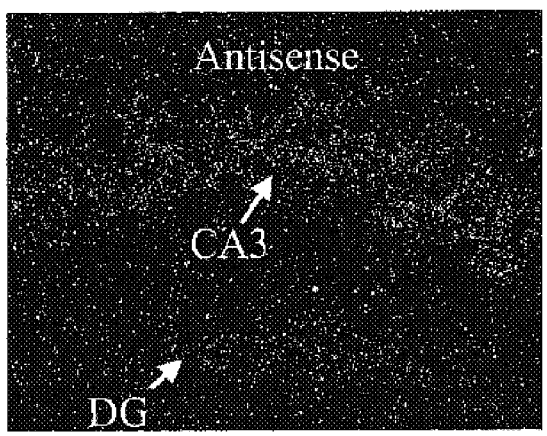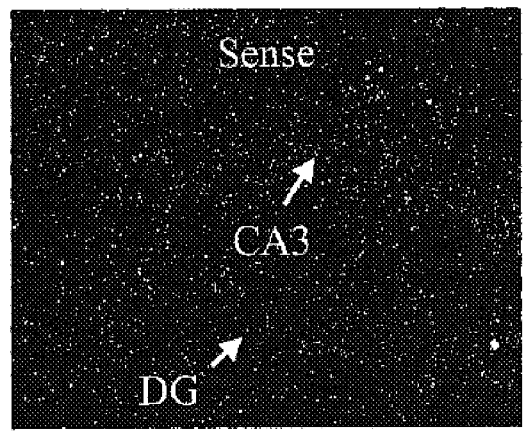

FIG. 12A
FIG. 12B
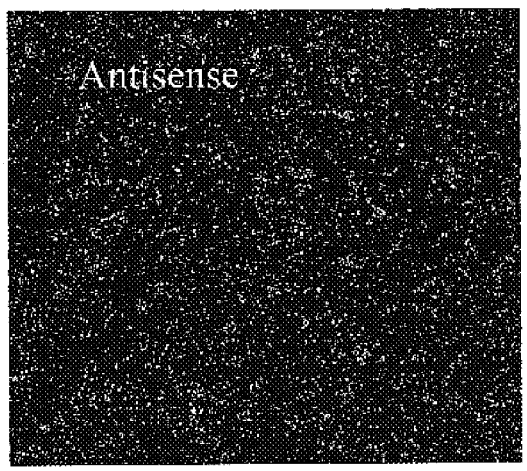
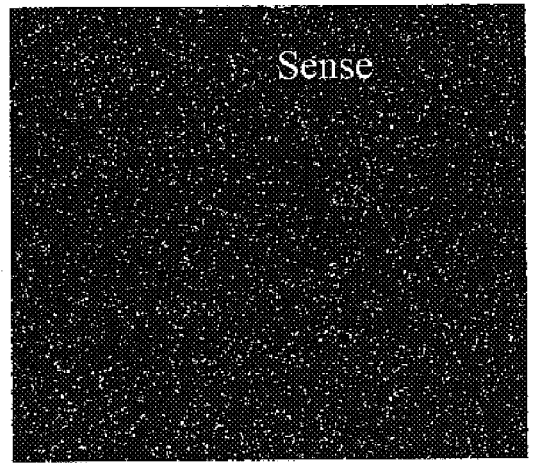

FIG. 13A
FIG. 13B
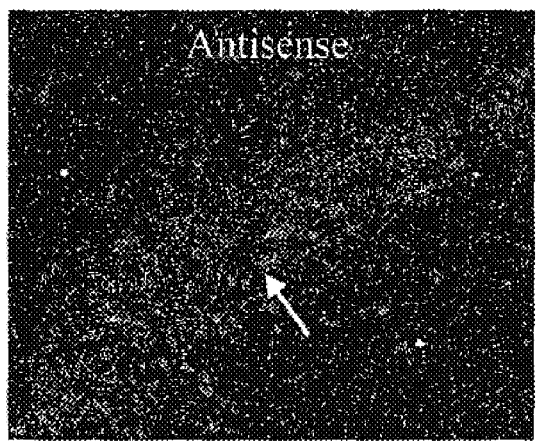
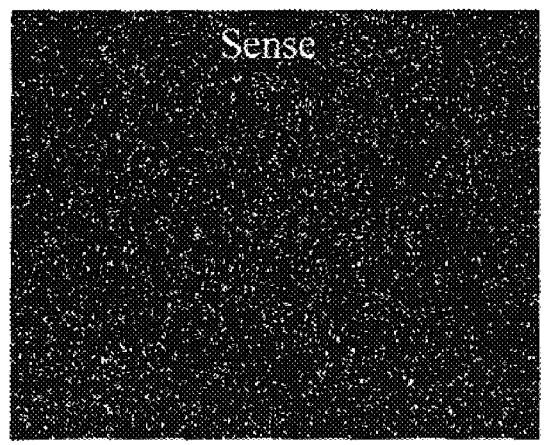

FIG. 15A
FIG. 15B
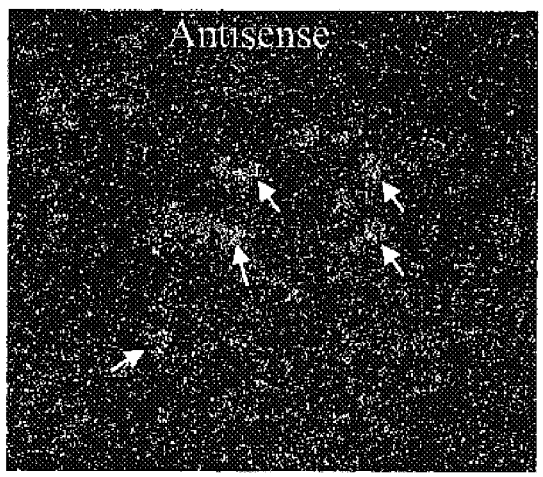
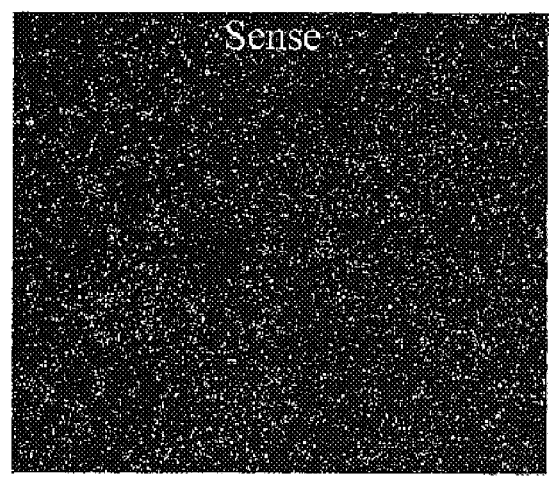

US 6,893,858 B2

HUMAN KCNQ5 POTASSIUM CHANNEL, METHODS AND COMPOSITIONS THEREOF

This application claims benefit of provisional patent application U.S. Ser. No. 60/207,389, filed May 26, 2000.

FIELD OF THE INVENTION

The present invention relates generally to the KCNQ family of potassium channels. More specifically, the present invention provides a new potassium channel polypeptide, KCNQ5, which was cloned and isolated from human tissue. Human KCNQ5 is found to be expressed primarily in brain and skeletal muscle. The present invention further provides methods for modulating the KCNQ5 potassium channel and assays for detecting channel modulators, which have use in the treatment of a variety of neurological, neurophysiological and neuropsychological conditions, disorders and diseases.

BACKGROUND OF THE INVENTION

Potassium channels are membrane-spanning proteins that generally act to hyperpolarize neurons. Physiological studies indicate that potassium currents are found in most cells and are associated with a wide range of functions, including the regulation of the electrical properties of excitable cells. Depending on the type of potassium channel, its functional activity can be controlled by transmembrane voltage, different ligands, protein phosphorylation, or other second messengers.

In the last decade, the cloning of potassium channels has resulted in the discovery of the molecular isolation and characterization of greater than 50 potassium channel genes and many of their associated regulatory subunits. More recently, a new family of potassium channel genes, the KCNQ gene family, has been described (N. A. Singh et al., 1998, *Nature Genet.*, 18:25–29; C. Charlier et al., 1998, *Nature Genet.*, 18:53–55; C. Biervert et al., 1998, *Science*, 279:403–406). The KCNQ family of potassium channels are voltage dependent potassium channels. They contain the voltage sensor and pore signature sequences characteristic of a 6 transmembrane potassium channel gene and have a longer carboxy-terminus than other known voltage-dependent potassium channels.

A remarkable aspect about the KCNQ1–4 gene family is that mutations in each channel are associated with a particular disease, including cardiac arrhythmias (KCNQ1), epilepsy (KCNQ2 and KCNQ3), and hearing loss (KCNQ4). The present invention provides a newly isolated, cloned and characterized member of the KCNQ family, called KCNQ5. Human KCNQ5 provides the art with an additional member of the KCNQ family of potassium channel proteins, isolated from a human source, for use in the methods and compositions described herein.

SUMMARY OF THE INVENTION

It is an object of the present invention to provide a novel isolated polynucleotide molecule encoding a novel potassium channel polypeptide referred to herein as KCNQ5, or hKCNQ5 (i.e., human KCNQ5). The present invention encompasses the amino acid sequence of the hKCNQ5 protein and the nucleic acid sequence encoding the hKCNQ5 protein. Also embraced by the present invention are variations in the hKCNQ5 nucleic acid sequence due to degeneracy in the genetic code.

The present invention provides for polynucleotide molecules which are at least about 70% identical to the polynucleotide sequence of the native hKCNQ5 sequence disclosed herein and set forth as SEQ ID NO:1. Preferably, the present invention provides: (a) a purified and isolated nucleic acid molecule encoding a KCNQ5 protein according to the present invention; (b) nucleic acid sequences complementary to (a); (c) nucleic acid sequences having at least 70% sequence identity, preferably at least 80% to at least 90%, more preferably at least 95%, and most preferably at least 98% sequence identity to (a); or (d) a fragment of (a) or (b) which will hybridize to (a) or (b) under low, moderately stringent and/or highly stringent conditions (described further herein), said fragment preferably comprising at least 15 nucleotides to 20 nucleotides (e.g., encoding at least 5 codons, more preferably at least about 7–15 codons), and more preferably encoding a functional or biologically active fragment of the hKCNQ5 polypeptide, such as the pore region (which spans about amino acid 191 to amino acid 209 of the KCNQ5 polypeptide sequence) or the S4 voltage sensor region (which spans about amino acid 265 to amino acid 285 of the KCNQ5 polypeptide sequence) (FIG. 5A).

It is another object of the present invention to provide an amino acid sequence which is at least about 70% to 80% identical to the hKCNQ5 polypeptide sequence disclosed herein and set forth as SEQ ID NO:2. Preferably, the present invention includes: (a) the amino acid sequence of the KCNQ5 protein of the present invention; and (b) amino acid sequences having at least 70% sequence identity, preferably at least 80%, more preferably at least 90%, more preferably at least 95%, and most preferably at least 98% sequence identity to (a).

It is yet a further object of the present invention to provide a novel KCNQ5 polynucleotide molecule, associated vectors, host cells, and methods of use. Preferably, the polynucleotide molecule is a DNA molecule. In accordance with the present invention, polynucleotide sequences having approximately 70% or greater identity to the hKCNQ5 sequence are preferred, preferably under moderate or high stringency conditions. Also preferred are nucleotide sequences that about 80% or more identical to the KCNQ5 polynucleotide sequence of SEQ ID NO:1.

Yet another object of the present invention is to provide nucleic acids obtained by PCR with degenerate oligonucleotide primers. The ordinarily skilled practitioner in the art can devise such primers based on the hKCNQ5 nucleic acid sequence and/or the consensus sequence(s) described herein using techniques known and practiced in the art. For example, PCR techniques are described in White et al., 1989, *Trends Genet.* 5:185–9.

Another object of the present invention is to provide expression vectors comprising a nucleic acid sequence coding for a KCNQ5 polypeptide, or fragment thereof, preferably a functional or biologically active fragment thereof; host cells containing such vectors; and polypeptides comprising the amino acid sequence of the KCNQ5 protein. Such polypeptides, or fragments thereof, may be isolated and purified employing conventional methodologies, following expression in the host cell. Preferably, the vector encodes a full-length KCNQ5 protein and the polypeptide is a full-length KCNQ5 protein. Preferred are frog (Xenopus) expression vectors, such as pSP64T or derivatives thereof (Melton et al., 1984, *Nucl. Acids Res.*, 12: 7057–70); mammalian cell expression vectors, such as pcDNA3 (available from Invitrogen); or bacterial cell expression vectors, such as pET-30 (available from Novagen or Promega).

Yet another object of the present invention is to provide host cells transformed with the above-described vectors.

Preferred are Xenopus oocytes, mammalian cells (e.g., HEK-293, CHO, L929), and bacterial cells (e.g., E. coli, especially BL21 (DE3), available from Novagen). Particularly preferred are HEK-293 cells deposited as ATCC Accession No. CRL-1573 (American Type Culture Collection, 10801 University Boulevard, Manassas Va. 20110-2209). The present invention also provides a method for producing a KCNQ5 polypeptide having the amino acid sequence as depicted in SEQ ID NO:2 by culturing a host cell under conditions suitable for the expression of the polypeptide, and recovering the polypeptide from the host cell culture.

It is another object of the present invention to provide methods for detecting nucleic acids that code for KCNQ5 proteins, as well as processes for detecting molecules that bind to and/or otherwise modulate (e.g., activate, up-regulate, increase, or inhibit, block, or down-regulate) the activity of the KCNQ5 protein. As used herein, "modulate" encompasses both channel openers/activators, and the like, as well as channel closers/inactivators/blockers, and the like.

A further object of the present invention is to provide methods of modulating KCNQ5 proteins, specifically methods of opening/activating or closing/inactivating/blocking KCNQ5 potassium channels. Moreover, the present invention encompasses a method of treating a disease or disorder, preferably, a neuroaffective disorder, such as a neurological, neurophysiological, or neuropsychological disease or disorder, by modulating the activity of the KCNQ5 protein. Thus, the present invention is directed to a treatment of an individual in need of such treatment for a condition that is mediated by a potassium channel, particularly, the KCNQ5 potassium channel, or for a condition that is mediated by the biological activity of human KCNQ5, comprising administering to the individual a potassium channel modulating compound in an amount effective to modulate the activity of the potassium channel as described herein.

Another object of the present invention is to provide methods for identifying compounds (e.g., small molecules, peptides, analogs, mimetics) that modulate the biological activity of a potassium channel, preferably the hKCNQ5 potassium channel, comprising: combining a candidate compound modulator of a potassium channel biological activity with the KCNQ5 potassium channel polypeptide having the amino acid sequence set forth in SEQ ID NO:2; and measuring an effect of the candidate compound modulator on the biological activity of the potassium channel polypeptide. According to the present invention, the potassium channel polypeptide may be expressed by a recombinant host cell.

It is a further object of the present invention to provide an antisense polynucleotide molecule comprising substantially the complement of the KCNQ5 nucleic acid sequence set forth in SEQ ID NO:1, or a biologically effective portion thereof. Also, in accordance with the present invention is provided a method for modulating, e.g., inhibiting or downregulating, the expression and/or activity of the KCNQ5 potassium channel polypeptide using the antisense polynucleotide molecule, comprising administering to an individual in need of such modulating an amount of the antisense molecule effect to modulate the expression and/or activity of the KCNQ5 potassium channel polypeptide.

Yet a further object of the present invention is to provide an antibody having specificity toward an isolated and purified KCNQ5 polypeptide, preferably the hKCNQ5 polypeptide, having the amino acid sequence as shown in SEQ ID NO:2, or an immunoreactive peptide fragment thereof.

Additional objects and advantages afforded by the present invention will be apparent from the detailed description hereinbelow.

DESCRIPTION OF THE FIGURES

The appended drawings of the figures are presented to further describe the invention and to assist in its understanding through clarification of its various aspects.

FIGS. 1A–1D show the coding sequence (i.e., cDNA) of human KCNQ5 from nucleotides 1 to 2694. (SEQ ID NO:1).

FIGS. 2A and 2B show the amino acid sequence (SEQ ID NO:2) of the human KCNQ5 polypeptide deduced from the coding sequence shown in FIGS. 1A–1D.

FIG. 3 shows an alternative splice exon of hKCNQ5, which is located between nucleotide positions 1143 and 1144 (SEQ ID NO:3) in the hKCNQ5 coding sequence.

FIGS. 4A and 4B show the 3' untranslated region (3' UTR), (SEQ ID NO:4) of the hKCNQ5 sequence.

FIGS. 5A–5C show multiple sequence alignments of the human KCNQ channel family members. The blackened areas represent identical amino acids among all 5 family members and the gray highlighted amino acids represent similar amino acids among the KCNQ family members. As shown in FIGS. 5A–5C: human KCNQ1 (SEQ ID NO:28); human KCNQ2 (SEQ ID NO:29); human KCNQ3 (SEQ ID NO:30); human KCNQ4 (SEQ ID NO:31); human KCNQ5 (FIGS. 2A/2B and SEQ ID NO:2).

FIGS. 6A and 6B show mRNA localization of hKCNQ5 by dot blot analysis. Human KCNQ5 is observed in whole brain and brain subregions, including caudate nucleus, cerebellum, hippocampus, cerebral cortex, frontal lobe, occipital pole, putamen and temporal lobe, as well in skeletal muscle. FIG. 6A presents Table 1, a Human RNA Master Blot, showing type and position of poly $A^+$ RNAs and controls that are spotted or dotted on the membrane. FIG. 6B shows the actual dot blot wherein a high level of hybridization of hKCNQ5 probe has occurred specifically in spots on the membrane occupied by mRNA samples from human tissues as follows: 1A: whole brain; 3A: caudate nucleus; 5A: cerebral cortex; 6A: frontal lobe; 7A: hippocampus; 1B: occipital lobe; 2B. putamen; 4B: temporal lobe; 3C: skeletal muscle; and 1G: fetal brain (slight).

FIGS. 9A–9E show the results of in situ hybridization studies using KCNQ5 antisense and sense probes (Example 3) on brain sections. Specifically shown are autoradiograms of representative coronal sections of rat brain showing positive in situ hybridization signal with antisense (FIGS. 9A–9C) or sense (control), (FIGS. 9D–9F) riboprobes for human KCNQ5 mRNA. The abbreviations in FIG. 9A are as follows: Ctx: cortex; CPu: caudate putamen; Pir: piriform cortex; SHipp: septohippocampal nucleus. The abbreviations in FIG. 9B are as follows: CA2 and CA3 are regions of the hippocampus. The abbreviations in FIG. 9C are as follows: Pn: pontine nuclei; RtTg: reticulotegmental nuclei of the pons.

FIGS. 10A and 10B depict dark field images of emulsion dipped slides showing the expression of KCNQ5 mRNA in the hippocampus. FIG. 10A: Hybridization with the antisense riboprobe shows positive signal in the CA3 region, which is absent in the dentate gyrus (DG). FIG. 10B: The signal is absent with the sense riboprobe.

FIGS. 12A and 12B depict dark field images of emulsion dipped slides showing the expression of KCNQ5 mRNA in the cortex. Hybridization with the antisense riboprobe shows a weak, diffuse positive signal with clusters over individual neurons (FIG. 12A), which is absent with the sense riboprobe (FIG. 12B).

FIGS. 13A and 13B depict dark field images of emulsion dipped slides showing the expression of KCNQ5 mRNA in the piriform cortex. Hybridization with the antisense riboprobe shows a weak-moderate signal (FIG. 13A), which is absent with the sense riboprobe (FIG. 13B).

FIGS. 15A and 15B depict dark field images of emulsion dipped slides showing the expression of KCNQ5 mRNA in the reticulotegmental nucleus of the pons. Hybridization with the antisense riboprobe shows a weak-moderate signal, with clusters of grains over individual neurons (FIG. 15A), which is absent with the sense riboprobe (FIG. 15B).

DETAILED DESCRIPTION OF THE INVENTION

Figure 7:
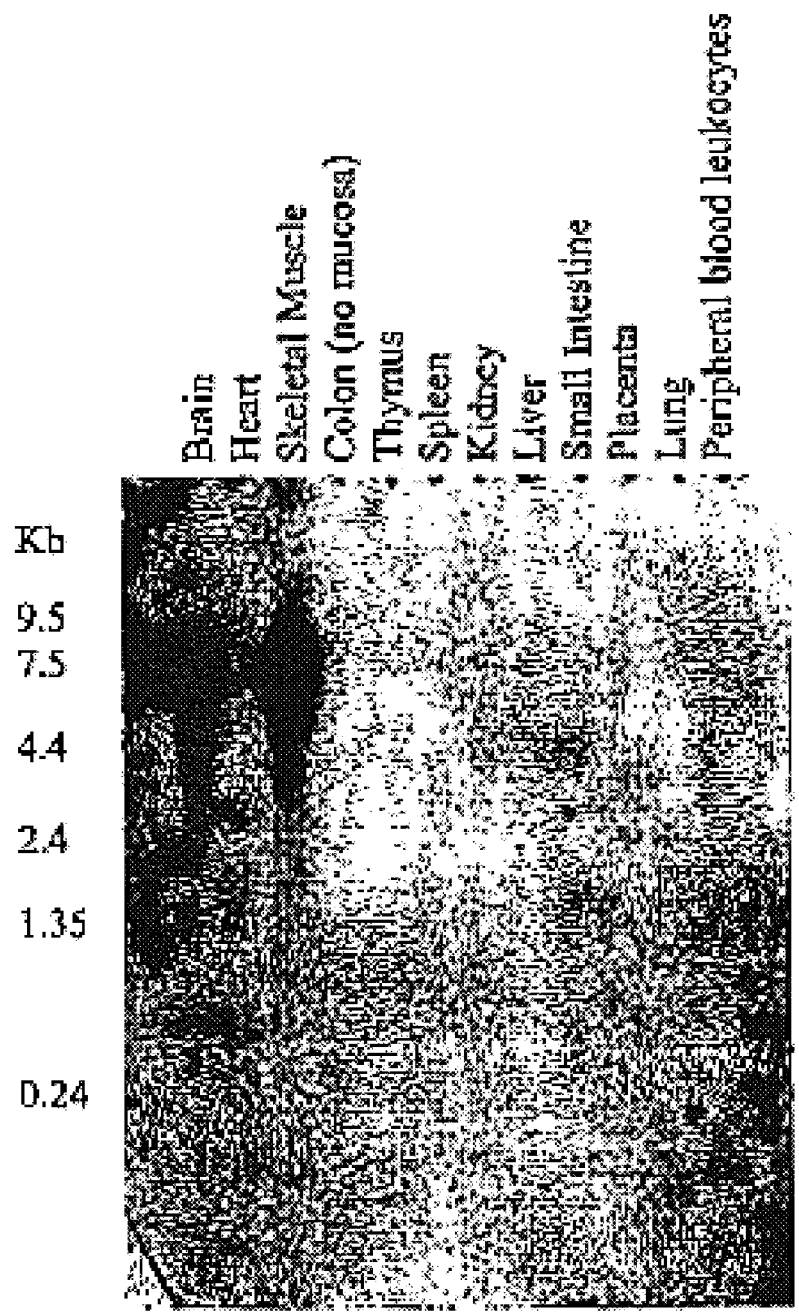
FIG. 7 shows a Northern blot analysis in which hKCNQ5 mRNA is found to be localized to skeletal muscle and brain. A single transcript of approximately 7.5 Kb is shown. The lanes contain mRNA from the following tissues, left to right: brain, heart, skeletal muscle, colon (no mucosa), thymus, spleen, kidney, liver, small intestine, placenta, lung and peripheral blood leukocytes (PBL). Molecular weight markers (kd) are shown in the leftmost lane of the blot: 9.5, 7.5, 4.4, 2.4, 1.35 and 0.24.

The present invention provides an isolated and purified polynucleotide encoding a new human potassium channel polypeptide, called human KCNQ5 (hKCNQ5). The invention relates to the isolation, cloning and sequencing the hKCNQ5 potassium channel gene from human tissue. A newly discovered member of the KCNQ family of potassium channels, hKCNQ5 has a limited tissue distribution and can be used in the identification and characterization of modulators of this potassium channel. Such modulators can affect channel activity/function, particularly with respect to neuroaffective diseases, or neurological, neurophysiological, or neuropsychological diseases, conditions and disorders, preferably those affecting or influencing brain and/or skeletal muscle.

Definitions

Unless otherwise defined, the technical and scientific terms as used herein have the same meanings as are commonly understood by persons skilled in the art to which the present invention pertains. The following definitions apply to the terms used throughout this specification, unless otherwise defined in specific instances:

Biological activity or functional activity refers to the ability to allow transmembrane potassium ion flow and/or transport, or to regulate transmembrane potassium ion flow and/or transport, or to the ability of a subunit to bind to another subunit, ligand, or cofactor, and/or to otherwise modulate the pharmacological activity of a potassium channel.

Cloning refers to the isolation of a particular gene from genetic material, for example a genome, genomic library, or cDNA library into a plasmid or other vector.

Purified refers to molecules, either polynucleotides or amino acids (polypeptides and proteins) that are removed from their natural environment and isolated or separated from at least one other component with which they are naturally associated. Polynucleotides include nucleic acids, namely, DNA, cDNA, genomic DNA, RNA, synthetic forms and mixed polymers, both sense and antisense strands, and may be chemically or biochemically modified, or may contain non-natural or derivatized nucleotide bases, as will be readily appreciated by those skilled in the art.

In general, a polypeptide refers to a polymer of amino acids and its equivalent, and does not refer to a specific length of the product. Peptides, oligopeptides and proteins may be termed polypeptides. The terms polypeptide and protein are often used interchangeably herein. The term polypeptide also does not refer to, or exclude, modifications of the polypeptide, e.g., glycosylation, acetylation, phosphorylation and the like. Included in the definition of KCNQ5 polypeptides are, for example, polypeptides containing one or more analogs of an amino acid (including, for example, unnatural amino acids, and the like), polypeptides with substituted linkages, as well as other modifications known in the art, both naturally and non-naturally occurring.

The term hybridization refers to any process by which a strand of nucleic acid binds with a complementary strand through base pairing. A hybridization complex refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_o t$ or $R_o t$ analysis) or between one nucleic acid sequence present in solution and another nucleic acid sequence immobilized on a solid support (e.g., membranes, filters, chips, pins or glass slides to which cells have been fixed in situ hybridization).

The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single stranded molecules. The degree of complementarity between nucleic acid strands has significant effects on the efficiency and strength of hybridization between nucleic acid strands. This is of particular importance in amplification reactions, which depend upon binding between nucleic acids strands.

Homology refers to a degree of complementarity. There may be partial homology, or complete homology, which is equivalent to identity. A partially complementary sequence is one that at least partially inhibits an identical sequence from hybridizing to a target nucleic acid; it can be referred to using the functional term "substantially homologous". The inhibition of hybridization of a completely complementary sequence to a target sequence can be examined using a hybridization assay (e.g., Southern or Northern blot, solution hybridization, and the like) under conditions of low stringency. A substantially homologous sequence or probe will compete for and inhibit the binding (i.e., the hybridization) of a completely homologous sequence or probe to the target sequence under conditions of low stringency.

The terms "identical" or "percent identity" in the context of two or more nucleic acid or amino acid sequences, refer to two or more sequences or subsequences that are the same, or that have a specified percentage of amino acid residues or nucleotides that are the same (e.g., 60% or 65% identity, preferably, 70%–95% identity, more preferably, >95% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably the described identity exists over a region that is at least about 15 to 25 amino acids or nucleotides in length, more preferably, over a region that is about 50 to 100 amino acids or nucleotides in length.

Those having skill in the art will know how to determine percent identity between/among sequences using, for example, algorithms such as those based on the CLUSTALW computer program (J. D. Thompson et al., 1994, *Nucleic Acids Research*, 2(22):4673–4680), or FASTDB, (Brutlag et al., 1990, *Comp. App. Biosci.*, 6:237–245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul et al., 1977, *Nuc. Acids Res.*, 25:3389–3402 and Altschul et al., 1990, *J. Mol. Biol.*, 215:403–410). The BLASTN program for nucleic acid sequences uses as defaults a wordlength (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff & Henikoff, 1989, *Proc. Natl. Acad. Sci., USA*, 89:10915) uses alignments (B) of 50, expectation (E) of 10, M=5, N=4, and a comparison of both strands.

As known in the art, numerous equivalent conditions may be employed to comprise either low or high stringency conditions. Factors such as the length and nature (DNA, RNA, base composition –G+C content) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The phrase stringency of hybridization refers to conditions under which polynucleic acid hybrid molecules are stable. As known to those skilled in the art, the stability of a hybrid is reflected in the melting temperature ($T_m$) of the hybrids. Also as is appreciated by the skilled practitioner, $T_m$ can be approximated by the formulas as known in the art, depending on a number of parameters, such as the length of the hybrid or probe in number of nucleotides, or hybridization buffer ingredients and conditions (See, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994–1995, Suppls. 26, 29, 35 and 42; pp. 2.10.7–2.10.16; G. M. Wahl and S. L. Berger (1987; *Methods Enzymol.* 152:399–407); and A. R. Kimmel, 1987; *Methods of Enzymol.* 152:507–511). As a general guide, $T_m$ decreases approximately 1° C. −1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, generally relates to such washing conditions.

Thus, for example, high stringency refers to conditions that permit hybridization of those nucleic acid sequences that form stable hybrids in 0.018M NaCl at 65° C. (i.e., if a hybrid is not stable in 0.018M NaCl at 65° C., it will not be stable under high stringency conditions). High stringency conditions can be provided, for instance, by hybridization in 50% formamide, 5×Denhart's solution, 5×SSPE (1×SSPE buffer comprises 0.15 M NaCl, 10 mM $Na_2HPO_4$, 1 mM EDTA), (or 1×SSC buffer containing 150 mM NaCl, 15 mM $Na_3$ citrate.2 $H_2O$, pH 7.0), 0.2% SDS at 42° C., followed by washing in 1×SSPE (or SSC) and 0.1% SDS at a temperature of at least about 42° C., preferably about 55° C., more preferably about 65° C.

Moderate stringency refers, for example, to conditions that permit hybridization in 50% formamide, 5×Denhart's solution, 5×SSPE (or SSC), 0.2% SDS at 42° C., followed by washing in 0.2×SSPE (or SSC) and 0.2% SDS at a temperature of at least about 42° C., preferably about 55° C., more preferably about 65° C.

Low stringency refers, for example, to conditions that permit hybridization in 10% formamide, 5×Denhart's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate and high stringency hybridization/washing conditions may be varied using a variety of ingredients, buffers and temperatures well known to and practiced by the skilled practitioner.

Multi-copy plasmid refers to a plasmid having greater than one copy present in a cell (typically 10 to 30 copies).

Northern blotting refers to a method of identifying particular RNA fragments, particularly mRNA, by hybridization with a complementary nucleic acid, typically a cDNA or an oligonucleotide. Oligonucleotides or oligomers refer to a nucleic acid sequence, preferably comprising contiguous nucleotides, of at least about 6 nucleotides to about 60 nucleotides, preferably at least about 8 to 10 nucleotides in length, more preferably at least about 12 nucleotides in length e.g., about 15 to 35 nucleotides, or about 15 to 25 nucleotides, or about 20 to 35 nucleotides, which can be typically used in PCR amplification assays, hybridization assays, or in microarrays. It will be understood that the term oligonucleotide is substantially equivalent to the terms primer, probe, or amplimer, as commonly defined in the art. It will also be appreciated by those skilled in the pertinent art that a longer oligonucleotide probe, or mixtures of probes, e.g., degenerate probes, can be used to detect longer, or more complex, nucleic acid sequences, for example, genomic DNA. In such cases, the probe may comprise at least 20–200 nucleotides, preferably, at least 30–100 nucleotides, more preferably, 50–100 nucleotides.

Open reading frame, or "ORF", refers to a DNA sequence containing a series of nucleotide triplets coding for amino acids and typically lacking any termination codons.

Plasmid refers to cytoplasmic, autonomously replicating DNA elements, which are either exogenously added to, or endogenously present in, microorganisms.

Promoter refers to a region on DNA at which RNA polymerase binds and initiates transcription.

Southern blotting refers to a method of identifying particular DNA fragments by hybridization with a complementary nucleic acid, typically a cDNA or an oligonucleotide.

Modulation refers to the capacity to either enhance, augment, activate, or decrease, diminish, or inhibit a functional, biophysical, or biological activity of the KCNQ5 potassium ion channel. Modulation or regulation of biological activity refers to binding, blocking, inhibiting, antagonizing, repressing, neutralizing, or sequestering, either completely or partially, a KCNQ5 potassium channel protein, including, but not limited to, the human KCNQ5 channel described herein, as well as up-regulating, agonizing, increasing, or activating the KCNQ5 potassium channel by a compound that can be identified by the methods described herein. Inhibitors are compounds that inhibit, decrease, block, prevent, delay activation, inactivate, desensitize, or down-regulate the ion channel, or speed up or enhance deactivation. Activators are compounds that increase, open, activate, facilitate, enhance activation, sensitize, or up-regulate channel activity, or delay or slow inactivation.

Assays for inhibitors and activators include, for example, expressing a recombinantly produced KCNQ5 potassium channel in cells or cell membranes and then measuring the flux of potassium ions through the channel, either directly or indirectly. Alternatively, cells expressing endogenous KCNQ5 channels can be used in such assays. To examine the extent of inhibition, samples or assays comprising a KCNQ5 potassium channel are treated with a potential activator or inhibitor compound and are compared with control samples without the test compound. For example, control samples (untreated with test compounds) are assigned a relative potassium ion channel activity value of 100%. Inhibition of a KCNQ5 potassium ion channel is achieved when the KCNQ5 channel activity value relative to the control is about 90%, preferably about 50%, more preferably about 25 to 0%. Activation of an ion channel is achieved when the ion channel activity value relative to the control is greater than 100% to 110%, preferably, 150%, more preferably, at least 200–500% or higher, most preferably, at least 1000%, or higher.

A biologically active fragment refers to portions of the KCNQ5 potassium channel polypeptide, such as peptides, that have been truncated with respect to the N- or C-termini, or both; or to the corresponding 5' or 3' end, or both, of the corresponding polynucleotide coding region. The portions or fragments perform essentially the same biological function, or encode peptides which perform essentially the same function in substantially the same way as the KCNQ5 polypeptide. Biologically active can also refer to the activity of a homologue, variant, or analog entity that has structural, regulatory, or biochemical functions that are essentially the same as the naturally occurring, or recombinantly-expressed, entire KCNQ5 polypeptide entity.

For definitions of other terms in this specification, F. Sherman et al., *Laboratory Course Manual for Methods in Yeast Genetics*, Cold Spring Harbor Laboratory, Cold Spring Harbor, N.Y. (1987) and Lewin, B., Genes IV, Oxford University Press, Oxford (1990), serve as guides.

In one aspect of the present invention, the novel hKCNQ5 protein, which is highly likely to be involved in neurotransmission and neurophysiological functions, serves as a target for identifying modulators of the potassium channel. KCNQ5 modulators would be useful as diagnostic agents, therapeutic agents and/or in the treatment of central nervous system-associated diseases, neurological diseases, conditions and physiological disorders associated with or linked to the opening or blocking of the KCNQ5 potassium channel, including, but not limited to, acute and chronic pain, migraine headaches, acute stroke, cognitive disorders, dementia, vascular dementia, trauma, epilepsy, seizures, affective disorders, amyelotrophic lateral sclerosis (ALS), multiple sclerosis (MS), Parkinson's Disease, Parkinson's-like motor disorders, and neurophysiological, or neuropsychological disorders including anxiety disorders, phobias, depression, Pick's disease, psychosis, bipolar disorders, sleep disorders, compulsive behavior, addiction, and eating disorders, ataxia, myokymia, Alzheimer's disease, age-associated memory loss and other cognitive disorders, learning deficiencies, motor neuron diseases, spinal cord damage, tremor seizures, convulsions, and the like. Openers of the hKCNQ5 potassium channel are of particular interest for increasing the flow of ions across a cell membrane and affecting one or more of the above-listed conditions or diseases, for example, migraine, pain, or anxiety disorders.

The novel KCNQ5 potassium channel protein described herein can play a crucial role in modulating synaptic transmission and electrical excitability in the brain. Modulating the function of the KCNQ5 protein of the present invention may have significant implications in cognitive disorders (e.g., learning and memory), behavioral disorders (e.g., anxiety and/or depression), psychiatric conditions (e.g., bipolar disorders, schizophrenia), neurodegenerative diseases (e.g., Alzheimer's disease, Parkinson's disease), developmental disorders (e.g., mental retardation), as well as in other physiological and/or neurophysiological or neuropsychological problems or disorders, such as asthma, migraine headaches, seizures, i.e., epileptic seizures, stroke, neuronal cell death, chronic and acute pain, and brain tumors.

In another embodiment of the invention, the KCNQ5 nucleic acid provided herein, or antisense nucleic acids complementary to the KCNQ5 nucleic acid sequence, or portions thereof, may be utilized as therapeutic or diagnostic agents. For therapy involving KCNQ5 polynucleotide molecules, the nucleic acids may be incorporated into vectors and/or formulated as described hereinbelow and as known and practiced in the art.

In addition, persons skilled in the art can use the KCNQ5 polypeptides and nucleic acids of this invention to prepare antibodies, vectors, cells and/or and cell lines. All of these are useful in assays for the identification of KCNQ5 protein modulators, as well as in therapeutic, screening and diagnostic applications.

Further, KCNQ5 protein modulators can be administered to various mammalian species, such as monkeys, dogs, cats, mice, rats, humans, etc. By known methods, persons skilled in the pharmaceutical art can incorporate KCNQ5 protein modulators in a conventional systemic dosage form, such as a tablet, capsule, elixir or injectable formulation. The above dosage forms will also include any necessary physiologically acceptable carrier material, excipient, lubricant, buffer, antibacterial, bulking agent (such as mannitol), anti-oxidants (ascorbic acid or sodium bisulfite) or the like, as further described infra.

Cloning and Isolation of KCNQ5 Nucleic Acid

In one aspect of the present invention, the cloning, sequencing and functional expression of a full-length human cDNA clone of hKCNQ5, preferably the hKCNQ5 nucleic acid sequence set forth in SEQ ID NO:1 and FIGS. 1A–1D are provided. A DNA clone comprising the full-length human KCNQ5 cDNA (in pcDNA3.1) of the present invention was deposited with the American Type Culture Collection (ATCC) (10801 University Blvd., Manassas, Va. 20110-2209) on May 26, 2000, ATCC Accession Number PTA-1924. The deposit(s) referred to herein will be maintained under the terms of the Budapest Treaty on the International Recognition of the Deposit of Microorganisms for purposes of Patent Procedure. These deposits are provided merely as convenience to those of skill in the art and are not an admission that a deposit is required under 35 U.S.C. 112. The sequence of the polynucleotides contained in the deposited materials, as well as the amino acid sequence of the of the polypeptides encoded thereby, are incorporated herein by reference and are controlling in the event of any conflict with any description of sequences herein. A license may be required to make, use or sell the deposited materials, and no such license is hereby granted.

KCNQ5 nucleic acid can be obtained by known methods through the use of the described human KCNQ5 polynucleotide sequence of the present invention. For example, methods such as Southern and Northern blotting, Western immunoblotting, chemical synthesis, synthesis by polymerase chain reaction (PCR) from primers obtainable from SEQ ID NO:1, FIGS. 1A–1D and as described herein, expression cloning; and subtractive cDNA cloning are all available to the skilled practitioner for use in obtaining KCNQ5 derivable from other animal sources, including human and non-human mammals.

The nucleic acids encoding the hKCNQ5 protein of the present invention can be modified to prepare useful mutations. For example, one may modify the sequence to provide additional restriction endonuclease recognition sites in the nucleic acid. Such mutations may be silent or may change the amino acid encoded by the mutated codon. Moreover, modified nucleic acids can be prepared, for example, by mutating the nucleic acid coding for hKCNQ5 to result in deletion, substitution, insertion, inversion or addition of one or more amino acids in the encoded polypeptide. For methods of site-directed mutagenesis, see Taylor, J. W. et al., 1985, *Nucl. Acids Res.*, 13, 8749–64 and Kunkel, J. A., 1985, *Proc. Natl. Acad. Sci. U.S.A.* 82: 482–92. In addition, kits for site-directed mutagenesis are available from commercial vendors (e.g., BioRad Laboratories, Richmond, Calif.; Amersham Corp., Arlington Heights, Ill.). For disruption, deletion and truncation methods, see Sayers, J. R. et al., 1988, *Nucl. Acids Res.*, 16: 791–800.

The present invention also embraces modified nucleic acids, including (1) alternative splice exon variants, e.g., SEQ ID NO:3; (2) allelic variants; and (3) chimeric potassium channels in which the fusion construct comprises a KCNQ5 modulatory site. Such modified nucleic acids can be obtained by persons of ordinary skill in the art using the sequences provided herein. Accordingly, the KCNQ5 nucleotide sequence of the present invention may be molecularly engineered to alter the coding sequence, so as to advantageously modify the cloning, processing and/or expression of the gene product. For example, mutations may be introduced into the sequence using techniques that are well-known in the art and as described supra, e.g., site-directed mutagenesis to insert one or more new restriction sites, to alter glycosylation patterns, or to change codon preference or usage, to mention a few.

Also contemplated within the scope of the present invention are alleles of the human KCNQ5 protein described herein. As understood by those in the art, an allele or allelic sequence is an alternative form of the potassium channel described herein. Alleles result from nucleic acid mutations and mRNA splice-variants which produce polypeptides whose structure or function may or may not be altered. Any given gene may have none, one, or many, allelic forms. Common mutational changes which give rise to alleles are generally ascribed to natural deletions, additions, or substitutions of amino acids. Each of these types of changes may occur alone, or in combination with the others, one or more times in a given nucleic acid sequence.

In a particular aspect, the cloning of hKCNQ5 of the present invention involved the isolation of molecular clones as specifically described in Example 1 herein, which were sequenced and analyzed by searching the NCBI database (i.e., GenBank) for sequence homologies at a level of between about 35–45%. The results showed greater than about 40% homology with the known KCNQ genes within the databases. In addition, several of the isolated clones were aligned with each other in order to determine start and stop sequence codons. Although none of the individual clones appeared to comprise full length sequence, they did have substantial open reading frames. Several of the isolated clones were found to contain the 5' ATG start codon and others contained the 3' TAA stop codon. The alignment of all of the clone sequences generated a full length open reading frame of 2694 nucleotides. The full length DNA coding region of hKCNQ5 according to this invention is shown in FIGS. 1A–1D and is set forth in SEQ ID NO:1.

Hydropathy analysis indicated the presence of 6 membrane spanning domains and one pore region. The hKCNQ5 amino acid sequence (SEQ ID NO:2) revealed a KCNQ5 protein having two distinguishing features that are characteristics of potassium channel genes; namely, 1) the signature 'Gly-Tyr-Gly' pore sequence, and 2) alternating charged residues (Arg-Arg-Glu-Arg) in the S4 membrane-spanning domain, indicative of a voltage sensor.

One of the isolated clones contained an alternative splice exon at nucleotide 1143 encoding a 7 amino acid insert (SEQ ID NO:3), FIG. 3. In addition, a long 3' untranslated sequence (3' UTR), (SEQ ID NO:4), was isolated and is shown in FIGS. 4A and 4B.

Using the GCG pileup program (Feng and Doolittle, 1987, *J. Mol. Biol.*, 25:351–360), the alignment between the various human KCNQ potassium channel proteins and hKCNQ1–5 was generated and is shown in FIGS. 5A–5C. The blackened areas represent identical amino acids among all 5 family members and the gray highlighted amino acids represent similar amino acids. Overall, the homology among the KCNQ family members shows between about 40–50% identity, with higher homology (e.g., about 60%) in the membrane-spanning domains and the pore regions.

Expression Vectors

The present invention further encompasses expression vectors which comprise all or a portion of a nucleotide sequence encoding the hKCNQ5 protein/polypeptide described herein, or peptides thereof. Preferably, the expression vectors comprise all or a portion of the nucleic acid sequence as shown in SEQ ID NO:1.

Expression vectors are usually plasmids, but the invention includes other vector forms, such as viral vectors, as well as vectors that serve equivalent functions and become known in the art subsequently hereto. A person skilled in the art may also stably integrate a sequence encoding the KCNQ5 protein into the chromosome of an appropriate host cell using methods practiced in the art.

Expression vectors typically contain regulatory elements capable of affecting expression of the KCNQ5 protein. These regulatory elements can be heterologous or native KCNQ5 elements. Typically, a vector contains an origin of replication, a promoter, and a transcription termination sequence. The vector may also include other regulatory sequences, including mRNA stability sequences, which provide for stability of the expression product; secretory leader sequences, which provide for secretion of the expression product; environmental feedback sequences, which allow expression of the structural gene to be modulated (e.g., by the presence or absence of nutrients or other inducers in the growth medium); marking sequences, which are capable of providing phenotypic selection in transformed host cells; restriction sites, which provide sites for cleavage by restriction endonucleases; and sequences which allow expression in various types of host cells, including prokaryotic cells, yeast, fungi, plant cells, insect cells, mammalian cells, including human cells and non-human animal cells, and cells of higher eukaryotes.

As will be appreciated by the skilled practitioner, expression vectors comprise a nucleic acid sequence encoding at least one KCNQ5 polypeptide, as described herein, operably linked to at least one regulatory sequence or element. Operably linked is intended to mean that the nucleotide acid sequence is linked to a regulatory sequence in a manner which allows expression of the nucleotide sequence. Regulatory sequences are known in the art and are selected to direct expression of the desired protein in an appropriate host cell. Accordingly, the term regulatory sequence includes promoters, enhancers and other expression control elements (see D. V. Goeddel, 1990, *Methods Enzymol.*, 185:3–7). It should be understood that the design of the expression vector may depend on such factors as the choice of the host cell to be transfected and/or the type of protein desired to be expressed.

Vectors can contain one or more replication and inheritance systems for cloning or expression, one or more markers for selection in the host, e.g. antibiotic resistance, and one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

An expression vector according to this invention is at least capable of directing the replication, and preferably the expression, of the nucleic acids and protein of this invention. Suitable origins of replication include, for example, the Col E1, the SV4O viral and the M13 origins of replication. Suitable promoters include, for example, the cytomegalovirus (CMV) promoter, the lacZ promoter, the gal10 promoter and the *Autographa californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Examples of selectable markers include neomycin, ampicillin, and hygromycin resistance and the like. Specifically-designed vectors allow the shuttling of DNA between different host cells, such as bacteria-yeast, or bacteria-animal cells, or bacteria-fungal cells, or bacteria invertebrate cells.

KCNQ5 protein-encoding DNA of the present invention may be inserted into several commercially available vectors. Nonlimiting examples include plasmid vectors compatible with mammalian cells, such as pUC, pBluescript (Stratagene, La Jolla, Calif.), pET (Novagen, Inc., Madison, Wis.), pREP (Invitrogen Corp.), pcDNA3 (Invitrogen), pCEP4 (Invitrogen), pMC1neo (Stratagene), pXT1 (Stratagene), pSG5 (Stratagene), EBO-pSV2-neo (ATTC No. 37593), pBPV-1 (8-2) (ATCC No. 37110), pdBPV-MMTneo(342-12) (ATCC No. 37224), pRSVgpt (ATCC No. 37199), pRSVneo (ATCC No. 37198), pSV2-dhfr (ATCC No. 37146), pUCTag (ATCC No. 37460), IZD35 (ATCC No. 37565), pLXIN and pSIR (Clontech) and pIRES-EGFP (Clontech). Baculovirus vectors such as pBlueBac, BacPac™ Baculovirus Expression System (CLONTECH), and MaxBac™ Baculovirus Expression System, insect cells and protocols (Invitrogen) are available commercially and may also be used to produce high yields of biologically active protein. (See also, Miller, L. A. et al., 1993, *Curr. Op. Genet. Dev.*, 3:97 and O'Reilly, D. R. et al., *Baculovirus Expression Vectors: A Laboratory Manual*, p.127. In addition, prokaryotic vectors such as pcDNA2; and yeast vectors such as pYes2 are nonlimiting examples of other vectors suitable for use with the present invention. For vector modification techniques, see J. Sambrook et al., 1989, *Molecular Cloning: A Laboratory Manual*, Second Edition, Cold Spring Harbor Laboratory, Cold Spring Harbor, N.Y.

Host Cells

Host cells containing an expression vector that comprises a nucleic acid sequence encoding the KCNQ5 protein of the present invention can be cultured under conditions suitable for the expression and recovery of the expressed protein, e.g., from cell membranes or cell lysates, using methods known and practiced by those in the art. The host cells preferably contain an expression vector which comprises all or a portion of the DNA sequence having the nucleotide sequence substantially as shown in SEQ ID NO:1, particularly the KCNQ5 coding region thereof. Suitable host cells include both prokaryotic cells (e.g., *E. coli* strains HB101, DH5a, XL1 Blue, Y1090 and JM101), plant cells, fungal cells, and eukaryotic cells. Eukaryotic recombinant host cells are preferred. Examples of eukaryotic host cells include, but are not limited to, yeast, e.g., *S. cerevisiae* cells, cell lines of human, bovine, porcine, monkey, and rodent origin, as well as insect cells, including but not limited to, *Spodoptera frugiperda* insect cells and Drosophila-derived insect cells. Mammalian species-derived cell lines suitable for use and commercially available include, but are not limited to, L cells, CV-1 cells, CHO cells, (CHO-K1, ATCC CCL 61), COS-1 cells (ATCC CRL 1650), COS-7 cells (ATCC CRL 1651), HEK 293 cells, human skin fibroblasts, 3T3 cells (ATCC CCL 92), HeLa cells (ATCC CCL 2), C127I (ATCC CRL 1616), BS-C-1 (ATCC CCL 26) and MRC-5 (ATCC CCL 171).

The expression vectors may be introduced into host cells by various methods known in the art. Exemplary, yet nonlimiting, methods include transfection by calcium phosphate precipitation, electroporation, liposomal fusion/lipofection, transformation, transduction, protoplast fusion, direct DNA injection, nuclear injection, microparticle (e.g., colloidal gold) bombardment and viral or phage infection. The host cells are then cultured under conditions permitting expression of large amounts of KCNQ5 protein. Preferably, the cells containing expression vectors and expressing the KCNQ5 protein are clonally propagated and individually analyzed to determine the level of novel KCNQ5 potassium channel production.

Recombinant host cells expressing the KCNQ5 protein can be identified by any of six general and nonlimiting approaches: (1) DNA-DNA hybridization with probes complementary to the sequence encoding KCNQ5 protein (Southern blotting); (2) detection of marker gene functions, such as thymidine kinase activity, resistance to antibiotics, and the like (A marker gene can be placed in the same plasmid as the KCNQ5 sequence under the regulation of the same or a different promoter); (3) detection of mRNA transcripts by hybridization assays (e.g., Northern blotting or a nuclease protection assay using a probe complementary to the RNA sequence); (4) immunodetection of gene expression (e.g., by Western blotting with antibody to KCNQ5 protein); (5) detection of potassium channel activity, such as by patch-clamp analysis, radioisotope (e.g., $^{86}Rb$) efflux, two electrode voltage clamp, or membrane potential-sensitive reagents (e.g., Dibac from Molecular Probes International); and (6) PCR with primers homologous to expression vector sequences or sequences encoding KCNQ5 protein. The PCR produces a DNA fragment of predicted length, indicating incorporation of the expression system in the host cell. DNA sequencing may be performed by various known methods. See, for example, the dideoxy chain termination method in Sanger et al., 1977, *Proc. Natl. Acad. Sci. U.S.A.*, 74: 5463–7 and the Maxam-Gilbert method in Maxam-Gilbert, 1977, *Proc. Natl. Acad. Sci. U.S.A.*, 74: 560–4.

The KCNQ5 polypeptide of the present invention can be expressed as a recombinant protein with one or more additional polypeptide domains added to facilitate isolation and protein purification. Nonlimiting examples of protein purification facilitating domains include metal chelating peptides, such as histidine-tryptophan modules that allow purification on immobilized beads (J. Porath, 1992, *Protein Exp. Purif.* 3:263); protein A domains that allow purification on immobilized immunoglobulin; and the FLAGS domain extension/affinity purification system (Immunex Corp.). The inclusion of a cleavable linker sequence, such as Factor XA, or enterokinase (Invitrogen), between the purification domain and the potassium channel coding region is also useful to facilitate purification of the expressed KCNQ5 polypeptide.

Further, a host cell strain may be selected for its ability to modulate the expression of the inserted and expressed sequences, or to process the expressed protein in a desired fashion. Such modifications of the polypeptide include, but are not limited to, acetylation, carboxylation, glycosylation, phosphorylation, lipidation and acylation. Post-translational processing which cleaves a nascent form of the protein may also be important for correct folding, insertion and/or function. Different host cells, such as CHO, HeLa, MDCK, 293 (ATCC CRL 1573), WI38, NIH 3T3, HEK293, and the like, have specific cellular machinery and characteristic mechanisms for such post-translational activities, and may be employed to ensure the correct modification and processing of the introduced, heterologous protein.

Examples of protocols useful for detecting and measuring the expression of the novel KCNQ5 potassium channel polypeptide using either polyclonal or monoclonal antibodies include, but are not limited to, enzyme linked immunosorbent assay (ELISA), radioimmunoassay (RIA), and fluorescence activated cell sorting (FACS). A two-site, monoclonal antibody-based immunoassay utilizing monoclonal antibodies reactive to two non-interfering epitopes may be utilized. Competitive binding techniques may also be employed (See, for example, R. Hampton, 1990, *Serological Methods—A Laboratory Manual*, APS Press, St. Paul, Minn. and D. E. Maddox et al., 1983, *J. Exp. Med.*, 158:1211.

As will be appreciated by those having skill in the art, the host cells of this invention can be employed in a variety of ways that are now apparent. For example, the cells can be used to screen for compounds that bind to or otherwise modulate or regulate the function of the KCNQ5 protein, or at least one subunit thereof, which would be useful for modulation, for example activation, of KCNQ5 protein activity; to study signal transduction mechanisms and protein-protein interactions; and to prepare KCNQ5 protein for the uses as further described below. Membrane preparations from cells transfected with vectors harboring the KCNQ5 nucleic acid sequence, or a functional portion thereof, wherein the KCNQ5 potassium channel polypeptide, or a portion thereof, is expressed in the membranes, can be used for screening compounds, for example as described in the protocols of international application WO 99/31232.

Not all expression vectors and DNA regulatory sequences will function equally well to express the DNA sequences of this invention. Neither will all host cells function equally well with the same expression system. However, one of ordinary skill in the art may make a selection among expression vectors, DNA regulatory sequences, and host cells using the guidance provided herein without undue experimentation and without departing from the scope of the invention, to achieve expression and purification of the KCNQ5 protein for the variety of uses described.

KCNQ5 Polypeptide

Another embodiment of the present invention encompasses polypeptides comprising all or a portion of the amino acid sequence of the hKCNQ5 protein (SEQ ID NO:2). Where a portion of the hKCNQ5 protein is used, the portion preferably exhibits potassium ($K^+$) channel activity or can be modulated to exhibit $K^+$ channel activity. In addition, and within the scope of the invention, are polypeptides that comprise all or a portion of KCNQ5 that may contain one or more mutations so that the protein(s) fails to exhibit $K^+$ channel activity, but can be used to screen for compounds that will activate the protein or portion thereof.

These KCNQ5 polypeptides may be prepared by methods known in the art. For example, chemical synthesis, such as the solid phase procedure described by Houghton et al., 1985, *Proc. Natl. Acad. Sci. U.S.A.*, 82: 5131–5, can be used. Another method is in vitro translation of mRNA. A preferred method involves the recombinant production of protein in host cells as described above. For example, DNA comprising all or a portion of SEQ ID NO:1 can be synthesized by PCR as described above, inserted into an expression vector, and a host cell transformed with the expression vector. Thereafter, the host cell is cultured to produce the desired polypeptides, which are isolated and purified. Protein isolation and purification can be achieved by any one of several known techniques; for example and without limitation, ion exchange chromatography, gel filtration chromatography and affinity chromatography, high pressure liquid chromatography (HPLC), reversed phase HPLC, preparative disc gel electrophoresis.

In addition, cell-free translation systems (see J. Sambrook et al., supra) can be used to produce recombinant KCNQ5 polypeptides or peptides. Suitable cell-free expression systems for use in accordance with the present invention include rabbit reticulocyte lysate, wheat germ extract, canine pancreatic microsomal membranes, E. coli S30 extract, and coupled transcription/translation systems (Promega Corp., Madison, Wis.). These systems allow the expression of recombinant polypeptides or peptides upon the addition of cloning vectors, DNA fragments, or RNA sequences containing coding regions and appropriate promoter elements.

As mentioned supra, protein isolation/purification techniques may require modification of the hKCNQ5 protein using conventional methods. For example, a histidine tag can be added to the protein to allow purification on a nickel column. Other modifications may cause higher or lower activity, permit higher levels of protein production, or simplify purification of the protein. Such modifications may also help to identify specific KCNQ5 amino acids involved in binding, which, in turn, may assist in the rational drug design of KCNQ5 modulators. Amino acid substitutions can be made based on similarities in polarity, charge, solubility, hydrophobicity, hydrophilicity and/or the amphipathic nature of the residues involved. Preferably, the biological activity or functional activity of the potassium channel is retained. For example, negatively charged amino acids include aspartic acid and glutamic acid; positively charged amino acids include lysine and arginine. Amino acids with uncharged polar head groups or nonpolar head groups having similar hydrophilicity values include the following: leucine, isoleucine, valine; glycine, alanine; asparagine, glutamine; serine, threonine; phenylalanine and tyrosine.

Conservative substitutions of amino acids in the KCNQ5 polypeptide of the present invention may include the use of a chemically derivatized residue to replace a non-derivatized residue, with the proviso that the derivatized polypeptide displays the desired biological activity. D-isomers, as well as other known derivatives, may also be substituted for the naturally-occurring amino acids. (See, for example, U.S. Pat. No. 5,652,369, issued Jul. 29, 1997). Preferably, conservative substitutions are made without altering the biological activity of the resulting polypeptide. All of the above-described modified polypeptides are included within the scope of the present invention.

Accordingly, the present invention embraces variants of the human KCNQ5 potassium channel molecule. Preferred are variants having at least about 80–85% total amino acid sequence similarity to SEQ ID NO:2; more preferred are variants having at least 90% total amino acid sequence similarity to SEQ ID NO:2; and most preferred are variants having at least 95% total amino acid sequence similarity to SEQ ID NO:2, or a biologically active fragment thereof. A variant of the KCNQ5 polypeptide may have an amino acid sequence that is different by one or more amino acid substitutions, or it may include conservative changes, wherein a substituted amino acid has similar structural or chemical properties, for example, replacement of leucine with isoleucine. It may happen, although more rarely, that a variant has nonconservative changes, for example, the replacement of a glycine with a tryptophan. Similar minor variations may also include amino acid deletions or insertions, or both. Those having skill in the art will appreciate that guidance in determining which and how many amino acid residues may be substituted, inserted, or deleted without abolishing or diminishing biological or immunological activity may be obtained using computer programs known and used in the art, such as DNAStar software.

Also contemplated according to the present invention are a number of other variations of the above-described polypeptides. Such variations include salts and esters of the polypeptides, as well as precursors of the aforementioned polypeptides (e.g., having N-terminal substituents such as methionine, N-formylmethionine and leader sequences). The present invention is intended to embrace all such variations.

As will be described further infra, the hKCNQ5 polypeptide, and peptides thereof, of the present invention can be utilized in a wide variety of ways. For example, one may use them to generate polyclonal or monoclonal antibodies by techniques known and practiced in the art. The antibodies can be used for immunodetection (e.g., radioimmunoassay, enzyme immunoassay, or immunocytochemistry), immunopurification (e.g., affinity chromatography) of polypeptides from various sources, or immunotherapy (i.e., for potassium channel inhibition or activation). Further, the KCNQ5 polypeptide, or peptide fragments thereof, can be used in screening or binding assays.

Functional Expression

Biologically active hKCNQ5 mRNA can be introduced into host cells, either heterologous or homologous to the vector or polynucleotide molecule, for functional expression and analyses by methods well-known in the art. Synthetic mRNA from vector constructs as described herein, for example, may be injected into Xenopus oocytes for functional expression analysis (Goldin, A., 1992, Methods Enzymol., 207:266). Expressed hKCNQ5 potassium channels can be examined using standard two-electrode voltage clamp techniques (See, for example, Stuhmer W., 1992, Methods Enzymol., 207:319; and Kohler et al., 1996, Science, 273:1709). Potassium concentrations inside the cell may be altered, for example, by adding a potassium ionophore, or by co-expression with a receptor that causes a rise in intracellular potassium. Alternatively, potassium concentrations may be altered by pulling inside-out patches and changing potassium concentrations in the bath medium (See, for example, Grissmer, S. et al., 1993, J. Gen. Physiol., 102:601). Standard biophysical parameters, such as activators, potassium dependence, single-channel conductance, inactivation, tail currents, potassium selectivity, and pharmacology of various K+ channel blockers, including TEA (Example 4), Apamin, and the like, may be tested (See, Grissmer, S. et al., 1993, J. Gen. Physiol., 102:601).

Alternatively, cRNA (i.e., synthetic RNA from a cDNA construct) can be introduced into host cells, such as Xenopus oocytes, as described above (Example 4), or mammalian cells, for example, RBL cells (ATCC CRL 1378) or 293 cells (ATCC CRL 1573), can be transformed using routine methods in the art. As an example, direct nucleic acid injection can be employed, such as the Eppendorf microinjection system (Micromanipulator 5171 and Transjector 5242). The injected/transformed cells can be analyzed for K+ currents about 4 hours later using patch-clamp techniques, which are commonly practiced in the art (S. R. Ikeda et al., 1992,

*Pflugers Arch.*, 422(2):201–203; and S. Grissmer et al., 1993, *J. Gen. Physiol.*, 102:601).

Over-expression of the Novel KCNQ5 Channel in Cell Lines

Transient and/or stably transfected cells, preferably eukaryotic cells, such as HEK cells, containing the KCNQ5 nucleic acid comprising the coding region, are envisioned for high level expression of the KCNQ5 potassium channel. Such eukaryotic transfectants are suitable for using in performing pharmacological target binding studies for the identification of molecules that open or block the novel KCNQ5 channel.

Transient expression of the KCNQ5 coding region can be achieved by direct transfection into mammalian cells using standard techniques (Omari, K. et al., 1997, *J. Physiol.*, 499:369; Panyi, G. et al., 1996, *J. Gen. Physiol.*, 107(3) :409). High level transient expression can be attained using viral systems commonly used in the art, e.g., vaccinia virus, baculovirus, or adenovirus. Channel numbers resulting from these systems are typically from 5 to 500K per cell (Kamb, A. et al., 1992, *Methods Enzymol.*, 207:423; Sun, T. et al., 1994, *Biochemistry*, 33(33):9992; and Spencer, R. H. et al., 1997, *J. Biol. Chem.*, 272:2389).

Stable transfection of host cells using nucleic acid sequences, e.g., (SEQ ID NO:1), which encode the novel hKCNQ5 potassium channel described herein (SEQ ID NO:2), or biologically active variants or fragments thereof, can be prepared using, for example, 3T3, L929, COS, HEK or CHO cells. A vector suitable for use in preparing stable transfectants is pcDNA/neo (Invitrogen).

An exemplary procedure for carrying out the transfection assays is as follows. Cells are grown to about 50% confluency in 60 mm tissue culture plates in media and under conditions that are according to the requirements of the particular cell line. Cells are transfected or transformed with 5 $\mu$g of pure DNA comprising a coding region for the KCNQ5 potassium channel, e.g., SEQ ID NO:1, in a pCDNA/neo plasmid vector using the Lipofection reagent as described by the supplier (Life Technologies Gibco BRL, Bethesda, Md.). After transfection, the cells are incubated at 37° C. for three days in medium containing 10% FCS. Cells are typsinized, seeded onto 100 mm plates, and then selected with 300 $\mu$g/ml of G418 (neomycin). Only those cells which have stably integrated the heterologous coding region will grow in the presence of G418, since resistance is conferred by the neomycin-resistance gene in the vector. Isolated clones are processed for about 2–3 rounds of selection/purification and are subjected to patch-clamp analysis for K+ currents.

The various cell lines that express or over-express the novel KCNQ5 encoded by the polynucleotide coding region, i.e., SEQ ID NO:1, or functional fragment thereof, can be used in ligand binding assays to screen for pharmacologically active molecules that bind the KCNQ5 channel, or one or more subunits thereof. For example, a radio-labeled ligand is used as a measurable displacement entity in a noncompetitive or competitive binding assay. Nonlimiting examples of ligands for use in such assays include TEA; 4-aminopyridine (4-AP), as well as 2-AP and 3-AP; 3,4- and 2,3-diaminopyridine; $BaCl_2$; CsCl; strychnine; phencyclidine; pyridostigmine; 9-aminoacridine; DuP-996 (3,3-bis (4-pyridinylmethyl)-1-phenlindolin-2-one; linopiridine); clofilium; quinidine; aminoquinolines; and quinine. Examples of peptide toxins for use as ligands in such binding assays include, but are not limited to, stichodactylotoxin, apamin, charybdotoxin, kaliotoxin and margotoxin.

Method for Detecting KCNQ5-Encoding Nucleic Acids

Another embodiment of the present invention provides a method for detecting nucleic acids encoding the KCNQ5 protein. In this method, nucleic acids of unknown sequence are contacted with a nucleic acid having a sequence complementary to a known coding sequence (e.g., a sequence of at least about 10 nucleotides from, e.g., SEQ ID NO:1, particularly the coding region thereof), wherein the latter nucleic acid has a detectable marker; and (b) the presence of marker bound to any of the nucleic acids of unknown sequence is determined. The presence of bound marker indicates the presence of the desired nucleic acids. This method can be applied to detect KCNQ5 nucleic acid in other tissues (which may have different regulatory elements) and nucleic acids from other species (e.g., monkey).

Nucleic acids for analysis by this method can be obtained using commonly practiced and routine methods in the art. For genomic DNA, a tissue sample can be rapidly frozen and then crushed into readily digestible pieces, which are incubated in an enzyme, such as proteinase K, and SDS to degrade most of the cellular proteins. The genomic DNA is then deproteinized by successive phenol/chloroform/isoamyl alcohol extractions, recovered by ethanol precipitation, dried and resuspended in buffer. For RNA, cultured cells are lysed in 4M guanidinium solution and the lysate is drawn through a 20-gauge needle. The RNA is applied to a cesium chloride step gradient and pelleted by centrifugation and the supernatant is removed. The pellet should contain purified RNA.

The detectable marker may be a radioactive ion linked to one of the nucleotides of the complementary nucleic acid. Common radioactive labels are $^{32}P$ and $^{35}S$, although other labels, such as biotin-avidin, may be used. Those having skill in the art are aware of various methods to attach the labels to the complementary nucleic acid (e.g., the random primer method for attachment of $^{32}P$ or $^{35}S$).

Methods of detecting nucleic acids are generally known by those having ordinary skill in the art. For example, one may perform a Southern or Northern blotting procedure using a radiolabeled KCNQ5 complementary oligonucleotide probe. Hybridization is then detected by autoradiography. Depending on the marker, other detection methods (e.g., spectrophotometry and non-radioactive labels, such as chemiluminescence or fluorescence or enzymes).

Methods for Detecting KCNQ5 Protein Modulators/Screening Assays

The present invention is further directed to methods for detecting modulators of the KCNQ5 protein described herein. A screen for KCNQ5 protein modulators entails detecting binding of molecules (e.g., polypeptides, natural products, synthetic compounds) in cells expressing KCNQ5 protein.

The cloning and sequencing of the hKCNQ5 polynucleotide provides the ability to generate recombinant host cells useful in expressing all or a portion of the KCNQ5 protein allowing for screening of natural products and synthetic compounds that bind to and/or modulate KCNQ5 protein activity. A process for detecting KCNQ5 protein modulators requires transforming a suitable vector into compatible host cells as described supra. Transformed cells are then treated with test substances (e.g., synthetic compounds or natural products), and channel activity is measured and/or assessed in the presence and absence of the test substance.

More specifically, compounds that modulate KCNQ5 activity may be DNA, RNA, peptides, proteins, or non-protein organic molecules. Such compounds may modulate channel activity by increasing or attenuating the expression of DNA or RNA which encodes the potassium channel, or may antagonize or agonize the biological activity of the novel KCNQ5 channel itself. The assays to detect compounds that modulate the expression of DNA or RNA encoding hKCNQ5 may be a simple "yes/no" assay to qualitatively determine if there is a change in expression or function. Alternatively, the assay may be made quantitative by comparing the expression or function of a test sample with the levels of expression or function in a standard sample.

The human KCNQ5 protein described herein, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the potassium channel protein and the agent being tested can be measured. Thus, the present invention provides a method for screening or assessing a plurality of compounds for their specific binding affinity with the KCNQ5 potassium channel polypeptide, or a bindable portion thereof, e.g. a subunit, comprising providing a plurality of compounds, combining the KCNQ5 polypeptide, or a bindable fragment thereof, with each of a plurality of compounds for a time sufficient to allow binding under suitable conditions and detecting binding of the KCNQ5 polypeptide to each of the plurality of test compounds, thereby identifying the compounds that specifically bind to the KCNQ5 polypeptide.

Methods of identifying compounds that modulate the activity of the hKCNQ5 potassium channel polypeptide are provided by the present invention and comprise combining a potential or candidate compound or drug modulator of a potassium channel biological activity with a KCNQ5 polypeptide, preferably having the amino acid sequence set forth in SEQ ID NO:2, and measuring an effect of the candidate compound or drug modulator on the biological activity of the KCNQ5 polypeptide. Such measurable effects include, for example, physical binding interaction; the ability to pass K+ ions, or other ions used for screening; effects on native and cloned KCNQ5 cell line membrane potential, effects on neurotransmitter release, and effects of modulators or other KCNQ5-mediated neurophysiological measures.

Another method of identifying compounds that modulate the biological activity of the hKCNQ5 potassium channel polypeptide comprises combining a potential or candidate compound or drug modulator of a potassium channel biological activity with a host cell that expresses a KCNQ5 polypeptide, preferably having the amino acid sequence set forth in SEQ ID NO:2, and measuring an effect of the candidate compound or drug modulator on the biological activity of the KCNQ5 polypeptide. The host cell can also be capable of being induced to express the KCNQ5 polypeptide, e.g., via inducible expression. Physiological effects of a given modulator candidate on the KCNQ5 potassium channel polypeptide can also be measured. Thus, cellular assays for KCNQ5 modulators may be either direct measurement or quantification of the physical biological activity of the potassium channel, or may be measurement or quantification of a physiological or a neurological effect. Such methods preferably employ the hKCNQ5 potassium channel polypeptide described herein, or overexpressed recombinant KCNQ5 potassium channel polypeptide in suitable host cells containing an expression vector as described herein, wherein the KCNQ5 potassium channel polypeptide is expressed, overexpressed, or undergoes upregulated expression.

Another aspect of the present invention embraces a method of screening for a compound that is capable of modulating the biological activity of the KCNQ5 polypeptide, comprising providing a host cell containing an expression vector harboring a nucleic acid sequence encoding the KCNQ5 polypeptide (SEQ ID NO:2), or a functional portion thereof; determining the biological activity of the expressed KCNQ5 polypeptide in the absence of a modulator compound; contacting the cell with the modulator compound and determining the biological activity of the expressed KCNQ5 polypeptide in the presence of the modulator compound. In such a method, a difference between the activity of the KCNQ5 polypeptide in the presence of the modulator compound and in the absence of the modulator compound indicates a modulating effect of the compound.

In another of its aspects, the present invention encompasses screening and small molecule (e.g., drug) detection assays which involve the detection or identification of small molecules that can bind to a given protein, i.e., the KCNQ5 protein. Particularly preferred are assays suitable for high throughput screening methodologies. In such binding-based screening or detection assays, a functional assay is not typically required. All that is needed is a target protein, preferably substantially purified, and a library or panel of compounds (e.g., ligands, drugs, small molecules) to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News*, 20(8)). The assay allows the detection of small molecules (e.g., drugs, ligands) that bind to expressed, and preferably purified, KCNQ5 protein based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a KCNQ5 potassium channel polypeptide to measure a biological binding or ligand binding activity, the source may be a whole cell lysate that can be prepared by successive freeze-thaw cycles (e.g., one to three) in the presence of standard protease inhibitors. The hKCNQ5 potassium channel may be partially or completely purified by standard protein purification methods, e.g., affinity chromatography using specific antibody described infra, or by ligands specific for an epitope tag engineered into the recombinant KCNQ5 polypeptide molecule, also as described herein. Binding activity can then be measured as described.

Compounds which are identified according to the methods provided herein, and which modulate or regulate the biological activity or physiology of the KCNQ5 potassium channel according to the present invention are a preferred embodiment of this invention. It is contemplated that such modulatory compounds may be employed in treatment methods for treating a condition that is mediated by the novel hKCNQ5 potassium channel by administering to an individual in need of such treatment a therapeutically effective amount of the compound identified by the methods described herein.

In addition, the present invention provides methods for treating an individual in need of such treatment for a condition that is mediated by the hKCNQ5 potassium channel of the invention, or by a neuroaffective, neurophysiological, or neuropsychological disorder or condition, such as described herein, comprising administering to the individual a therapeutically effective amount of the hKCNQ5 channel-modulating compound identified by a method provided herein.

Chimeric or Fusion Proteins Involving hKCNQ5

In another embodiment of the present invention, a nucleic acid sequence which encodes a hKCNQ5 potassium channel molecule substantially as depicted in SEQ ID NO:2, or a biologically active fragment thereof, can be ligated to a heterologous sequence to encode a fusion protein (also called a chimeric protein). For example, for screening compounds for modulating biological activity of hKCNQ5, it may be useful to encode a chimeric potassium channel molecule as described herein for expression in host cells.

Chimeric constructs may also be used to express a "bait", according to methods well known using a yeast two-hybrid system, to identify accessory native peptides that may be associated with the novel KCNQ5 potassium channel molecule described herein. (Fields, S. et al., 1995, *Trends Genet.*, 10:286; Allen, J. B. et al., 1995, *TIBS*, 20:511). A yeast two-hybrid system has been described wherein protein:protein interactions can be detected using a yeast-based genetic assay via reconstitution of transcriptional activators. (Fields, S. and Song, O., 1989, *Nature*, 340:245). The two-hybrid system involves the ability of a pair of interacting proteins to bring a transcription activation domain into close proximity with a DNA-binding site that regulates the expression of an adjacent reporter gene. Commercially available systems such as the Clontech Matchmaker™ systems and protocols (Clontech, Palo Alto, Calif.) may be used with conjunction with the present invention. (See also, Mendelsohn, A. R. and Brent, R., 1994, *Curr. Op. Biotech.*, 5:482; Phizicky, E. M. and Fields, S., 1995, *Microbiological Rev.*, 59(1):94; Yang, M. et al., 1995, *Nucleic Acids Res.*, 23(7):1152; Fields, S. and Sternglanz, R., 1994, *TIG*, 10(8):286; and U.S. Pat. Nos. 6,283,173 and 5,468,614).

Modified screening systems, for instance, can be practiced either with a positive readout or with a negative readout such as that in the recently developed versions of "Reverse Y2H" approach. (See, for example, Vidal M. et al., 1996, *Proc. Natl. Acad. Sci. U.S.A.*, 17;93(19):10321–10326; Vidal M., et al., 1996, *Proc. Natl. Acad. Sci. U.S.A.*, 17;93(19):10315–10320; White M. A., 1996, *Proc. Natl. Acad. Sci. U.S.A.*, 17;93(19):10001–10003; and Leanna C. A. and Hannink M., 1996, *Nucleic Acids Res.*, 1;24(17):3341–3347).

Antibodies

Polyclonal antibodies that are immunoreactive with (and monospecific for) the KCNQ5 polypeptide, or an immunoreactive fragment thereof, can be purified from antisera of an animal previously immunized with the KCNQ5 polypeptide, or immunoreactive fragment thereof, as immunogen. In addition, monoclonal antibodies can be prepared using protocols and techniques routinely practiced in the art (e.g., Kohler and Milstein, 1975, *Nature*, 256:495).

Nonlimiting examples of peptide fragments or portions of the KCNQ5 polypeptide for use as immunogens, or in methods as described herein, include the following: peptide fragment 1 ends at amino acid 51 of the KCNQ5 polypeptide sequence and comprises the sequence GGGGGGLRESRRGKQGAR (SEQ ID NO:5); peptide fragment 2 ends at amino acid 80 of the KCNQ5 polypeptide sequence and comprises the sequence PLSYTSSQSCRRNVKYRRVQNYL (SEQ ID NO:6); peptide fragment 3 ends at amino acid 166 and comprises the sequence CRYRGWQGRLRFARKP (SEQ ID NO:7); peptide fragment 4 ends at amino acid 262 of the KCNQ5 polypeptide sequence and comprises the sequence VEKDANKEFST (SEQ ID NO:8); peptide fragment 5 ends at amino acid 335 of the KCNQ5 polypeptide sequence and comprises VQEQHRQKHFEKRRNPA (SEQ ID NO:9); polypeptide fragment 6 ends at amino acid 453 of the KCNQ5 polypeptide sequence and comprises the sequence HTCSPTKKEQGEASSSQKLSFKERVRMASPRGQSIKSRQASVGDRRSPS TDITAEGSPTKVQKSWSFNDRTRFRPSLRLKSSQPKPVI (SEQ ID NO:10); peptide fragment 7 ends at amino acid 471 of the KCNQ5 polypeptide sequence and comprises the sequence LGTDDVYDEKGCQ (SEQ ID NO:11); peptide fragment 8 ends at amino acid 511 of the KCNQ5 polypeptide sequence and comprises the sequence HVAKRKFKETLRPYDV (SEQ ID NO:12); peptide fragment 9 ends at amino acid 564 of the KCNQ5 polypeptide sequence and comprises the sequence LGKGQITSDKKSREKITAEHETTDD (SEQ ID NO:13); peptide fragment 10 ends at amino acid 585 of the KCNQ5 polypeptide sequence and comprises the sequence KVEKQVQSIESKL (SEQ ID NO:14); peptide fragment 11 ends at amino acid 652 of the KCNQ5 polypeptide sequence and comprises the sequence PPFECEQTSDYQSPVDSKDLSGSAQNSGCLSRSTSANISRG (SEQ ID NO:15); peptide fragment 12 ends at amino acid 709 of the KCNQ5 polypeptide sequence and comprises the sequence TIANQINTAPKPAA (SEQ ID NO:16); peptide fragment 13 ends at amino acid 738 of the KCNQ5 polypeptide sequence and comprises the sequence KHLPRPETLHPNPAGL (SEQ ID NO:17); peptide fragment 14 ends at amino acid 777 of the KCNQ5 polypeptide sequence and comprises the sequence SKENVQVAQSNLTKDRSMRKSFDMGG (SEQ ID NO:18); peptide fragment 15 ends at amino acid 833 of the KCNQ5 polypeptide sequence and comprises the sequence LSGSESSGSRGSQDFYPKWRESK (SEQ ID NO:19); peptide fragment 16 ends at amino acid 860 of the KCNQ5 polypeptide sequence and comprises the sequence EEVGPEETETDTFDAAPQPARE (SEQ ID NO:20); and peptide fragment 17 ends at amino acid 880 of the KCNQ5 polypeptide sequence and comprises the sequence DSLRTGRSRSSQSIC (SEQ ID NO:21).

As used herein, "antibody" or "antibodies" refers to intact molecules as well as fragments thereof, such as Fab, F(ab)$_2$, and Fv, which are capable of binding an epitopic determinant of the KCNQ5 immunogen. As will be appreciated by those having skill in the art, the immunogen can be conjugated to a carrier protein, if desired, to increase immunogenicity, particularly, if a small peptide or fragment of the KCNQ5 polypeptide is used. Commonly used carriers that are routinely chemically coupled to peptides include serum albumins, i.e., bovine, sheep, goat, or fish serum albumin; thyroglobulin; and keyhole limpet hemocyanin. The coupled immunogen-carrier is then used to immunize a recipient animal (e.g., mouse, rat, guinea pig, sheep, goat, or rabbit).

The term "antigenic determinant" refers to that fragment of a molecule (i.e., an epitope) that makes contact with a particular antibody. When an isolated and/or purified KCNQ5 polypeptide is used to immunize a host animal, numerous regions of the polypeptide may induce the production of antibodies which bind specifically to a given region or three-dimensional structure on the polypeptide; these regions or structures are referred to as antigenic determinants or epitopes. An antigenic determinant may compete with the intact antigen (i.e., the immunogen used to elicit the immune response) for binding to an antibody.

The antibodies can be elicited in an animal host by immunization with KCNQ5-derived immunogenic components, or can be formed by in vitro immunization (sensitization) of immune cells. The antibodies can also be produced in recombinant systems transformed, transfected, infected or transduced with appropriate antibody-encoding DNA. Alternatively, the antibodies can be constructed by biochemical reconstitution of purified heavy and light chains. Antibodies embraced by the present invention include hybrid antibodies, chimeric antibodies, humanized antibodies (see, for example, U.S. Pat. No. 5,585,089 to C. J. Queen et al.) and univalent antibodies. Using such antibodies, for example, KCNQ5 polypeptide, or an immunogenic fragment or portion thereof, can be detected in a test sample by chromatography on antibody-conjugated solid-phase matrices or supports (see E. Harlow and D. Lane, 1999, *Using Antibodies: A Laboratory Manual*, Cold Spring Harbor Laboratory, Cold Spring Harbor, N.Y.), or by immunoassay. Preferred are antibodies that specifically recognize and bind to KCNQ5.

Thus, according to the present invention, antibodies can be generated that are specific for the full-length KCNQ5 molecule, or immunoreactive portions or fragments thereof. The antibodies can be employed to prepare KCNQ5 potassium channel antibody affinity columns. For example, gel supports or beads can be activated with various chemical compounds, e.g., cyanogen bromide, N-hydroxysuccinimide esters, and antibodies can be bound thereto. More particularly and by way of example, anti-KCNQ5 potassium channel antibodies can be added to Affigel-10 (Biorad), a gel support which is activated with N-hydroxysuccinimide esters, such that the antibodies form covalent linkages with the agarose gel bead support. The antibodies are then coupled to the gel via amide bonds with a spacer arm. The remaining activated esters are then quenched with ethanolamine HCl, 1M, pH 8. The column is washed with water, followed by 0.23M glycine HCl, pH 2.6, to remove any non-conjugated antibody or extraneous protein. The column is then equilibrated in phosphate buffered saline (PBS), (pH 7.3) with appropriate detergent, and the sample materials, i.e., cell culture supernatants or cell extracts, for example, containing hKCNQ5 polypeptide (prepared using appropriate membrane solubilizing surfactants) are slowly passed over the column. The column is washed with PBS/surfactant until the optical density falls to background. The protein is then eluted from the column with 0.23M glycine-HCl, pH 2.6/surfactant. The purified hKCNQ5 polypeptide is then dialyzed against PBS/surfactant.

Recombinant hKCNQ5 potassium channel molecules can be separated from cellular proteins by use of an immunoaffinity column made with monoclonal or polyclonal antibodies that are specific for either full-length hKCNQ5 potassium channel polypeptide, or peptide fragments of hKCNQ5.

In addition, the KCNQ5 potassium channel polypeptide of the present invention can be used to affinity purify biological effectors from biological materials, e.g., disease tissue or cells, using affinity chromatography techniques that are known and practiced by those having skill in the art. For example, a KCNQ5 potassium channel polypeptide, or a peptide or fragment thereof, is affixed to a solid matrix, e.g., CNBr-activated Sepharose, according to the protocol of the supplier (Pharmacia, Piscataway, N.J.). An homogenized and buffered cellular or tissue solution containing a potential biomolecule of interest is passed through the column. After washing, the column retains only the biological effector molecule, which is subsequently eluted from the column, e.g., using 0.5M acetic acid or a NaCl gradient.

Diagnostic Assays

Antibody titers of ascites or hybridoma culture fluids are determined by various serological or immunological assays which include, but are not limited to, precipitation, passive agglutination, enzyme-linked immunosorbent assay (ELISA) and radioimmunoassay (RIA) techniques. Similar diagnostic assays are used to detect the presence of the novel KCNQ5 potassium channel biomolecule in body fluids, tissue and cell extracts, or membrane preparations.

Diagnostic assays using antibodies immunoreactive with the human KCNQ5 potassium channel polypeptide are useful for the diagnosis of conditions, disorders or diseases characterized by the abnormal expression of the hKCNQ5 protein, or by the expression of genes associated with abnormal cell growth or abnormal neurophysiology. Diagnostic assays for the hKCNQ5 biomolecule of this invention include methods utilizing an antibody and a label to detect the human KCNQ5 potassium channel polypeptide in human body fluids, cells, tissues or sections or extracts or membrane preparations of such tissues. The polypeptides and antibodies of the present invention may be used with or without modification. Frequently, the polypeptides and antibodies are labeled by conjugating them, either covalently or noncovalently, with a reporter molecule, a vast number and type of which are well-known to those skilled in the art.

A variety of protocols for measuring the KCNQ5 potassium channel polypeptide, using either polyclonal or monoclonal antibodies specific for the protein are known in the art. Examples include ELISA, RIA and fluorescence activated cell sorting (FACS). A two-site, monoclonal-based immunoassay utilizing monoclonal antibodies reactive with two non-interfering epitopes on the hKCNQ5 potassium channel polypeptide is preferred, but a competitive binding assay can also be employed. These assays are described in a number of publications available to the skilled practitioner, among them: Maddox, D. E. et al., 1983, *J. Exp. Med.*, 158:1211; Sites, D. P. et al., 1, *Basic and Clinical Immunology*, Ch. 22, 4$^{th}$ Ed., Lange Medical Publications, Los Altos, Calif. (1982); U.S. Pat. Nos. 3,654,090; 3,850, 752; and 4,016,043.

In order to provide a basis for the diagnosis of disease, normal or standard values for the human KCNQ5 potassium channel polypeptide expression are preferably established. This is accomplished by combining body fluids, cell extracts, or cell membrane preparations from normal subjects, either animal or human, with antibody to the hKCNQ5 polypeptide under conditions suitable for complex formation; such conditions are well known in the art. The amount of standard complex formation may be quantified by comparing it with a dilution series of positive controls, where a known amount of antibody is combined with known concentrations of purified potassium channel polypeptide. Then, standard values obtained from the normal samples may be compared with values obtained from samples from subjects potentially affected by a disorder or disease related to/associated with hKCNQ5 channel biomolecule expression. Deviation between standard and subject values establishes the presence of the disease state.

Moreover, kits containing KCNQ5 potassium channel nucleic acid, antibodies to KCNQ5 channel polypeptide or KCNQ5 protein may be prepared. Such kits can be used to detect heterologous nucleic acid which hybridizes to the KCNQ5 potassium channel nucleic acid, or to detect the presence of KCNQ5 protein or peptide fragments in a sample. Such characterization is useful for a variety of purposes including, but not limited to, forensic analyses and epidemiological studies.

The DNA and RNA polynucleotide molecules, recombinant KCNQ5 protein and antibodies thereto, according to the present invention may be used to screen and measure levels of the novel potassium channel DNA, RNA or protein. The recombinant proteins, DNA and RNA polynucleotide molecules, and antibodies, allow the formulation of kits suitable for the detection and typing of the novel human KCNQ5 potassium channel molecule. Such a kit would comprise a compartmentalized carrier suitable to hold in close confinement at least one container. The carrier would further comprise reagents such as recombinant KCNQ5 potassium channel or anti-KCNQ5 potassium channel antibodies suitable for detecting the novel KCNQ5 potassium channel biomolecule. The carrier may also contain a means for detection such as labeled antigen or enzyme substrates or the like. Suitable instructions for performing the assays as intended by the kits are also included therein.

Polynucleotide sequences which encode the novel hKCNQ5 potassium channel of the present invention may be used for the diagnosis of neuroaffective, neurophysiological, or neuropsychological conditions or diseases with which the expression and/or function of the novel KCNQ5 biomolecule is associated or linked. For example, polynucleotide sequences encoding the KCNQ5 potassium channel may be used in hybridization or PCR assays of fluids or tissues or membrane preparations from biopsies to detect the expression of the biomolecule. The form of such qualitative or quantitative methods may include Southern or Northern analysis, dot blot or a variety of other membrane-based technologies; PCR technologies; dip stick, pin, chip and ELISA technologies. All of these techniques are well known in the art and are the basis of many commercially available diagnostic kits. Such assays may also be used to evaluate the efficacy of a particular therapeutic treatment regimen in animal studies, in clinical trials, or in monitoring the treatment of an individual patient. Once disease is established, a therapeutic agent is administered and a treatment profile is generated. Such assays may be repeated on a regular basis to evaluate whether the values in the profile progress toward or return to the normal or standard pattern. Successive treatment profiles may be used to show or monitor the efficacy of treatment over a period of several days or several months.

Polynucleotide sequences which encode the novel hKCNQ5 potassium channel may also be employed in analyses to map chromosomal locations, for example, to screen for functional association with disease markers. Moreover the sequences described herein are contemplated for use to identify human sequence polymorphisms and possible association with disease, as well as for analyses to select optimal sequences from among possible polymorphic sequences for the design of compounds to modulate the biological activity, and therefore regulate physiological disorders, most preferably neuroaffective or neurophysiological disorders in vivo. In addition, the sequences are contemplated to be used as screening tools for use in the identification of appropriate human subjects and patients for therapeutic clinical trials.

Therapeutic Agents/Uses

The sense and antisense KCNQ5 nucleic acid molecules can also be used as therapeutic agents for KCNQ-related indications. Vectors can be designed and constructed to direct the synthesis of the desired DNA or RNA or to formulate the nucleic acid as described in the art.

Antisense Nucleic Acid Molecules

Several references describe the usefulness of antisense molecules. See, for example, Toulme and Helene, 1988, *Gene* 72:51–8; Inouye, 1988, *Gene*, 72:25–34; Uhlmann and Peyman, 1990, *Chemical Reviews*, 90: 543–584; *Biotechnology Newswatch* (Jan. 15, 1996), p. 4; Robertson, 1997, *Nature Biotechnology*, 15:209; Gibbons and Dzau, 1996, *Science*, 272: 689–93. Antisense sequences can be designed based on genomic DNA and/or cDNA, 5' and 3' flanking control regions, other flanking sequences, intron sequences, and nonclassical Watson and Crick base pairing sequences used in the formation of triplex DNA. Such antisense molecules include antisense oligodeoxyribonucleotides, oligoribonucleotides, oligonucleotide analogues, and the like, and may comprise at least about 15 to 25 bases.

Antisense molecules may bind noncovalently or covalently to the KCNQ5 DNA or RNA. Such binding could, for example, cleave or facilitate cleavage of KCNQ5 DNA or RNA, increase degradation of nuclear or cytoplasmic mRNA, or inhibit transcription, translation, binding of transactivating factors, or pre-mRNA splicing or processing. Antisense molecules may also contain additional functionalities that increase stability, transport into and out of cells, binding affinity, cleavage of the target molecule, and the like. All of these effects would decrease expression of KCNQ5 protein and thus make the antisense molecules useful as KCNQ5 protein modulators.

In addition, the KCNQ5 nucleic acid sequence depicted in SEQ ID NO:1 may be used to design antisense molecules/constructs to investigate the physiological relevance of this novel potassium channel in cells by knocking out or knocking down the expression of the endogenous gene. For down-regulating the expression of the novel KCNQ5 potassium channel of the present invention in mammalian cells, an antisense expression construct containing the complement DNA sequence to the sequence, or a portion thereof, essentially as depicted in SEQ ID NO:1 can be prepared, for example, using the pREP10 vector (Invitrogen Corp.). Transcripts are expected to inhibit translation of the wild-type KCNQ5 mRNA in cells transfected with the construct. Antisense transcripts are effective for inhibiting translation of the native gene transcript and are capable of inducing physiological effects, e.g., regulation of neurophysiological disorders described herein. Translation is most effectively inhibited by blocking the mRNA at a site at or near the initiation codon. Accordingly, oligonucleotides that are complementary to the 5'-terminal region of the KCNQ5 potassium channel mRNA transcript are preferred. Secondary or tertiary structure which might interfere with hybridization is potentially minimal in this region. Moreover, sequences that are too distant in the 3' direction from the initiation site can be less effective in hybridizing with the mRNA transcripts because of a "read-through" phenomenon in which the ribosome appears to unravel the antisense/sense duplex to permit translation of the message.

Oligonucleotides that are complementary to and hybridizable with any portion of the novel KCNQ5 potassium channel mRNA are contemplated for use according to the present invention. (See, for example, U.S. Pat. No. 5,639,595, issued Jun. 17, 1997, wherein methods of identifying oligonucleotide sequences that display in vivo activity are described). As described therein, expression vectors containing random oligonucleotide sequences derived from previously known polynucleotides are transformed into cells. The cells are then assayed for a phenotype resulting from the desired activity of the oligonucleotide. Once cells with the desired phenotype have been identified, the sequence of the oligonucleotide having the desired activity can be identified. Identification may be accomplished by recovering the vector or by polymerase chain reaction (PCR)

amplification and sequencing the region containing the inserted nucleic acid material, using established methods and protocols in the art.

Nucleotide sequences that are complementary to the novel hKCNQ5 potassium channel polypeptide encoding polynucleotide sequence can be synthesized for antisense therapy. These antisense molecules may be DNA, stable derivatives of DNA, such as phosphorothioates or methylphosphonates, RNA, stable derivatives of RNA such as 2'-O-alkylRNA, or other oligonucleotide mimetics. (See, for example, U.S. Pat. No. 5,652,355, *Hybrid Oligonucleotide Phosphorothioates*, issued Jul. 29, 1997, and U.S. Pat. No. 5,652,356, *Inverted Chimeric and Hybrid Oligonucleotides*, issued Jul. 29, 1997, which describe the synthesis and effect of physiologically-stable antisense molecules).

Peptide nucleic acid (PNA) refers to an antisense molecule or antigenic agent which comprises an oligonucleotide linked to a peptide backbone of amino acid residues, terminating in lysine. PNA typically comprise oligonucleotides of at least 5 nucleotides linked to amino acid residues. These small molecules stop transcript elongation by binding to their complementary strand of nucleic acid (P. E. Nielsen et al., 1993, *Anticancer Drug Des.*, 8:53–63). PNA may be pegylated to extend their lifespan in the cell where they preferentially bind to complementary single stranded DNA or RNA.

Potassium channel antisense molecules may be introduced into cells by microinjection, liposome encapsulation or by expression from vectors harboring the antisense sequence, and the like. Antisense therapy may be particularly useful for the treatment of diseases where it is beneficial to modulate the biological activity of the hKCNQ5 potassium channel described herein.

Delivery of hKCNQ5 Nucleic Acid to Cells

The human KCNQ5 potassium channel polypeptide-encoding nucleic acid described herein may delivered to cells, either as naked DNA or in an expression vector, wherein the cells express the polypeptide. In this way, the KCNQ5 potassium channel polypeptide of the present invention can be delivered to the cells of target organs. Conversely, KCNQ5 potassium channel polypeptide antisense gene therapy may be used to modulate the expression of the polypeptide in the cells of target organs and thus regulate biological activity.

The potassium channel polypeptide coding region, or other suitable regions, e.g., the S4 or pore region coding regions, can be ligated into expression vectors, preferably, viral expression vectors, which mediate transfer of the transactivator polypeptide nucleic acid by infection of recipient host cells. Suitable viral vectors include retrovirus, adenovirus, adeno-associated virus, herpes virus, vaccinia virus, polio virus, modified human immunodeficiency virus (HIV), or portions thereof, and the like. See, e.g., U.S. Pat. No. 5,624,820, *Episomal Expression Vector for Human Gene Therapy*, issued Apr. 29, 1997.

The KCNQ5 nucleic acid coding region, or desired portion thereof, of the present invention is incorporated into effective eukaryotic expression vectors, which are directly administered or introduced into somatic cells (a nucleic acid fragment comprising a coding region, preferably mRNA transcript, may also be administered directly or introduced into somatic cells). See, e.g., U.S. Pat. No. 5,589,466, issued Dec. 31, 1996. Such nucleic acid and vectors may remain episomal, or they may be incorporated into the host chromosomal DNA as a provirus, or portion thereof, that includes the gene fusion and appropriate eukaryotic transcription and translation signals, i.e., an effectively positioned RNA polymerase promoter 5' to the transcriptional start site and ATG translation initiation codon of the gene fusion, as well as termination codon(s) and transcript polyadenylation signals effectively positioned 3' to the coding region.

Alternatively, the novel KCNQ5 potassium channel polypeptide DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection, or microparticle bombardment. These procedures and variations thereof are suitable for ex vivo, as well as in vivo therapies, including use in humans, according to established methods and protocols known in this art.

PCR Diagnostics

The hKCNQ5 nucleic acid sequence, oligonucleotides, fragments, portions or antisense molecules thereof, may be used in diagnostic assays of body fluids or biopsied tissues to detect the expression level of the KCNQ5 potassium channel molecule in such fluids and tissues. For example, sequences designed from the cDNA sequence SEQ ID NO:1 or sequences that encode SEQ ID NO:2 (all or a portion thereof) can be used to detect the presence of the mRNA transcripts in a patient or to monitor the modulation of transcripts during treatment.

One method for amplification of target nucleic acids, or for later analysis by hybridization assays, is the polymerase chain reaction ("PCR") or PCR technique. The PCR technique can be applied to detect sequences of the invention in suspected samples using oligonucleotide primers spaced apart from each other and based on the genetic sequence, e.g., SEQ ID NO:1, as set forth herein. The primers are complementary to opposite strands of a double stranded DNA molecule and are typically separated by from about 50 to 450 nucleotides or more (usually not more than 2000 nucleotides).

The PCR method entails preparing specific oligonucleotide primers followed by repeated cycles of target DNA denaturation, primer binding, and extension using a DNA polymerase to obtain DNA fragments of the expected length based on the primer spacing. The present invention provides a diagnostic composition for the identification of a polynucleotide sequence comprising the sequence substantially as depicted in SEQ ID NO:1, or nucleic acid sequences encoding the KCNQ5 polypeptide of SEQ ID NO:2, comprising PCR primers for amplification. The degree of amplification of a target sequence is controlled by the number of cycles that are performed and is theoretically calculated by the simple formula "2n", where n is the number of cycles. See, e.g., Perkin Elmer, *PCR Bibliography*, Roche Molecular Systems, Branchburg, N.J.; CLONTECH products, Palo Alto, Calif.; U.S. Pat. No. 5,629,158, *Solid Phase Diagnosis of Medical Conditions*, issued May 13, 1997.

KCNQ5-containing Compositions

Pharmaceutically useful compositions comprising sequences pertaining to the novel hKCNQ5 potassium channel polypeptide, DNA, RNA, antisense sequence, the human KCNQ5 polypeptide itself, or variants and analogs which have biological activity or, otherwise, compounds which modulate KCNQ5 physiology/activity and identified by methods described herein, may be formulated as compositions, preferably physiologically acceptable compositions, according to known methods, such as by the admixture of a pharmaceutically acceptable carrier, diluent, or excipient. Examples of such carriers and methods of formulation may be found in *Remington's Pharmaceutical Sciences*, 18th Ed., 1990, Mack Publishing Co, Easton, Pa. To formulate a pharmaceutically acceptable composition suitable for effective administration, preferably in vivo, or even ex vivo, such compositions will contain an effective amount of the protein, DNA, RNA, or compound modulator.

Therapeutic or diagnostic compositions of the present invention are administered to an individual in amounts effective to treat or diagnose human physiological disorders, neuroaffective disorders, and/or neurophysiological disorders that are associated with the KCNQ5 potassium channel, its biological activity or physiology. The effective amount may vary according to a variety of factors, such as the individual's condition, weight, sex and age. Other factors include the mode and route of administration. These factors are realized and understood by the skilled practitioner and are routinely taken into account when administering a therapeutic agent to an individual.

The term "chemical derivative" describes a molecule that contains additional chemical moieties which are not normally a part of the base molecule. Optimally, the chemical moieties do not affect the activity or function of the base molecule, e.g., hKCNQ5. Such moieties may improve the solubility, half-life, absorption, etc. of the base molecule. Alternatively the moieties may attenuate undesirable side effects of the base molecule or decrease the toxicity of the base molecule. Examples of such moieties are described in a number of texts available to the practitioner, such as *Remington's Pharmaceutical Sciences*.

Pharmaceutical compositions suitable for use in the present invention include compositions wherein the active ingredients are contained in an effective and sufficient amount to achieve the intended purpose. The determination of an effective dose is well within the capability of those skilled in the art. The therapeutically effective dose can be estimated initially either in cell culture assays, e.g., of neoplastic cells, or in animal models, usually mice, rabbits, dogs, pigs, rats, monkeys, or guinea pigs. The animal model is also used to achieve a desirable concentration range and route of administration. Such information can then be used to determine useful doses and routes for administration in humans. A therapeutically effective dose refers to that amount of the KCNQ5 protein or its antibodies, agonists (openers or activators), or antagonists, (inhibitors or blockers), which ameliorate, reduce or eliminate the symptoms or condition. The exact dosage is chosen by the individual physician in view of the patient to be treated, the route of administration, the severity of disease, and the like.

KNCQ5-modulatory compounds identified according to the methods disclosed herein may be used alone, at appropriate dosages defined by routine testing, in order to obtain optimal modulation of a potassium channel biological activity and/or physiological condition, or its activity while minimizing any potential toxicity. In addition, co-administration or sequential administration of other agents may be desirable.

The pharmaceutical compositions may be provided to an individual in need of therapeutic treatment by a variety of routes, such as subcutaneous, topical, oral, intraperitoneal, intradermal, intravenous, intranasal, rectal, and intramuscular. Administration of pharmaceutical compositions is accomplished orally or parenterally. More specifically, methods of parenteral delivery include topical, intra-arterial (directly to the tissue), intramuscular, subcutaneous, intramedullary, intrathecal, intraventricular, intravenous, intraperitoneal, or intranasal administration.

The present invention also provides suitable topical, oral, systemic and parenteral pharmaceutical formulations for use in the novel methods of treatment comprising the KCNQ5 potassium channel described herein. The compositions containing compounds identified according to described methods to be utilized as the active ingredient in modulating physiological, neurophysiological, or neuropsychological conditions can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, the modulatory compounds may also be administered in intravenous (both bolus and infusion), intraperitoneal, subcutaneous, topical—with or without occlusion, or intramuscular form, all using forms well known to those of ordinary skill in the pharmaceutical arts. An effective but non-toxic amount of the compound desired can be employed as a KCNQ5 potassium channel modulating agent.

The daily dosage of the products may be varied over a wide range, for example, from about 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the individual to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course, it will be understood by the skilled practitioner that the dosage level will vary depending upon the potency of the particular compound, and that certain compounds will be more potent than others.

In addition, the dosage level will vary depending upon the bioavailability of the compound. The more bioavailable and potent the compound, the less amount of the compound will need to be administered through any delivery route, including, but not limited to, oral delivery. The dosages of the KCNQ5 potassium channel modulators are adjusted when combined in order to achieve desired effects. On the other hand, dosages of the various agents or modulating compounds may be independently optimized and combined to achieve a synergistic result wherein the pathology is reduced more than it would be if one single agent or compound were used alone. Those skilled in the art will employ different formulations for nucleotides than for proteins or their inhibitors. Similarly, the delivery of polynucleotides or polypeptides will be specific to particular cells and conditions.

In another of its aspects, the present invention provides targeting therapies to deliver an active agent, such as a KCNQ5 protein modulator, or the KCNQ5 polypeptide, antibodies, peptides and nucleic acids of the present invention, more specifically to certain types of cells, for example, by the use of targeting systems such as antibodies or cell specific ligands. Targeting may be desirable for a variety of reasons, e.g., if an agent is unacceptably toxic, or if it would require too high a dosage, or if it would not otherwise be able to enter the target cells.

Rather than administering an active agent directly, the agent could be produced in the target cell, e.g., in a viral vector as described hereinabove, or in a cell-based delivery system, e.g., as described in U.S. Pat. No. 5,550,050, or published international application numbers WO 92/19195, WO 94/25503, WO 95/01203, WO 95/05452, WO 96/02286, WO 96/02646, WO 96/40871, WO 96/40959 and WO 97/12635, designed for implantation in a patient, i.e., an ex vivo type of therapy. The vector can be targeted to the specific cells to be treated, or it can contain regulatory elements which are more tissue specific to the target cells. The cell-based delivery system is designed to be administered to a patient, or implanted in a patient's body at the desired target site and contains a coding sequence for the active agent. Alternatively, the agent can be administered in a precursor form for conversion to the active form by an activating agent produced in, or targeted to, the cells to be treated (e.g., see, EP 425 731 A or WO 90/07936).

EXAMPLES

The following examples as set forth herein are meant to illustrate and exemplify the various aspects of carrying out the present invention and are not intended to limit the invention in any way.

Example 1

Bioinformatics Analysis

Human KCNQ2 and KCNQ3 sequences were used as probes to search public domain EST (expressed sequence tag) databases and proprietary Incyte EST databases. The DNA/protein database search program used was called gapped BLAST2 (Altschul et al., 1997, *Nucl. Acids Res.*, 25:3389–3402), ("BLAST—basic local alignment search tool"). The outputs from the BLAST search were analyzed for any heretofore unknown channel sequences. By means of the BLAST search, an Incyte #4970006 EST clone was found to correspond to a new channel, and thus was identified from the Incyte database. Bioinformatics analysis revealed homology to a portion of the KCNQ2 gene, thereby suggesting that the clone might be a novel member of KCNQ potassium channel family.

The Incyte #4970006 clone was fully sequenced and found to contain only a partial gene sequence. Although this clone showed a partial DNA and protein alignment to the KCNQ family (nt 1819–2121), most of the #4970006 clone sequence was hypothesized not to be part of the novel hKCNQ5 clone, based on lack of homology and 5' and 3' RACE experiments. Thus, primers were designed to amplify the short sequence (nt 1819–2121) from the bioinformatic similarity search using human brain tissue as the source nucleic acid. Polymerase chain reaction (PCR) was performed using Human Brain cDNA as a template (Clontech, Marathon-Ready) with primers designed against the region between nt 1819 and nt 2121 of clone #4970006. A "Q5" probe was prepared using the primers: Q5/sense (sense: 5' CTGGATAAGCAGCCACTGTTT 3'), (SEQ ID NO:22) and Q5/antisense (5' GCAGAACATGAGACCACAG 3'), (SEQ ID NO:23). Taq polymerase was used with the following cycling parameters: denaturation—94° C. for 1 minute, annealing—55° C. for 1 minute, and extension at 72° C. for 1 minute and 30 seconds, for a total of 35 cycles. The DNA product of 259 base pairs (bp) was the expected size and was ligated into the TA vector (pCR 2.1, Invitrogen). Miniprep DNA was analyzed and sequenced.

The sequencing results indicated that the 259 bp sequence was the same as that of the clone #4970006 between the two priming sites. This PCR product was then used as a probe to screen a human brain cDNA library (Clontech, λgt10). This 259 bp probe, the Q5 probe (150 ng DNA/150 μCi $^{32}$P-dCTP) was labeled using Ambion's DecaPrime II kit, denatured, and added to the hybridization solution at ~3–4× $10^6$ cpm/ ml. Specific activity of the probe was ~1–2×$10^9$ cpm/ug.

For library screening, twenty plates (150 mm) were screened for a total of $10^6$ pfu. Plates were lifted using Duralon-UV membranes (Stratagene). The DNA on the membranes was denatured in 1.5 M NaCl, 0.5 M NaOH for 2 minutes, then neutralized in 1.5 M NaCl, 5 M Tris-HCl, pH 8 for 5 minutes, and rinsed in 0.2 M Tris-HCl, pH 7.5, 2×SSC for 5 minutes at room temperature. DNA was UV-crosslinked onto the membranes at 0.5 joules. Hybridization of the membranes was overnight at 42° C. in 2× PIPES buffer, (i.e., 1,4-piperazine-diethane sulfonic acid), 50% formamide, 1% SDS with 100 μg/ml of denatured salmon testes DNA. Washes were carried out once in 1×SSC, 0.1% SDS for 15 minutes at room temperature, then 3× in 0.1×SSC, 0.1% SDS for 15–20 minutes each at 55° C. The membranes were exposed to film overnight at −70° C.

Following the screening procedure, fifteen initial positive signals were observed, and these plaques were cored from the agar plates, placed in Lambda Dilution Buffer, diluted, and secondary and/or tertiary screening were/was performed with the Q5 probe to isolate the positive plaques. Isolated plaques were cored, placed in dilution buffer, and PCR was performed on the supernatant with λgt10 forward and reverse primers (Forward primer: 5'-CTTTTGAGCAAGTTCAGCCTGGTTAAGT-3' (SEQ ID NO:24); Reverse primer: 5'-GAGGTGGCTTATGAGTATTTCTTCCAGGGTAA-3' (SEQ ID NO:25) to estimate the size of the inserts. DNA was isolated from plate lysates of the positive clones and purified using Promega's Wizard Lambda Prep kit. The DNA was enzymatically digested with EcoRI, and inserts were gel-purified using Clontech's Nucleotrap Kit. These inserts were then ligated into the vector pcDNA3.1 (+) Neo (Invitrogen).

With the full sequence known from the overlapping alignment, the polymerase chain reaction was used to amplify a full length clone from human Brain cDNA (Clontech). To amplify a full length product, the following primers were designed from the contiguous sequence: [Kozak start 5' GGATATCACCATGAAGGATGTGG 3'], (SEQ ID NO:26) and [Stop primer 5' AATCTAGAACT-TATTTCAGTTTGAC 3'], (SEQ ID NO:27). The following amplification parameters were used: denaturation at 94° C. for 30 sec, annealing at 55° C. for 30 seconds, and extension at 68° C. for 3 minutes for a total of 25 cycles. The 2694 bp PCR product was first cloned into pCR2.1 and confirmed by sequence analysis. The hKCNQ5 product was subcloned into pcDNA3.1(+) Neo for expression in mammalian cells and into pBS-KSM for expression in frog oocytes (the pBS-KSM vector has 5' and 3' Xenopus beta globin UTRs for increased expression in Xenopus oocytes).

Example 2

RNA Expression Blots

To determine the expression of hKCNQ5 mRNA in human tissues, dot blots and Northern blots were performed.

For carrying out the dot blot analyses, a Poly A+ RNA Master Blot (Clontech) was hybridized with the same 259 bp Q5 probe used to screen the Human Brain library. Hybridization was done at 65° C. overnight in ExpressHyb solution (Clontech) containing 100 ug/ml of denatured salmon testes DNA and denatured Q5 probe (50 ng DNA/50 uCi 32-P-dCTP) following the manufacturer's protocol. The blot was washed 5× for 20 minutes each at 65° C. in 2×SSC, 0.1% SDS, then 2× for 20 minutes each at 55° C. in 0.1×SSC, 0.5% SDS. The blot was exposed to XAR5 film at −70° C.

Figure 6B:
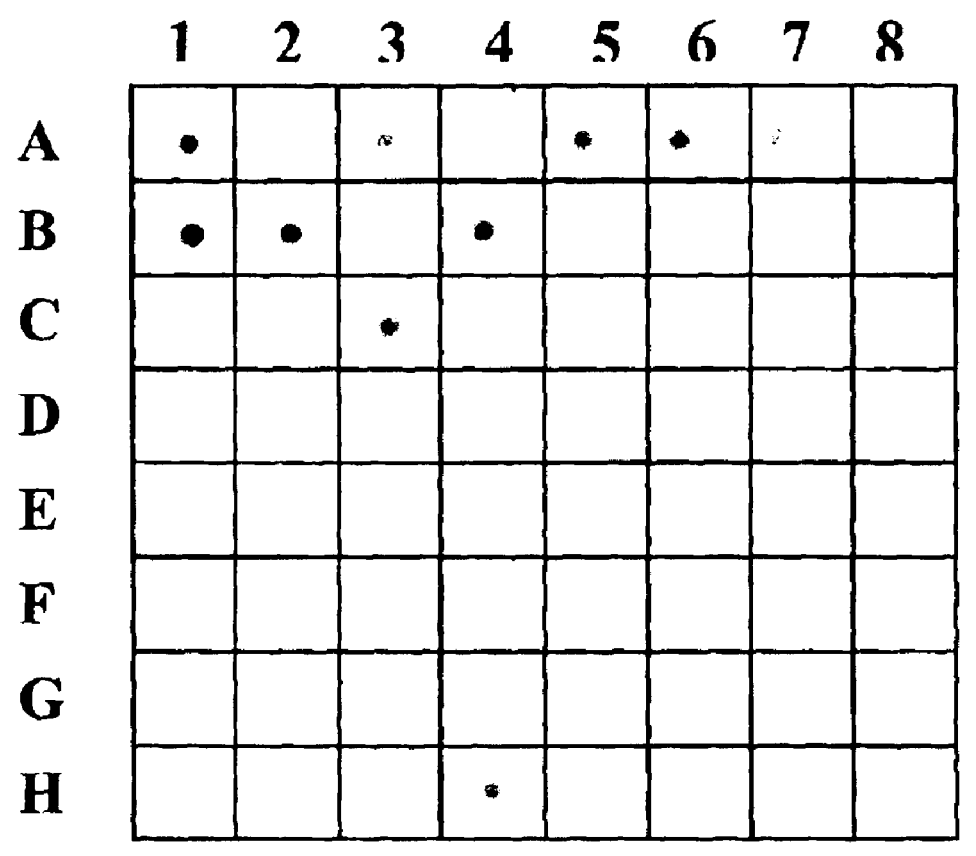

In the dot blot shown in FIGS. 6A and 6B, positive signals were observed in whole brain, as well as for subregions of the brain; including brain subregions including; caudate nucleus, cerebellum, hippocampus, cerebral cortex, frontal lobe, occipital pole, putamen, and temporal lobe. In addition to CNS tissue, skeletal muscle also gave a positive signal. No other tissues appeared to express the KCNQ5 mRNA.

A Human Multiple Tissue Northern blot (Clontech) was also probed for the presence of hKCNQ5 mRNA. Hybridization was for 1 hour at 68° C. in ExpressHyb solution containing 100 ug/ml of denatured salmon testes DNA and denatured labeled Q5 DNA as probe. The MTN blot was washed for 40 minutes at room temperature in 2×SSC, 0.05% SDS, with continuous agitation and several changes of fresh solution. The blot was then washed 3× in 0.1×SSC, 0.1% SDS at 50° C. with continuous agitation for 40 min. The blot was exposed overnight to XAR5 film at −70° C. The results are shown in FIGS. 6A and 6B.

Similar to the results observed from the dot blot, the human multiple tissue Northern blot revealed a restricted distribution of hKCNQ5 mRNA (FIG. 7). A strong signal was observed between 7–7.5 Kb for skeletal muscle with a smaller signal in human brain tissue. Although the differences in signal strength could be due to the differences in RNAs between the two blots, the results clearly show a restricted localization to brain tissue and skeletal muscle.

Example 3

In situ Hybridization

For performing the in situ hybridization studies as depicted in FIGS. 9A/F–18A/B, frozen 16 μm sections of rat DORG, trigeminal, or adult brain cut at intervals of 225 μm were fixed by immersion (without thawing) into ice cold 10% formaldehyde in phosphate buffered saline (PBS) for 20 minutes and rinsed with PBS. Fixed sections were treated with 0.5% Triton X-100 in 0.1 M Tris, pH 8.0, and 0.05 M EDTA for 30 minutes and rinsed for 3 minutes in 0.1 M Tris, pH 8.0, and 0.05 M EDTA. The tissue was then treated with 0.1 M TEA, pH 8.0, plus 0.25% acetic anhydride for 10 minutes at room temperature, rinsed (3×) in 2×SSC, dehydrated through a series of alcohols, delipidated in chloroform, and air dried.

Riboprobes were synthesized using the Promega Riboprobe Transcription System II (Promega, LOCATION?) with 250 μCi $^{35}$S-UTP and 250 μCi $^{35}$S-CTP in a total reaction volume of 10 μL. Unlabeled UTP and CTP were added at 25 μM each and ATP and GTP at 500 μM each. The human KCNQ5 plasmid (nts 1681–2032 subcloned into pGEM5zf(+)) was linearized with Spe I and transcribed using SP6 RNA polymerase, and with Not I and transcribed using T7 RNA polymerase to generate anti-sense and sense probes, respectively. One μg of linearized plasmid was added for each reaction. The riboprobes were purified by phenol:chloroform extraction and two ethanol precipitations using ammonium acetate. The dried tissue sections were hybridized with 1×10$^7$ cpm/ml riboprobe in hybridization buffer (50% formamide, 0.3 M NaCl, 10 mM Tris, 1 mM EDTA, 1× Denhardt's solution, 10% dextran sulfate, 500 μg/ml tRNA and 10 mM DTT) overnight at 54° C. The hybridization solution was removed by rinsing 4 times in 4×SSC, 5 minutes for each wash. The sections were incubated in 0.02 mg/ml RNase, 0.5 M NaCl, 10 mM Tris, pH 8.0, and 1 mM EDTA for 30 minutes at 37° C., then washed in 2×SSC, 1×SSC and 0.5×SSC, all containing 1 mM DTT, for 10 minutes per wash at room temperature. The tissues were incubated in 0.1×SSC, 1 mM DTT, and 20% formamide for 30 minutes at 50° C., then rinsed briefly in 0.1×SSC and 1 mM DTT at room temperature, dehydrated, and air dried. The dried sections were exposed to XOMAT film (Kodak, Rochester, N.Y.), then were dipped in NTB2 emulsion (Kodak, Rochester, N.Y.), developed after 2 weeks, and examined under the microscope to determine the cellular localization of each mRNA. Images were acquired using the NIH Image software.

A summary of the results of the expression of human KCNQ5 mRNA in brain by in situ hybridization is presented in Table 2:

TABLE 2

| KCNQ5 In situ Hybridization Results | |
|---|---|
| Region of Brain | Staining Intensity* |
| Cortex | + |
| Caudate Putamen | + |
| Piriform Cortex | ++ |
| Septohippocampal nuclei | + |
| CA2 Region of the Hippocampus | +/++ |
| CA3 Region of the Hippocampus | +/++ |
| Reticulotegmental Nuclei of the Pons | +/++ |
| Pontine Nuclei | + |
| Dorsal Root Ganglion | +(in 10–20% of neurons) |
| Trigeminal Ganglion | +(in 20–30% of neurons) |

*Intensity of labeling as examined microscopically was scored on a scale of + to +++++.

Example 4 hKCNQ5 Oocyte Expression and Electrophysiology

Frog (*Xenopus laevis*) oocytes were prepared and injected using standard techniques; each oocyte was injected with approximately 50 nl of hKCNQ5 cRNA. Following injection, oocytes were maintained at 17° C. in ND96 medium comprising (in mM): NaCl, 90; KCl, 1.0; CaCl$_2$, 1.0; MgCl$_2$, 1.0; HEPES, 5.0; pH 7.5. Horse serum (5%) and penicillin/streptomycin (5%) were added to the incubation medium. Recording commenced 2–6 days following mRNA injection. Prior to the start of an experiment, oocytes were placed in a recording chamber and incubated in Modified Barth's Solution (MBS) consisting of (in mM): NaCl, 88; NaHCO$_3$, 2.4; KCl, 1.0; HEPES, 10; MgSO$_4$, 0.82; Ca(NO$_3$)$_2$, 0.33; CaCl$_2$, 0.41; pH 7.5. Oocytes were impaled with electrodes (1–2 MΩ) and standard 2-electrode voltage clamp techniques were employed to record whole-cell membrane currents. Voltage-clamp protocols typically consisted of a series of voltage steps 1–5 second duration, in +10 mV steps from a holding potential of −90 mV to a maximal potential of +40 mV; records were digitized at 5 kHz and stored on a computer using pClamp data acquisition and analysis software (Axon Instruments).

Figure 8:
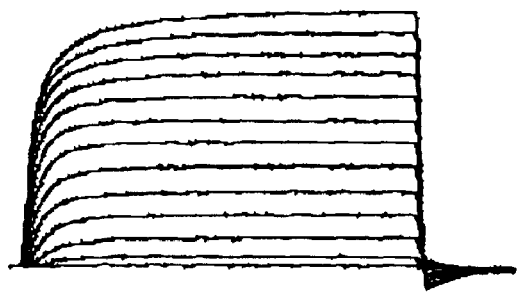
FIG. 8 shows that expression of hKCNQ5 in Xenopus oocytes results in large non-activating outward currents that are resistant to blockage by triethylammonium (TEA) at high concentrations. (Example 3).
Figure 8:
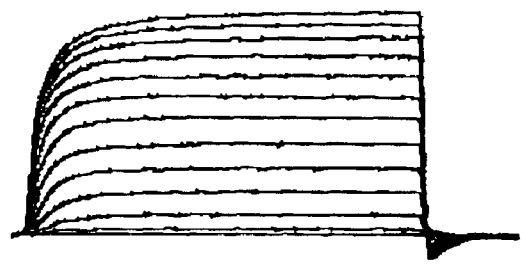
Figure 11:
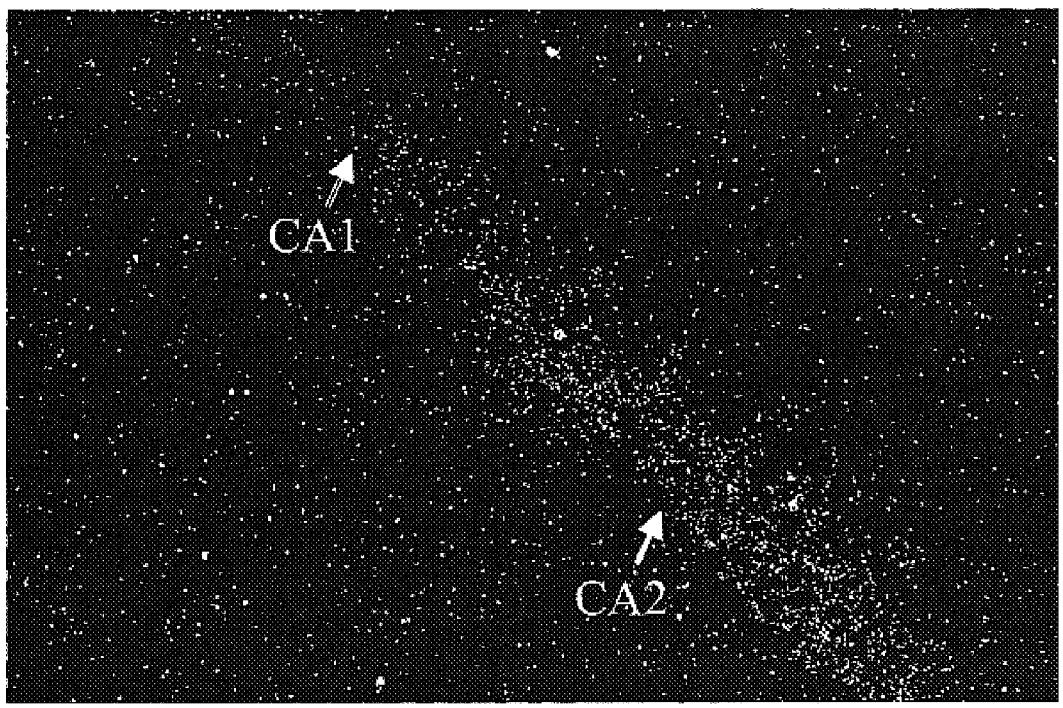
FIG. 11 depicts dark field image of emulsion dipped slides showing that the expression of KCNQ5 mRNA is present in the CA2 region, but absent in the CA1 region of the hippocampus.
Figure 14A:
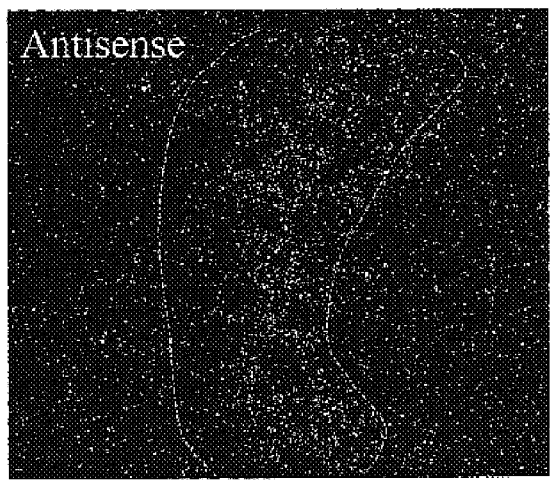
FIGS. 14A and 14B depict dark field images of emulsion dipped slides showing the expression of KCNQ5 mRNA in the septohippocampal nucleus. Hybridization with the antisense riboprobe shows a weak signal (FIG. 14A), which is absent with the sense riboprobe (FIG. 14B).
Figure 14B:
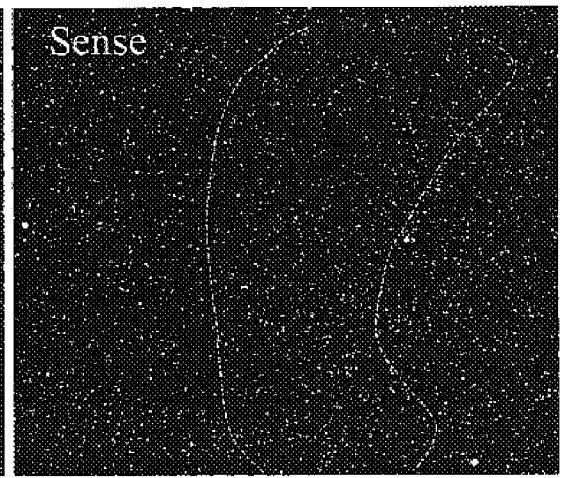
Figure 16A:
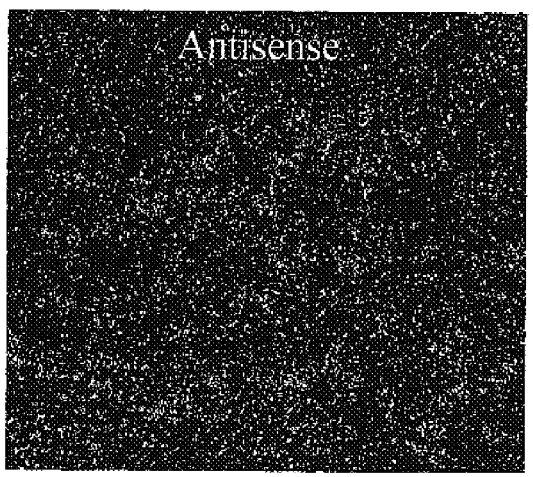
FIGS. 16A and 16B depict dark field images of emulsion dipped slides showing the expression of KCNQ5 mRNA in the pontine nuclei. Hybridization with the antisense riboprobe shows a weak signal (FIG. 16A), which is absent with the sense riboprobe (FIG. 16B).
Figure 16B:
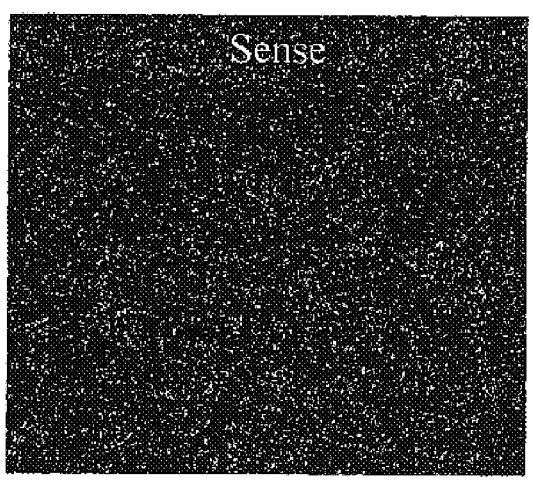
Figure 17A:
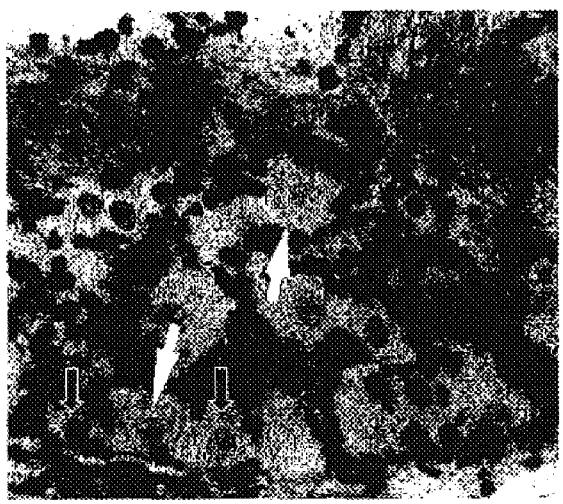
FIGS. 17A and 17B depict bright field (FIG. 17A) and dark field (FIG. 17B) images of emulsion dipped slides showing the expression of KCNQ5 mRNA in the dorsal root ganglion (DRG). Hybridization with the antisense riboprobe shows a weak signal in about 20–30% of the neurons (large white arrows), (FIG. 17B) which is absent in other neurons (smaller black arrows), (FIG. 17B).
Figure 17B:
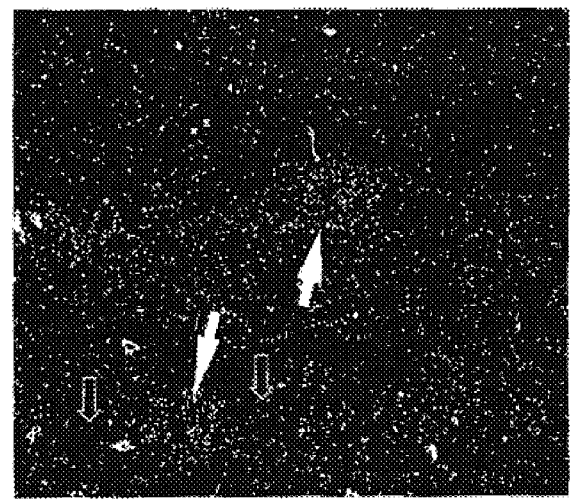
Figure 18A:
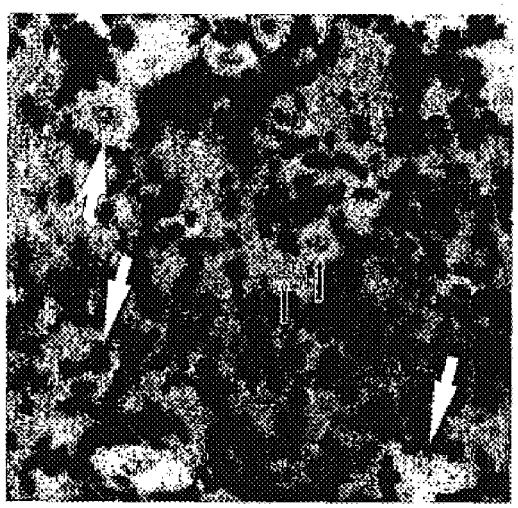
FIGS. 18A and 18B depict bright field (FIG. 18A) and dark field (FIG. 18B) images of emulsion dipped slides showing the expression of KCNQ5 mRNA in the trigeminal ganglion. Hybridization with the antisense riboprobe shows a weak signal in about 20–30% of the neurons (large white arrows), (FIG. 18B), which is absent in other neurons (smaller, white-outlined arrows).
Figure 18B:
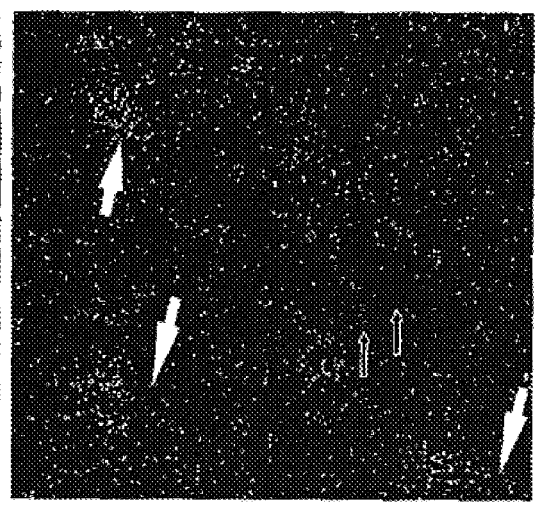

As demonstrated in FIG. 8, the injection of hKCNQ5 cRNA into Xenopus oocytes resulted in robust expression of large outward currents under the recording conditions employed in these experiments. Currents appeared similar to those obtained by the expression of KCNQ2 channels; currents were slowly activating, non-inactivating at positive voltage steps over a period of seconds, and deactivated with a time course similar to the current activation. However, unlike the KCNQ2 currents, the hKCNQ5 currents were largely resistant to the potassium channel blocker tetraethylammonium (TEA), even at concentrations as high as 30 mM.

These results indicated that expression of the hKCNQ5 construct in oocytes produced robust expression of large outward currents similar to those seen with KCNQ2 expression, but with a different pharmacology. Injection of equivalent amounts of water (50 nl) did not result in expression of outward currents at the voltage steps used to detect KCNQ5 expression.

Example 5

Ligand Binding Assay for High Throughput Screening for hKCNQ5 Modulators

Cell lines that over-express the heterologous KCNQ5 potassium channel coding region described herein (SEQ ID NO:1), or a biologically active fragment or truncated portion thereof, or a chimeric or fusion protein, are used in binding assays to identify and screen for pharmacologically active molecules that block hKCNQ5 activity.

A radiolabeled binding assay using a radiolabeled ligand is employed (Hill, R. J., 1995, *Mol. Pharm.*, 48:98 and Deutsch, C. et al., 1991, *J. Biol. Chem.*, 266:3668). Membrane preparations of cell lines that over-express the KCNQ5 potassium channel are made by homogenizing the cells using a Polytron for 25 seconds at 13,000 rpm and centrifuged at 100×g for 2 minutes. The pellet is suspended in 1 ml of assay buffer (5 mM NaCl, 5 mM KCl, 10 mM HEPES, 6 mM glucose, pH 8.4) and diluted to 50 µg/ml.

To each of the wells of a 96-well microtiter plate, 130 µl of assay buffer is added, along with 20 µl of test compound or drug (the test compound or drug may be a small molecule, peptide, analog, or mimetic agent), control assay buffer, non-specific, unlabeled ligand (10 nM), 50 µl of membranes from cells over-expressing KCNQ5 potassium channel at 50 µg/ml, and 50 µl of radioligand (25 pM; NEN, 2200 Ci/mmol). The plates are incubated for 20 minutes at 21° C. with mixing. Bound radiolabeled ligand is separated from free radiolabeled ligand in solution by filtration over presoaked GF/C Unifilters (Packard Instruments) and washed rapidly in ice-cold wash buffer. Upon drying, scintillation fluid is added and the filter plates are scintillation counted. Data from saturation experiments are subjected to Scatchard analysis and linear regression. (Deutsch, C. et al., 1991, *J. Biol. Chem.*, 266:3668). Compounds that compete with the radiolabeled ligand for binding the novel KCNQ5 potassium channel are identified via the production of a reduction in specific counts. Alternatively, a scintillation proximity assay (SPA) can be used so as to eliminate the need for filters. SPA is easily adapted for high throughput screening assays (Hoffman, R. et al., 1992, *Anal. Biochem.*, 29:370; Kienuis, C. B. M. et al., 1992, *J. Recept. Res.*, 12:389).

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. An isolated nucleic acid molecule encoding a human KCNQ5 potassium channel polypeptide and having a contiguous nucleotide sequence that encodes the amino acid sequence set forth in SEQ ID NO:2.

2. A vector comprising the nucleic acid molecule according to claim 1.

3. An isolated cell comprising the vector according to claim 2.

4. An isolated nucleic acid molecule, wherein the sequence of said nucleic acid molecule is identical to the sequence in ATCC Deposit No. PTA-1924 (human KCNQ5).

* * * * *

SEQUENCE LISTING

```
<160> NUMBER OF SEQ ID NOS: 31

<210> SEQ ID NO 1
<211> LENGTH: 2694
<212> TYPE: DNA
<213> ORGANISM: Homo sapiens

<400> SEQUENCE: 1
atgaaggatg tggagtcggg ccggggcagg gtgctgctga actcggcagc cgccaggggc       60
gacggcctgc tactgctggg cacccgcgcg gccacgcttg gtggcggcgg cggtggcctg      120
agggagagcc gccggggcaa gcaggggggcc cggatgagcc tgctggggaa gccgctctct      180
tacacgagta gccagagctg ccggcgcaac gtcaagtacc ggcgggtgca gaactacctg      240
tacaacgtgc tggagagacc ccgcggctgg gcgttcatct accacgcttt cgttttttctc      300 cttgtctttg gttgcttgat tttgtcagtg ttttctacca tccctgagca cacaaaattg      360
gcctcaagtt gcctcttgat cctggagttc gtgatgattg tcgtctttgg tttggagttc      420
atcattcgaa tctggtctgc gggttgctgt tgtcgatata gaggatggca aggaagactg      480
aggtttgctc gaaagcccttt ctgtgttata gataccattg ttcttatcgc ttcaatagca      540
gttgtttctg caaaaactca gggtaatatt tttgccacgt ctgcactcag aagtctccgt      600
ttcctacaga tcctccgcat ggtgcgcatg gaccgaaggg gaggcacttg gaaattactg      660
ggttcagtgg tttatgctca cagcaaggaa ttaatcacag cttggtacat aggattttttg      720 gttcttattt tttcgtctttt ccttgtctat ctggtggaaa aggatgccaa taaagagttt      780
tctacatatg cagatgctct ctggtggggc acaattacat tgacaactat tggctatgga      840
```

-continued

```
gacaaaactc ccctaacttg gctgggaaga ttgctttctg caggctttgc actccttggc    900
atttctttct ttgcacttcc tgccggcatt cttggctcag gttttgcatt aaaagtacaa    960
gaacaacacc gccagaaaca ctttgagaaa agaaggaacc cagctgccaa cctcattcag   1020
tgtgtttggc gtagttacgc agctgatgag aaatctgttt ccattgcaac ctggaagcca   1080
cacttgaagg ccttgcacac ctgcagccct accaagaaag aacaagggga agcatcaagc   1140
agtcagaagc taagttttaa ggagcgagtg cgcatggcta gccccagggg ccagagtatt   1200
aagagccgac aagcctcagt aggtgacagg aggtccccaa gcaccgacat acagccgag    1260
ggcagtccca ccaaagtgca aagagctgg agcttcaacg accgaacccg cttccggccc    1320
tcgctgcgcc tcaaaagttc tcagccaaaa ccagtgatag atgctgacac agcccttggc   1380
actgatgatg tatatgatga aaaaggatgc cagtgtgatg tatcagtgga agacctcacc   1440
ccaccactta aaactgtcat tcgagctatc agaattatga aatttcatgt tgcaaaacgg   1500
aagtttaagg aaacgttacg tccatatgat gtaaaagatg tcattgaaca atattctgct   1560
ggtcatctgg acatgttgtg tagaattaaa agccttcaaa cacgtgttga tcaaattctt   1620
ggaaagggc aaatcacatc agataagaag agccgagaga aaataacagc agaacatgag    1680
accacagacg atctcagtat gctcggtcgg gtggtcaagg ttgaaaaaca ggtacagtcc   1740
atagagtcca agctggactg cctactagac atctatcaac aggtccttcg gaaaggctct   1800
gcctcagccc tcgctttggc ttcattccag atcccaccct ttgaatgtga acagacatct   1860
gactatcaaa gccctgtgga tagcaaagat ctttcgggtt ccgcacaaaa cagtggctgc   1920
ttatccagat caactagtgc caacatctcg agaggcctgc agttcattct gacgccaaat   1980
gagttcagtg cccagacttt ctacgcgctt agccctacta tgcacagtca agcaacacag   2040
gtgccaatta gtcaaagcga tggctcagca gtggcagcca ccaacaccat tgcaaaccaa   2100
ataaatacgg cacccaagcc agcagccca acaactttac agatcccacc tcctctccca   2160
gccatcaagc atctgcccag gccagaaact ctgcacccta accctgcagg cttacaggaa   2220
agcatttctg acgtcaccac ctgccttgtt gcctccaagg aaaatgttca ggttgcacag   2280
tcaaatctca ccaaggaccg ttctatgagg aaaagctttg acatgggagg agaaactctg   2340
ttgtctgtct gtcccatggt gccgaaggac ttgggcaaat ctttgtctgt gcaaaacctg   2400
atcaggtcga ccgaggaact gaatatacaa ctttcaggga gtgagtcaag tggctccaga   2460
ggcagccaag atttttaccc caaatggagg gaatccaaat gtttataac tgatgaagag    2520
gtgggtcccg aagagacaga gacagacact tttgatgccg caccgcagcc tgccagggaa   2580
gctgcctttg catcagactc tctaaggact ggaaggtcac gatcatctca gagcatttgt   2640
aaggcaggag aaagtacaga tgccctcagc ttgcctcatg tcaaactgaa ataa         2694
```

<210> SEQ ID NO 2
<211> LENGTH: 897
<212> TYPE: PRT
<213> ORGANISM: Homo sapiens

<400> SEQUENCE: 2

```
Met Lys Asp Val Glu Ser Gly Arg Gly Arg Val Leu Leu Asn Ser Ala
  1               5                  10                  15

Ala Ala Arg Gly Asp Gly Leu Leu Leu Gly Thr Arg Ala Ala Thr
             20                  25                  30

Leu Gly Gly Gly Gly Gly Gly Leu Arg Glu Ser Arg Arg Gly Lys Gln
         35                  40                  45
```

-continued

```
Gly Ala Arg Met Ser Leu Leu Gly Lys Pro Leu Ser Tyr Thr Ser Ser
         50                  55                  60

Gln Ser Cys Arg Arg Asn Val Lys Tyr Arg Arg Val Gln Asn Tyr Leu
 65                  70                  75                  80

Tyr Asn Val Leu Glu Arg Pro Arg Gly Trp Ala Phe Ile Tyr His Ala
                 85                  90                  95

Phe Val Phe Leu Val Phe Gly Cys Leu Ile Leu Ser Val Phe Ser
             100                 105                 110

Thr Ile Pro Glu His Thr Lys Leu Ala Ser Ser Cys Leu Leu Ile Leu
             115                 120                 125

Glu Phe Val Met Ile Val Val Phe Gly Leu Glu Phe Ile Ile Arg Ile
         130                 135                 140

Trp Ser Ala Gly Cys Cys Cys Arg Tyr Arg Gly Trp Gln Gly Arg Leu
145                 150                 155                 160

Arg Phe Ala Arg Lys Pro Phe Cys Val Ile Asp Thr Ile Val Leu Ile
                 165                 170                 175

Ala Ser Ile Ala Val Val Ser Ala Lys Thr Gln Gly Asn Ile Phe Ala
             180                 185                 190

Thr Ser Ala Leu Arg Ser Leu Arg Phe Leu Gln Ile Leu Arg Met Val
         195                 200                 205

Arg Met Asp Arg Arg Gly Gly Thr Trp Lys Leu Leu Gly Ser Val Val
    210                 215                 220

Tyr Ala His Ser Lys Glu Leu Ile Thr Ala Trp Tyr Ile Gly Phe Leu
225                 230                 235                 240

Val Leu Ile Phe Ser Ser Phe Leu Val Tyr Leu Val Glu Lys Asp Ala
                 245                 250                 255

Asn Lys Glu Phe Ser Thr Tyr Ala Asp Ala Leu Trp Trp Gly Thr Ile
             260                 265                 270

Thr Leu Thr Thr Ile Gly Tyr Gly Asp Lys Thr Pro Leu Thr Trp Leu
         275                 280                 285

Gly Arg Leu Leu Ser Ala Gly Phe Ala Leu Leu Gly Ile Ser Phe Phe
    290                 295                 300

Ala Leu Pro Ala Gly Ile Leu Gly Ser Gly Phe Ala Leu Lys Val Gln
305                 310                 315                 320

Glu Gln His Arg Gln Lys His Phe Glu Lys Arg Arg Asn Pro Ala Ala
                 325                 330                 335

Asn Leu Ile Gln Cys Val Trp Arg Ser Tyr Ala Ala Asp Glu Lys Ser
             340                 345                 350

Val Ser Ile Ala Thr Trp Lys Pro His Leu Lys Ala Leu His Thr Cys
         355                 360                 365

Ser Pro Thr Lys Lys Glu Gln Gly Glu Ala Ser Ser Ser Gln Lys Leu
    370                 375                 380

Ser Phe Lys Glu Arg Val Arg Met Ala Ser Pro Arg Gly Gln Ser Ile
385                 390                 395                 400

Lys Ser Arg Gln Ala Ser Val Gly Asp Arg Arg Ser Pro Ser Thr Asp
                 405                 410                 415

Ile Thr Ala Glu Gly Ser Pro Thr Lys Val Gln Lys Ser Trp Ser Phe
             420                 425                 430

Asn Asp Arg Thr Arg Phe Arg Pro Ser Leu Arg Leu Lys Ser Ser Gln
         435                 440                 445

Pro Lys Pro Val Ile Asp Ala Asp Thr Ala Leu Gly Thr Asp Asp Val
    450                 455                 460
```

-continued

```
Tyr Asp Glu Lys Gly Cys Gln Cys Asp Val Ser Val Glu Asp Leu Thr
465                 470                 475                 480

Pro Pro Leu Lys Thr Val Ile Arg Ala Ile Arg Ile Met Lys Phe His
            485                 490                 495

Val Ala Lys Arg Lys Phe Lys Glu Thr Leu Arg Pro Tyr Asp Val Lys
        500                 505                 510

Asp Val Ile Glu Gln Tyr Ser Ala Gly His Leu Asp Met Leu Cys Arg
    515                 520                 525

Ile Lys Ser Leu Gln Thr Arg Val Asp Gln Ile Leu Gly Lys Gly Gln
    530                 535                 540

Ile Thr Ser Asp Lys Lys Ser Arg Glu Lys Ile Thr Ala Glu His Glu
545                 550                 555                 560

Thr Thr Asp Asp Leu Ser Met Leu Gly Arg Val Val Lys Val Glu Lys
            565                 570                 575

Gln Val Gln Ser Ile Glu Ser Lys Leu Asp Cys Leu Leu Asp Ile Tyr
        580                 585                 590

Gln Gln Val Leu Arg Lys Gly Ser Ala Ser Leu Ala Leu Ala Ser
    595                 600                 605

Phe Gln Ile Pro Pro Phe Glu Cys Glu Gln Thr Ser Asp Tyr Gln Ser
610                 615                 620

Pro Val Asp Ser Lys Asp Leu Ser Gly Ser Ala Gln Asn Ser Gly Cys
625                 630                 635                 640

Leu Ser Arg Ser Thr Ser Ala Asn Ile Ser Arg Gly Leu Gln Phe Ile
            645                 650                 655

Leu Thr Pro Asn Glu Phe Ser Ala Gln Thr Phe Tyr Ala Leu Ser Pro
        660                 665                 670

Thr Met His Ser Gln Ala Thr Gln Val Pro Ile Ser Gln Ser Asp Gly
    675                 680                 685

Ser Ala Val Ala Ala Thr Asn Thr Ile Ala Asn Gln Ile Asn Thr Ala
690                 695                 700

Pro Lys Pro Ala Ala Pro Thr Thr Leu Gln Ile Pro Pro Leu Pro
705                 710                 715                 720

Ala Ile Lys His Leu Pro Arg Pro Glu Thr Leu His Pro Asn Pro Ala
            725                 730                 735

Gly Leu Gln Glu Ser Ile Ser Asp Val Thr Thr Cys Leu Val Ala Ser
        740                 745                 750

Lys Glu Asn Val Gln Val Ala Gln Ser Asn Leu Thr Lys Asp Arg Ser
    755                 760                 765

Met Arg Lys Ser Phe Asp Met Gly Gly Glu Thr Leu Leu Ser Val Cys
770                 775                 780

Pro Met Val Pro Lys Asp Leu Gly Lys Ser Leu Ser Val Gln Asn Leu
785                 790                 795                 800

Ile Arg Ser Thr Glu Glu Leu Asn Ile Gln Leu Ser Gly Ser Glu Ser
            805                 810                 815

Ser Gly Ser Arg Gly Ser Gln Asp Phe Tyr Pro Lys Trp Arg Glu Ser
        820                 825                 830

Lys Leu Phe Ile Thr Asp Glu Val Gly Pro Glu Thr Glu Thr
    835                 840                 845

Asp Thr Phe Asp Ala Ala Pro Gln Pro Ala Arg Glu Ala Ala Phe Ala
850                 855                 860

Ser Asp Ser Leu Arg Thr Gly Arg Ser Arg Ser Gln Ser Ile Cys
865                 870                 875                 880

Lys Ala Gly Glu Ser Thr Asp Ala Leu Ser Leu Pro His Val Lys Leu
```

Lys

<210> SEQ ID NO 3
<211> LENGTH: 21
<212> TYPE: DNA
<213> ORGANISM: Homo sapiens
<220> FEATURE:
<221> NAME/KEY: exon
<222> LOCATION: (1)..(21)
<221> NAME/KEY: CDS
<222> LOCATION: (1)..(21)

<400> SEQUENCE: 3

```
tgg gga cag tgg aca ttg cgt                                               21
Trp Gly Gln Trp Thr Leu Arg
 1               5
```

<210> SEQ ID NO 4
<211> LENGTH: 7
<212> TYPE: PRT
<213> ORGANISM: Homo sapiens

<400> SEQUENCE: 4

```
Trp Gly Gln Trp Thr Leu Arg
 1               5
```

<210> SEQ ID NO 5
<211> LENGTH: 1090
<212> TYPE: DNA
<213> ORGANISM: Homo sapiens
<220> FEATURE:
<221> NAME/KEY: 3'UTR
<222> LOCATION: (1)..(1090)

<400> SEQUENCE: 5

| | | | | | |
|---|---|---|---|---|---|
| gttcttcatt | ttctttccag | gcatagcagt | tctttagcca | tacatatcat | tgcatgaact | 60 |
| atttcgaaag | cccttctaaa | agttgaaat | tgcaagaatc | gggaagaaca | tgaaaggcag | 120 |
| tttataagcc | cgttaccttt | taattgcatg | aaaatgcatg | tttagggatg | gctaaaattc | 180 |
| caaggtgcat | cgacattaac | ccactcattt | agtaatgtac | cttgagttaa | aaagcctgag | 240 |
| aaaccaaaca | cagctaatgc | tatggggtgt | atgaatatgt | caagtttagg | tcatttagaa | 300 |
| gatttgacac | tgtattttga | aattatgagt | aaacaccttc | aaatttcagg | catttctgct | 360 |
| ttgtgactaa | atacaaacta | cattttcaag | attaggccat | aatgtatatt | taaacacaat | 420 |
| ggctatcaac | agctgctaat | aaggtatcaa | ctaaagcaga | attggggaat | aatagaaatg | 480 |
| gctgcttatt | tcaagatata | tttgccaacc | cattcctatt | cagtcatttt | attattaatg | 540 |
| taatttgaat | gtcaatttgt | gtgcttttgg | tgatttagcg | ctgtggcaag | caattttgca | 600 |
| catcattttc | atgttgttct | ttatgacaag | aatgttcttc | aattagaaaa | tgtgcaaata | 660 |
| atgaaattca | gggccagtga | ggcaaataga | ctatctgaca | tatttgactt | tatgaaaaca | 720 |
| tattgcctga | tggcagaatc | aactttataa | gtggtcaact | tctacacaag | cgtatgaaat | 780 |
| actggtcagt | agaacagcca | ttgtgattgg | actggtttct | ctgcaatggc | gccaacccca | 840 |
| ggcttgccaa | tactgcctat | gtaaagggca | agtgtgagaa | gctattctca | tttcgctgac | 900 |
| atacaggtag | gactatgggg | gatgggacat | tgagtggga | ctgagatagg | aaaggcttga | 960 |
| aaagaaccca | gaaacaccac | caggaagttg | gcaaagtaaa | agaaaatgac | ttccccctca | 1020 |
| aagggcaatg | agagggagag | aaacaaacca | aaatagaaga | actagacttt | ttagaaaatg | 1080 |

-continued agtattgcta                                                             1090

<210> SEQ ID NO 6
<211> LENGTH: 18
<212> TYPE: PRT
<213> ORGANISM: Homo sapiens

<400> SEQUENCE: 6

Gly Gly Gly Gly Gly Gly Leu Arg Glu Ser Arg Arg Gly Lys Gln Gly
 1               5                  10                  15

Ala Arg

<210> SEQ ID NO 7
<211> LENGTH: 23
<212> TYPE: PRT
<213> ORGANISM: Homo sapiens

<400> SEQUENCE: 7

Pro Leu Ser Tyr Thr Ser Ser Gln Ser Cys Arg Arg Asn Val Lys Tyr
 1               5                  10                  15

Arg Arg Val Gln Asn Tyr Leu
             20

<210> SEQ ID NO 8
<211> LENGTH: 16
<212> TYPE: PRT
<213> ORGANISM: Homo sapiens

<400> SEQUENCE: 8

Cys Arg Tyr Arg Gly Trp Gln Gly Arg Leu Arg Phe Ala Arg Lys Pro
 1               5                  10                  15

<210> SEQ ID NO 9
<211> LENGTH: 11
<212> TYPE: PRT
<213> ORGANISM: Homo sapiens

<400> SEQUENCE: 9

Val Glu Lys Asp Ala Asn Lys Glu Phe Ser Thr
 1               5                  10

<210> SEQ ID NO 10
<211> LENGTH: 17
<212> TYPE: PRT
<213> ORGANISM: Homo sapiens

<400> SEQUENCE: 10

Val Gln Glu Gln His Arg Gln Lys His Phe Glu Lys Arg Arg Asn Pro
 1               5                  10                  15

Ala

<210> SEQ ID NO 11
<211> LENGTH: 88
<212> TYPE: PRT
<213> ORGANISM: Homo sapiens

<400> SEQUENCE: 11

His Thr Cys Ser Pro Thr Lys Lys Glu Gln Gly Glu Ala Ser Ser Ser
 1               5                  10                  15

Gln Lys Leu Ser Phe Lys Glu Arg Val Arg Met Ala Ser Pro Arg Gly
             20                  25                  30

Gln Ser Ile Lys Ser Arg Gln Ala Ser Val Gly Asp Arg Arg Ser Pro

```
                  35                  40                  45
Ser Thr Asp Ile Thr Ala Glu Gly Ser Pro Thr Lys Val Gln Lys Ser
         50                  55                  60

Trp Ser Phe Asn Asp Arg Thr Arg Phe Arg Pro Ser Leu Arg Leu Lys
 65                  70                  75                  80

Ser Ser Gln Pro Lys Pro Val Ile
                 85

<210> SEQ ID NO 12
<211> LENGTH: 13
<212> TYPE: PRT
<213> ORGANISM: Homo sapiens

<400> SEQUENCE: 12

Leu Gly Thr Asp Asp Val Tyr Asp Glu Lys Gly Cys Gln
 1               5                  10

<210> SEQ ID NO 13
<211> LENGTH: 16
<212> TYPE: PRT
<213> ORGANISM: Homo sapiens

<400> SEQUENCE: 13

His Val Ala Lys Arg Lys Phe Lys Glu Thr Leu Arg Pro Tyr Asp Val
 1               5                  10                  15

<210> SEQ ID NO 14
<211> LENGTH: 25
<212> TYPE: PRT
<213> ORGANISM: Homo sapiens

<400> SEQUENCE: 14

Leu Gly Lys Gly Gln Ile Thr Ser Asp Lys Lys Ser Arg Glu Lys Ile
 1               5                  10                  15

Thr Ala Glu His Glu Thr Thr Asp Asp
                 20                  25

<210> SEQ ID NO 15
<211> LENGTH: 13
<212> TYPE: PRT
<213> ORGANISM: Homo sapiens

<400> SEQUENCE: 15

Lys Val Glu Lys Gln Val Gln Ser Ile Glu Ser Lys Leu
 1               5                  10

<210> SEQ ID NO 16
<211> LENGTH: 41
<212> TYPE: PRT
<213> ORGANISM: Homo sapiens

<400> SEQUENCE: 16

Pro Pro Phe Glu Cys Glu Gln Thr Ser Asp Tyr Gln Ser Pro Val Asp
 1               5                  10                  15
Ser Lys Asp Leu Ser Gly Ser Ala Gln Asn Ser Gly Cys Leu Ser Arg
                 20                  25                  30
Ser Thr Ser Ala Asn Ile Ser Arg Gly
         35                  40

<210> SEQ ID NO 17
<211> LENGTH: 14
<212> TYPE: PRT
<213> ORGANISM: Homo sapiens
```

```
<400> SEQUENCE: 17

Thr Ile Ala Asn Gln Ile Asn Thr Ala Pro Lys Pro Ala Ala
1               5                   10

<210> SEQ ID NO 18
<211> LENGTH: 16
<212> TYPE: PRT
<213> ORGANISM: Homo sapiens

<400> SEQUENCE: 18

Lys His Leu Pro Arg Pro Glu Thr Leu His Pro Asn Pro Ala Gly Leu
1               5                   10                  15

<210> SEQ ID NO 19
<211> LENGTH: 26
<212> TYPE: PRT
<213> ORGANISM: Homo sapiens

<400> SEQUENCE: 19

Ser Lys Glu Asn Val Gln Val Ala Gln Ser Asn Leu Thr Lys Asp Arg
1               5                   10                  15

Ser Met Arg Lys Ser Phe Asp Met Gly Gly
            20                  25

<210> SEQ ID NO 20
<211> LENGTH: 23
<212> TYPE: PRT
<213> ORGANISM: Homo sapiens

<400> SEQUENCE: 20

Leu Ser Gly Ser Glu Ser Ser Gly Ser Arg Gly Ser Gln Asp Phe Tyr
1               5                   10                  15

Pro Lys Trp Arg Glu Ser Lys
            20

<210> SEQ ID NO 21
<211> LENGTH: 22
<212> TYPE: PRT
<213> ORGANISM: Homo sapiens

<400> SEQUENCE: 21

Glu Glu Val Gly Pro Glu Glu Thr Glu Thr Asp Thr Phe Asp Ala Ala
1               5                   10                  15

Pro Gln Pro Ala Arg Glu
            20

<210> SEQ ID NO 22
<211> LENGTH: 15
<212> TYPE: PRT
<213> ORGANISM: Homo sapiens

<400> SEQUENCE: 22

Asp Ser Leu Arg Thr Gly Arg Ser Arg Ser Ser Gln Ser Ile Cys
1               5                   10                  15

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: SYNTHETIC
      Q5 SENSE PRIMER

<400> SEQUENCE: 23
```
ctggataagc agccactgtt t                                               21

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: SYNTHETIC
      Q5 ANTISENSE PRIMER

<400> SEQUENCE: 24
gcagaacatg agaccacag                                                  19

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: SYNTHETIC
      FORWARD PRIMER

<400> SEQUENCE: 25
cttttgagca agttcagcct ggttaagt                                        28

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: SYNTHETIC
      REVERSE PRIMER

<400> SEQUENCE: 26
gaggtggctt atgagtattt cttccagggt aa                                   32

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      KOZAK START PRIMER

<400> SEQUENCE: 27
ggatatcacc atgaaggatg tgg                                             23

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: SYNTHETIC
      STOP PRIMER

<400> SEQUENCE: 28
aatctagaac ttatttcagt ttgac                                           25

<210> SEQ ID NO 29
<211> LENGTH: 676
<212> TYPE: PRT
<213> ORGANISM: Homo sapiens

<400> SEQUENCE: 29

Met Ala Ala Ala Ser Ser Pro Pro Arg Ala Glu Arg Lys Arg Trp Gly
  1               5                  10                  15

-continued

```
Trp Gly Arg Leu Pro Gly Ala Arg Arg Gly Ser Ala Gly Leu Ala Lys
            20                  25              30

Lys Cys Pro Phe Ser Leu Glu Leu Ala Glu Gly Gly Pro Ala Gly Gly
        35                  40              45

Ala Leu Tyr Ala Pro Ile Ala Pro Gly Ala Pro Gly Pro Ala Pro Pro
    50                  55              60

Ala Ser Pro Ala Ala Pro Ala Ala Pro Pro Val Ala Ser Asp Leu Gly
65                  70              75                  80

Pro Arg Pro Pro Val Ser Leu Asp Pro Arg Val Ser Ile Tyr Ser Thr
                85                  90              95

Arg Arg Pro Val Leu Ala Arg Thr His Val Gln Gly Arg Val Tyr Asn
            100                 105             110

Phe Leu Glu Arg Pro Thr Gly Trp Lys Cys Phe Val Tyr His Phe Ala
        115                 120             125

Val Phe Leu Ile Val Leu Val Cys Leu Ile Phe Ser Val Leu Ser Thr
    130                 135             140

Ile Glu Gln Tyr Ala Ala Leu Ala Thr Gly Thr Leu Phe Trp Met Glu
145                 150             155                 160

Ile Val Leu Val Val Phe Phe Gly Thr Glu Tyr Val Val Arg Leu Trp
                165                 170             175

Ser Ala Gly Cys Arg Ser Lys Tyr Val Gly Leu Trp Gly Arg Leu Arg
            180                 185             190

Phe Ala Arg Lys Pro Ile Ser Ile Ile Asp Leu Ile Val Val Val Ala
        195                 200             205

Ser Met Val Val Leu Cys Val Gly Ser Lys Gly Gln Val Phe Ala Thr
    210                 215             220

Ser Ala Ile Arg Gly Ile Arg Phe Leu Gln Ile Leu Arg Met Leu His
225                 230             235                 240

Val Asp Arg Gln Gly Gly Thr Trp Arg Leu Leu Gly Ser Val Val Phe
                245                 250             255

Ile His Arg Gln Glu Leu Ile Thr Thr Leu Tyr Ile Gly Phe Leu Gly
            260                 265             270

Leu Ile Phe Ser Ser Tyr Phe Val Tyr Leu Ala Glu Lys Asp Ala Val
        275                 280             285

Asn Glu Ser Gly Arg Val Glu Phe Gly Ser Tyr Ala Asp Ala Leu Trp
    290                 295             300

Trp Gly Val Val Thr Val Thr Thr Ile Gly Tyr Gly Asp Lys Val Pro
305                 310             315                 320

Gln Thr Trp Val Gly Lys Thr Ile Ala Ser Cys Phe Ser Val Phe Ala
                325                 330             335

Ile Ser Phe Phe Ala Leu Pro Ala Gly Ile Leu Gly Ser Gly Phe Ala
            340                 345             350

Leu Lys Val Gln Gln Lys Gln Arg Gln Lys His Phe Asn Arg Gln Ile
        355                 360             365

Pro Ala Ala Ala Ser Leu Ile Gln Thr Ala Trp Arg Cys Tyr Ala Ala
    370                 375             380

Glu Asn Pro Asp Ser Ser Thr Trp Lys Ile Tyr Ile Arg Lys Ala Pro
385                 390             395                 400

Arg Ser His Thr Leu Leu Ser Pro Ser Pro Lys Pro Lys Lys Ser Val
                405                 410             415

Val Val Lys Lys Lys Lys Phe Lys Leu Asp Lys Asp Asn Gly Val Thr
            420                 425             430

Pro Gly Glu Lys Met Leu Thr Val Pro His Ile Thr Cys Asp Pro Pro
```

-continued

```
                435                 440                 445
Glu Glu Arg Arg Leu Asp His Phe Ser Val Asp Gly Tyr Asp Ser Ser
    450                 455                 460

Val Arg Lys Ser Pro Thr Leu Leu Glu Val Ser Met Pro His Phe Met
465                 470                 475                 480

Arg Thr Asn Ser Phe Ala Glu Asp Leu Asp Leu Glu Gly Glu Thr Leu
                485                 490                 495

Leu Thr Pro Ile Thr His Ile Ser Gln Leu Arg Glu His His Arg Ala
            500                 505                 510

Thr Ile Lys Val Ile Arg Arg Met Gln Tyr Phe Val Ala Lys Lys Lys
        515                 520                 525

Phe Gln Gln Ala Arg Lys Pro Tyr Asp Val Arg Asp Val Ile Glu Gln
530                 535                 540

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
                565                 570                 575

Ser Glu Lys Ser Lys Asp Arg Gly Ser Asn Thr Ile Gly Ala Arg Leu
            580                 585                 590

Asn Arg Val Glu Asp Lys Val Thr Gln Leu Asp Gln Arg Leu Ala Leu
        595                 600                 605

Ile Thr Asp Met Leu His Gln Leu Leu Ser Leu His Gly Gly Ser Thr
    610                 615                 620

Pro Gly Ser Gly Gly Pro Pro Arg Glu Gly Gly Ala His Ile Thr Gln
625                 630                 635                 640

Pro Cys Gly Ser Gly Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
            660                 665                 670

Asp Glu Gly Ser
    675

<210> SEQ ID NO 30
<211> LENGTH: 844
<212> TYPE: PRT
<213> ORGANISM: Homo sapiens

<400> SEQUENCE: 30

Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
        35                  40                  45

Lys Arg Gly Ser Ile Leu Ser Lys Pro Arg Ala Gly Gly Ala Gly Ala
    50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125
```

```
Leu Glu Ile Val Thr Ile Val Phe Gly Val Glu Tyr Phe Val Arg
    130                 135             140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
        355                 360                 365

Val Pro Met Tyr Arg Leu Ile Pro Pro Leu Asn Gln Leu Glu Leu Leu
    370                 375                 380

Arg Asn Leu Lys Ser Lys Ser Gly Leu Ala Phe Arg Lys Asp Pro Pro
385                 390                 395                 400

Pro Glu Pro Ser Pro Ser Gln Lys Val Ser Leu Lys Asp Arg Val Phe
                405                 410                 415

Ser Ser Pro Arg Gly Val Ala Ala Lys Gly Lys Gly Ser Pro Gln Ala
            420                 425                 430

Gln Thr Val Arg Arg Ser Pro Ser Ala Asp Gln Ser Leu Glu Asp Ser
        435                 440                 445

Pro Ser Lys Val Pro Lys Ser Trp Ser Phe Gly Asp Arg Ser Arg Ala
    450                 455                 460

Arg Gln Ala Phe Arg Ile Lys Gly Ala Ala Ser Arg Gln Asn Ser Glu
465                 470                 475                 480

Glu Ala Ser Leu Pro Gly Glu Asp Ile Val Asp Asp Lys Ser Cys Pro
                485                 490                 495

Cys Glu Phe Val Thr Glu Asp Leu Thr Pro Gly Leu Lys Val Ser Ile
            500                 505                 510

Arg Ala Val Cys Val Met Arg Phe Leu Val Ser Lys Arg Lys Phe Lys
        515                 520                 525

Glu Ser Leu Arg Pro Tyr Asp Val Met Asp Val Ile Glu Gln Tyr Ser
    530                 535                 540

Ala Gly His Leu Asp Met Leu Ser Arg Ile Lys Ser Leu Gln Ser Arg
```

```
                545                 550                 555                 560
        Val Asp Gln Ile Val Gly Arg Gly Pro Ala Ile Thr Asp Lys Asp Arg
                        565                 570                 575

Thr Lys Gly Pro Ala Glu Ala Glu Leu Pro Glu Asp Pro Ser Met Met
                    580                 585                 590

Gly Arg Leu Gly Lys Val Glu Lys Gln Val Leu Ser Met Glu Lys Lys
                    595                 600                 605

Leu Asp Phe Leu Val Asn Ile Tyr Met Gln Arg Met Gly Ile Pro Pro
                    610                 615                 620

Thr Glu Thr Glu Ala Tyr Phe Gly Ala Lys Glu Pro Glu Pro Ala Pro
        625                 630                 635                 640

Pro Tyr His Ser Pro Glu Asp Ser Arg Glu His Val Asp Arg His Gly
                    645                 650                 655

Cys Ile Val Lys Ile Val Arg Ser Ser Ser Thr Gly Gln Lys Asn
                    660                 665                 670

Phe Ser Ala Pro Pro Ala Ala Pro Val Gln Cys Pro Pro Ser Thr
                    675                 680                 685

Ser Trp Gln Pro Gln Ser His Pro Arg Gln His Gly Thr Ser Pro
                    690                 695                 700

Val Gly Asp His Gly Ser Leu Val Arg Ile Pro Pro Pro Ala His
        705                 710                 715                 720

Glu Arg Ser Leu Ser Ala Tyr Gly Gly Gly Asn Arg Ala Ser Met Glu
                    725                 730                 735

Phe Leu Arg Gln Glu Asp Thr Pro Gly Cys Arg Pro Pro Glu Gly Thr
                    740                 745                 750

Leu Arg Asp Ser Asp Thr Ser Ile Ser Ile Pro Ser Val Asp His Glu
                    755                 760                 765

Glu Leu Glu Arg Ser Phe Ser Gly Phe Ser Ile Ser Gln Ser Lys Glu
                    770                 775                 780

Asn Leu Asp Ala Leu Asn Ser Cys Tyr Ala Ala Val Ala Pro Cys Ala
        785                 790                 795                 800

Lys Val Arg Pro Tyr Ile Ala Glu Gly Glu Ser Asp Thr Asp Ser Asp
                    805                 810                 815

Leu Cys Thr Pro Cys Gly Pro Pro Arg Ser Ala Thr Gly Glu Gly
                    820                 825                 830

Pro Phe Gly Asp Val Gly Trp Ala Gly Pro Arg Lys
                    835                 840

<210> SEQ ID NO 31
<211> LENGTH: 695
<212> TYPE: PRT
<213> ORGANISM: Homo sapiens

<400> SEQUENCE: 31

Met Ala Glu Ala Pro Pro Arg Arg Leu Gly Leu Gly Pro Pro Gly
        1               5                   10                  15

Asp Ala Pro Arg Ala Glu Leu Val Ala Leu Thr Ala Val Gln Ser Glu
                    20                  25                  30

Gln Gly Glu Ala Gly Gly Gly Ser Pro Arg Arg Leu Gly Leu Leu
                    35                  40                  45

Gly Ser Pro Leu Pro Pro Gly Ala Pro Leu Pro Gly Pro Gly Ser Gly
                    50                  55                  60

Ser Gly Ser Ala Cys Gly Gln Arg Ser Ser Ala Ala His Lys Arg Tyr
        65                  70                  75                  80
```

-continued

```
Arg Arg Leu Gln Asn Trp Val Tyr Asn Val Leu Glu Arg Pro Arg Gly
                85                  90                  95

Trp Ala Phe Val Tyr His Val Phe Ile Phe Leu Leu Val Phe Ser Cys
            100                 105                 110

Leu Val Leu Ser Val Leu Ser Thr Ile Gln Glu His Gln Glu Leu Ala
        115                 120                 125

Asn Glu Cys Leu Leu Ile Leu Glu Phe Val Met Ile Val Phe Gly
130                 135                 140

Leu Glu Tyr Ile Val Arg Val Trp Ser Ala Gly Cys Cys Cys Arg Tyr
145                 150                 155                 160

Arg Gly Trp Gln Gly Arg Phe Arg Phe Ala Arg Lys Pro Phe Cys Val
                165                 170                 175

Ile Asp Phe Ile Val Phe Val Ala Ser Val Ala Val Ile Ala Ala Gly
            180                 185                 190

Thr Gln Gly Asn Ile Phe Ala Thr Ser Ala Leu Arg Ser Met Arg Phe
        195                 200                 205

Leu Gln Ile Leu Arg Met Val Arg Met Asp Arg Arg Gly Gly Thr Trp
    210                 215                 220

Lys Leu Leu Gly Ser Val Val Tyr Ala His Ser Lys Glu Leu Ile Thr
225                 230                 235                 240

Ala Trp Tyr Ile Gly Phe Leu Val Leu Ile Phe Ala Ser Phe Leu Val
                245                 250                 255

Tyr Leu Ala Glu Lys Asp Ala Asn Ser Asp Phe Ser Ser Tyr Ala Asp
            260                 265                 270

Ser Leu Trp Trp Gly Thr Ile Thr Leu Thr Thr Ile Gly Tyr Gly Asp
        275                 280                 285

Lys Thr Pro His Thr Trp Leu Gly Arg Val Leu Ala Ala Gly Phe Ala
    290                 295                 300

Leu Leu Gly Ile Ser Phe Phe Ala Leu Pro Ala Gly Ile Leu Gly Ser
305                 310                 315                 320

Gly Phe Ala Leu Lys Val Gln Glu Gln His Arg Gln Lys His Phe Glu
                325                 330                 335

Lys Arg Arg Met Pro Ala Ala Asn Leu Ile Gln Ala Ala Trp Arg Leu
            340                 345                 350

Tyr Ser Thr Asp Met Ser Arg Ala Tyr Leu Thr Ala Thr Trp Tyr Tyr
        355                 360                 365

Tyr Asp Ser Ile Leu Pro Ser Phe Arg Glu Leu Ala Leu Leu Phe Glu
    370                 375                 380

His Val Gln Arg Ala Arg Asn Gly Gly Leu Arg Pro Leu Glu Val Arg
385                 390                 395                 400

Arg Ala Pro Val Pro Asp Gly Ala Pro Ser Arg Tyr Pro Pro Val Ala
                405                 410                 415

Thr Cys His Arg Pro Gly Ser Thr Ser Phe Cys Pro Gly Glu Ser Ser
            420                 425                 430

Arg Met Gly Ile Lys Asp Arg Ile Arg Met Gly Ser Ser Gln Arg Arg
        435                 440                 445

Thr Gly Pro Ser Lys Gln Gln Leu Ala Pro Pro Thr Met Pro Thr Ser
    450                 455                 460

Pro Ser Ser Glu Gln Val Gly Glu Ala Thr Ser Pro Thr Lys Val Gln
465                 470                 475                 480

Lys Ser Trp Ser Phe Asn Asp Arg Thr Arg Phe Arg Ala Ser Leu Arg
                485                 490                 495

Leu Lys Pro Arg Thr Ser Ala Glu Asp Ala Pro Ser Glu Glu Val Ala
```

-continued 500                   505                   510
Glu Glu Lys Ser Tyr Gln Cys Glu Leu Thr Val Asp Asp Ile Met Pro
        515                   520                   525

Ala Val Lys Thr Val Ile Arg Ser Ile Arg Ile Leu Lys Phe Leu Val
        530                   535                   540

Ala Lys Arg Lys Phe Lys Glu Thr Leu Arg Pro Tyr Asp Val Lys Asp
545                   550                   555                   560

Val Ile Glu Gln Tyr Ser Ala Gly His Leu Asp Met Leu Gly Arg Ile
                    565                   570                   575

Lys Ser Leu Gln Thr Arg Val Asp Gln Ile Val Gly Arg Gly Pro Gly
                580                   585                   590

Asp Arg Lys Ala Arg Glu Lys Gly Asp Lys Gly Pro Ser Asp Ala Glu
        595                   600                   605

Val Val Asp Glu Ile Ser Met Met Gly Arg Val Val Lys Val Glu Lys
        610                   615                   620

Gln Val Gln Ser Ile Glu His Lys Leu Asp Leu Leu Leu Gly Phe Tyr
625                   630                   635                   640

Ser Arg Cys Leu Arg Ser Gly Thr Ser Ala Ser Leu Gly Ala Val Gln
                645                   650                   655

Val Pro Leu Phe Asp Pro Asp Ile Thr Ser Asp Tyr His Ser Pro Val
                660                   665                   670

Asp His Glu Asp Ile Ser Val Ser Ala Gln Thr Leu Ser Ile Ser Arg
            675                   680                   685

Ser Val Ser Thr Asn Met Asp
        690                   695